(12) United States Patent
Ballhause et al.

(10) Patent No.: US 8,679,745 B2
(45) Date of Patent: Mar. 25, 2014

(54) METHOD FOR PROVIDING DNA FRAGMENTS DERIVED FROM AN ARCHIVED SAMPLE

(75) Inventors: Matthias Ballhause, Berlin (DE); Kurt Berlin, Stahnsdorf (DE); Dimo Dietrich, Berlin (DE); Antje Kluth Lukas, Wentorf (DE); Matthias Schuster, Berlin (DE); Ute Wagner, Berlin (DE); Reinhold Wasserkort, Berlin (DE); Heike Ziebarth, Berlin (DE)

(73) Assignee: Epigenomics AG, Berlin (DE)

( * ) Notice: Subject to any disclaimer, the term of this patent is extended or adjusted under 35 U.S.C. 154(b) by 479 days.

(21) Appl. No.: 11/664,367

(22) PCT Filed: Sep. 30, 2005

(86) PCT No.: PCT/US2005/035317
§ 371 (c)(1),
(2), (4) Date: Jan. 11, 2008

(87) PCT Pub. No.: WO2006/039563
PCT Pub. Date: Apr. 13, 2006

(65) Prior Publication Data
US 2008/0220418 A1 Sep. 11, 2008

Related U.S. Application Data

(60) Provisional application No. 60/614,697, filed on Sep. 30, 2004.

(51) Int. Cl.
*C12Q 1/68* (2006.01)
*C12P 19/34* (2006.01)
*B01L 3/00* (2006.01)

(52) U.S. Cl.
USPC ........... 435/6.1; 435/91.1; 435/91.2; 422/430

(58) Field of Classification Search
USPC .......................... 435/6.1, 91.1, 91.2; 422/430
See application file for complete search history.

(56) References Cited

U.S. PATENT DOCUMENTS

| | | | |
|---|---|---|---|
| 5,786,146 A | 7/1998 | Herman et al. | |
| 6,248,535 B1 | 6/2001 | Danenberg et al. | |
| 6,605,432 B1 | 8/2003 | Huang | |
| 7,214,485 B2 | 5/2007 | Belinsky et al. | |
| 7,288,373 B2 * | 10/2007 | Millar et al. | 435/6.14 |
| 7,407,749 B2 | 8/2008 | Berlin et al. | |
| 2004/0115663 A1 | 6/2004 | Berlin et al. | |
| 2009/0004646 A1 | 1/2009 | Schuster et al. | |

FOREIGN PATENT DOCUMENTS

| | | | | |
|---|---|---|---|---|
| DE | 100 50 942 A1 * | 4/2002 | | C12Q 1/68 |
| EP | 1 670 949 B1 * | 5/2009 | | C12Q 1/68 |
| GB | 2 369 822 | 6/2002 | | |
| WO | WO 99/28498 | 6/1999 | | |
| WO | WO 01/38565 | 5/2001 | | |
| WO | WO 01/98528 | 12/2001 | | |
| WO | WO 02/18632 | 3/2002 | | |
| WO | WO 02/18649 | 3/2002 | | |
| WO | WO 02/072880 | 9/2002 | | |
| WO | WO 02/086163 | 10/2002 | | |
| WO | WO 03/083107 | 10/2003 | | |
| WO | WO 2004/113564 | 12/2004 | | |
| WO | WO 2005/038051 | 4/2005 | | |
| WO | WO 2005/123941 | 12/2005 | | |
| WO | WO2006/088978 | 8/2006 | | |

OTHER PUBLICATIONS

Jackson et al., Tissue extraction of DNA and RNA and analysis by the polymerase chain reaction, J. Clin. Pathol. 1990; 43; 499-504.*
Lehmann et al., Real-Time PCR Analysis of DNA and RNA Extracted from Formalin-Fixed and Paraffin-Embedded Biopsies1, Methods 25, 409-418 (2001).*
Qiagen, DNeasy® Tissue Handbook, May 2002, pp. 1-44.*
Cao et al., Comparison of methods for DNA extraction from paraffin-embedded tissues and buccal cells, Cancer Detection and Prevention 27:397-404, 2003.
Lehmann and Kreipe, Real-Time PCR Analysis of DNA and RNA Extracted from Formalin-Fixed and Paraffin-Embedded Biopsies, Methods 25:409-418, 2001.
U.S. Appl. No. 60/710,556, filed Aug. 23, 2005, Fassbender et al.
Bonin et al., "PCR analysis in archival postmortem tissues," Journal of Clinical Pathology, 2003, pp. 184-186, vol. 56.
Cottrell et al., "A real-time PCR assay for DNA-methylation using methylation-specific blockers," Nucleic Acids Research, 2004, p. e10, vol. 32, No. 1 (8 pages).
Cross et al., "Purification of CpG islands using a methylated DNA binding column," Nature Genetics, Mar. 1994, pp. 236-244, vol. 6.
Eads et al., "CpG Island Hypermethylation in Human Colorectal Tumors is not Associated with DNA Methyltransferase Overexpression," Cancer Research, May 15, 1999, pp. 2302-2306, vol. 59.
Fisher et al., "Characterization of cytosine methylated regions and 5-cytosine DNA methyltransferase (Ehmeth) in the protozoan parasite Entamoeba histolytica," Nucleic Acids Research, 2004, pp. 287-297, vol. 32, No. 1.

(Continued)

Primary Examiner — Jezia Riley
(74) Attorney, Agent, or Firm — DLA Piper LLP (US)

(57) ABSTRACT

Aspects of the present invention relate to compositions and methods for providing DNA fragments from an archived sample (e.g., paraffin-embedded and/or fixed-tissue biopsies, etc). Particular aspects provide methods whereby high yields of DNA are isolated as well as a substantial portion of the DNA consists of long DNA fragments, and where the isolated genomic DNA is free of associated or cross-linked contaminants like proteins, peptides, amino acids or RNA. The methods are facile, cost-effective, and are characterized by high reproducibility and reliability. Particular aspects provide methods for providing DNA fragments derived from an archived sample, wherein the yield of DNA before, for example, an amplification step is at least 20%, and amplicons up to a length of about 1,000 base pairs are amplifiable.

32 Claims, 22 Drawing Sheets

(56) References Cited

OTHER PUBLICATIONS

Frommer et al., "A genomic sequencing protocol that yields a positive display of 5-methylcytosine residues in individual DNA strands," PNAS, Mar. 1992, pp. 1827-1831, vol. 89.
Gardiner-Garden et al., "CpG Islands in Vertebrate Genomes," Journal of Molecular Biology, 1987, pp. 261-282, vol. 196.
Gonzalgo et al., "Identification and Characterization of Differentially Methylated Regions of Genomic DNA by Methylation-sensitve Arbitrarily Primed PCR," Cancer Research, Feb. 15, 1997, pp. 594-599, vol. 57.
Gonzalgo et al., Rapid quantitation of methylation differences at specific sites using methylation-sensitive single nucleotide primer extension (Ms-SNuPE), Nucleic Acids Research, 1997, pp. 2529-2531, vol. 25, No. 12.
Gretch et al., "The Use of Biotinylated Monoclonal Antibodies and Streptavidin Affinity Chromatography to Isolate Herpesvirus Hydrophobic Proteins or Glycoproteins," Analytical Biochemistry, 1987, pp. 270-277, vol. 163.
Grunau et al., "Bisulfite genomic sequencing: systematic investigation of critical experimental parameters," Nucleic Acids Research, 2001, p. e65, vol. 29, No. 13 (7 pages).
Gut et al, "DNA and Matrix Assisted Laser Desorption Ionization Mass Spectrometry," Molecular Biology: Current Innovations and Future Trends, 1995, pp. 147-157, Horizon Scientific Press, Wymondham, United Kingdom.
Gut et al., "A procedure for selection DNA alkylation and detection by mass spectrometry," Nucleic Acids Research, 1995, pp. 1367-1373, vol. 23, No. 8.
Hendrich et al., "The methyl-CpG binding domain and the evolving role of DNA methylation in animals," Trends in Genetics, May 2003, pp. 269-277, vol. 19, No. 5.
Herman et al., "Methylation-specific PCR: A novel PCR assay for methylation status of CpG islands," Sep. 1996, pp. 9821-9826, vol. 93.
Huang et al., "Methylation profiling of CpG islands in human breast cancer cells," Human Molecular Genetics, 1999, pp. 459-470, vol. 8, No. 3.
Inadome et al., "Selection of Higher Molecular Weight Genomic DNA for Molecular Diagnosis From Formalin-Fixed Material," Diagnostic Molecular Pathology, Dec. 2003, pp. 231-236, vol. 12, No. 4.
Janknecht et al., "Rapid and efficient purification of native histidine-tagged protein expressed by recombinant vaccinia virus," PNAS, Oct. 1991, pp. 8972-8976, vol. 88.
Jørgensen et al., "Mbd1 is Recruited to both Methylated and Nonmethylated CpGs via Distinct DNA Binding Domains," Molecular and Cellular Biology, Apr. 2004, pp. 3387-3395, vol. 24, No. 8.
Kapranov et al., "Large-Scale Transcriptional Activity in Chromosomes 21 and 22," Science, May 3, 2002, pp. 916-919, vol. 296.
Karas et al., "Laser Desorption Ionization of Proteins with Molecular Masses Exceeding 10 000 Daltons," Analytical Chemistry, Oct. 15, 1988, pp. 2299-2301, vol. 60, No. 20.
Kawakami et al., "Hypermethylated APC DNA in Plasma and Prognosis of Patients With Esophageal Adenocarcinoma," Journal of the National Cancer Institute, Nov. 15, 2000, pp. 1805-1811, vol. 92, No. 22.
Matarazzo et al., "In vivo analysis of DNA methylation patterns recognized by specific proteins: coupling ChIP and bisulfite analysis," BioTechniques, 2004, pp. 666-673, vol. 37, No. 4.
Olek et al., "A modified and improved method for bisulphite based cytosine methylation analysis," Nucleic Acids Research, 1996, pp. 5064-5066, vol. 24, No. 24.
Sadri et al., "Rapid analysis of DNA methylation using new restriction enzyme sites created by bisulfite modification," Nucleic Acids Research, 1996, pp. 5058-5059, vol. 24, No. 24.
Shiraishi et al., "Methyl-CpG binding domain column chromatography as a tool for the analysis of genomic DNA methylation," Analytical Biochemistry, 2004, pp. 1-10, vol. 329.
Siwoski et al., "An Efficient Method fo rthe Assessment of DNA Quality of Archival Microdissected Specimens," Modern Pathology, 2002, pp. 889-892, vol. 15, No. 8.
Tie et al., "Individual identification by DNA polymorphism using formalin-fixed placenta with whole genome amplification," Pathology International, 2005, pp. 343-347, vol. 55.
Xiong et al., "COBRA: a sensitive and quantitative DNA methylation assay," Nucleic Acids Research, 1997, pp. 2532-2534, vol. 25, No. 12.

\* cited by examiner

METHOD FOR PROVIDING DNA FRAGMENTS DERIVED FROM AN ARCHIVED SAMPLE

CROSS-REFERENCE TO RELATED APPLICATIONS

This application claims the benefit of priority to U.S. Provisional Patent Application Ser. Nos. 61/173,134 filed Apr. 27, 2009 and 61/175,409 filed May 4, 2009, both of which are incorporated by reference herein in their entirety.

FIELD OF THE INVENTION

The invention relates generally to novel and substantially improved compositions and methods for providing DNA fragments derived from an archived sample (e.g., paraffin-embedded and/or fixed-tissue biopsies, etc), and for analyses of same.

BACKGROUND OF ASPECTS OF THE INVENTION

Samples or biopsies are archived many times by default in diagnostic routines. This is done in order to conserve the tissue and to prepare it for subsequent histological examinations. Such conservation is necessary to ensure that the biopsy has not changed after the removal, the observed findings correspond to the situation of the patient, and to prevent degradation of cell structures. Accordingly, the tissue sample is immediately put into a fixative for example formalin after removal. After fixation the sample is embedded into paraffin, which allows a sectioning of the tissue and a subsequent further histological examination.

Using these procedures, biopsies are routinely taken from patients for diagnosing diseases and/or for studying the pattern of markers associated with diseases. Over the last decades millions of biopsies were collected, archived and stored in this way. These samples represent a major resource for the detection or analysis of disorders or disease associated alterations. Therefore these samples are invaluable, because they allow the evaluation of diagnostic and/or prognostic indicators in retrospective collections.

But unfortunately, this resource is only minimally accessible by molecular biological means, in particular by the most promising and modern methods such as those for the analysis of the methylation pattern. This is because of difficulties in obtaining sufficiently large amounts of high quality genomic DNA at low costs and with minimal handling effort.

These difficulties are based on the degradation of DNA and RNA due to fixation and storage conditions of the sample or biopsy, and on the insufficient methods for the preparation of DNA. To preserve morphological structures in the sample as well as possible, biopsies are usually fixed very well. This has the disadvantage that a lot of proteins are covalently linked to the genomic DNA and also the genomic DNA becomes cross-linked. Consequently, genomic DNA tends to be of small fragment size, has a low integrity, and is contaminated by proteins, peptides and/or amino acids which are cross linked with the DNA and which also interfere with further analysis.

Most prior art methods for the isolation of DNA from paraffin embedded formalin-fixed tissues are based on methods for the isolation of DNA from fresh tissue. They are carried out as one skilled in the art would treat fresh samples maybe with an additional paraffin removal step. As it is well known, such a procedure leads only to comparably low yields of genomic DNA, the DNA having only a small fragment length. Furthermore, the DNA is also not suitable for more sophisticated analysis methods, because still a lot of interfering proteins, peptides and/or amino acids are linked to the DNA.

Particular 'improved' methods are known in the art. For example U.S. Pat. No. 6,248,535 teaches a method for the isolation of nucleic acids from paraffin embedded formalin-fixed tissue. According to this method, the sample gets deparaffinized, homogenized before it is heated in a chaotropic solution. After mixing with chloroform, following centrifugation, the solution has three phases. The interphase contains the genomic DNA.

A different method is described by GB 2369822. According to this, sections of a paraffin-embedded formalin-fixed sample are put into a tube. A detergent, a wax and a tissue-digesting enzyme are added, before the tube is heated to about 60° C. for about 30 min. After this the enzyme is inactivated by a temperature increase to 96° C. A subsequent centrifugation step leads to a layering inside the tube, the middle layer containing the genomic DNA as well the RNA.

Such methods usually lead to larger amounts of genomic DNA with a lot of contaminating RNA and protein. In addition, the contaminants cannot be easily removed because they are cross-linked to the genomic DNA by the fixative. Moreover, in principle, it may be possible to also isolate longer nucleic acid fragments with these kinds of methods, but the portion of long fragments is very small.

Several proposals have been made to get longer fragments: Bonin et al. teach a filling in of single-stranded breaks after isolation of the DNA and a denaturing step before PCR amplification (Bonin S., Petrera, F., Niccolini, B., Stanta, G. (2003) J. Clin. Pathol: Mol. Pathol. 56, 184-186). According to this method fragments up to 300 bp are amplifiable.

Inadome et al. suggest the isolation of the portion of longer DNA fragments by HPLC (Inadome, Y., Noguchi, M. (2003) Diagn. Mol. Pathol. 12, 231-236). This procedure leads only to very low yields of DNA.

To enlarge the amount of long DNA fragments isolated from paraffin-embedded, formalin-fixed tissues, a whole genome amplification was suggested by Tie et al. and Siwoski et al. (Tie, J., Serizawa, Y., Oshida, S., Usami, R., Yoshida Y. (2005) Pathol. Int. 55, 343-347; Siwoski, A., Ishkanianu, A., Garnis, C., Zhang, L., Rosin, M., Lam, W. L. (2002) Mod. Pathol. 15, 889-892.). This solution has the disadvantage of a low reproducibility and is not applicable when DNA is going to be analysed for methylation as amplification erases methylation signals.

Consequently, genomic DNA isolated according to prior art methods is not suitable for analysis of the methylation pattern as explained in detail below.

The importance of DNA methylation pattern analyses has been revealed in recent years. Many diseases, in particular cancer diseases, are accompanied by modified gene expression. This may be a mutation of the genes themselves, which leads to an expression of modified proteins or to an inhibition or over-expression of the proteins or enzymes. A modulation of the expression may however also occur by epigenetic modifications, in particular by changes in the DNA methylation pattern. Such epigenetic modifications do not affect the actual DNA coding sequence. It has been found that DNA methylation processes have substantial implications for health, and it seems to be clear that knowledge about methylation processes and modifications of the methyl metabolism and DNA methylation are essential for understanding diseases, for the prophylaxis, diagnosis and therapy of diseases.

The precise control of genes, which represent a small part only of the complete genome of mammals, involves regulation in consideration of the fact that the main part of the DNA in the genome is not coding. The presence of such 'trunk' DNA containing introns, repetitive elements and potentially actively transposable elements, requires effective mechanisms for their durable suppression (silencing). Apparently, the methylation of cytosine by S-adenosylmethionine (SAM) dependent DNA methyl transferases, which form 5-methylcytosine, represents such a mechanism for the modification of DNA-protein interactions. Genes can be transcribed by methylation-free promoters, even when adjacent transcribed or not-transcribed regions are widely methylated. This permits the use and regulation of promoters of functional genes, whereas the trunk DNA including the transposable elements is suppressed. Methylation also takes place for the long-term suppression of X-linked genes and may lead to either a reduction or an increase of the degree of transcription, depending on where the methylation in the transcription units occurs.

Nearly the complete natural DNA methylation in mammals is restricted to cytosine-guanosine (CpG) dinucleotide palindrome sequences, which are controlled by DNA methyl transferases. CpG dinucleotides are about 1 to 2% of all dinucleotides and are concentrated in CpG islands. According to an art-recognized definition, a region is considered as a CpG island when the C+G content over 200 bp is at least 50% and the percentage of the observed CG dinucleotides in comparison to the expected CG dinucleotides is larger than 0.6 (Gardiner-Garden, M., Frommer, M. (1987) J. Mol. Biol. 196, 261-282). Typically, CpG islands have at least 4 CpG dinucleotides in a sequence of a length of 100 bp.

CpG islands located in promotor regions frequently have a regulatory function for the expression of the corresponding gene. For example, in case the CpG island is hypomethylated, the gene can be expressed. On the other hand, hypermethylation frequently leads to a suppression of the expression. Normally tumour suppressor genes are hypomethylated. But if they become hypermethylated, their expression becomes suppressed. This is observed many times in tumour tissues. By contrast, oncogenes are hypermethylated in healthy tissue, whereas they are hypomethylated in many times in tumour tissues.

The methylation of cytosine has the effect that the binding of proteins is normally prohibited which regulate the transcription of genes. This leads to an alteration of the expression of the gene. Relating to cancer, the expression of genes regulating cell division are thereby altered, for example, the expression of an apoptotic gene is down regulated, while the expression of an oncogene is up regulated. Additionally, hypermethylation may have a long term influence on regulation. Proteins, which deacetylate histones, are able to bind via their 5-methylcytosine binding domain to the DNA when the cytosines get methylated. This results in a deacetylation of the histones, which itself leads to a tighter package of the DNA. Because of that, regulatory proteins are not precluded from binding to the DNA.

Pronounced need in the art. The efficient detection of DNA methylation patterns consequently is an important tool for developing new approaches to understand diseases, for the prevention, diagnosis and treatment of diseases and for the screening for disease associated targets. But on the other hand, methods for an efficient detection of DNA methylation require high quality standards in regard to the starting material the genomic DNA. Preferably, the standards are: i) DNA fragment range is between 150 to 1200 bp; and ii) the DNA is free of associated or cross linked proteins, peptides, amino acids, RNA as well as of nucleotides or bases, which are not part of the DNA backbone.

Furthermore, there are also requirements with regard to the methods according to which the DNA is isolated. The reason for these is that a lot of samples are typically analysed for developing new approaches for the prevention, diagnosis and treatment of a disease and for the screening for disease associated targets. Preferably, the requirements are: i) isolation of high quality DNA (as specified above); ii) high reproducibility; iii) high reliability, iv) ease of handling; v) low handling effort; and vi) low costs.

Additionally, because in general the amount of the tissue sample or biopsy is very small, it is necessary that the methods for DNA preparation result in high yields of DNA.

Because of all these requirements, and given the prior art methods, archived samples, despite being a major resource in medical science, can only be minimally used for the efficient analysis of the DNA methylation. Thus a major technical need exists to efficiently make archived samples (e.g., paraffin-embedded formalin-fixed tissues) available for the analysis of, for example, the DNA methylation patterns.

Thus far, applicants are aware of only one attempt to solve this problem. WO03/083107 teaches a method for isolation of genomic DNA from paraffin-embedded suitable for subsequent DNA methylation analysis by methylation specific PCR (MSP). In principle the deparaffiniated formalin-fixed sample is boiled in a citrate buffer pH 6.0, which recovers parts of the cytosines making them better accessible for subsequent treatment and analysis. However this method is conflicting with regard to the aim to provide as long as possible DNA fragments. According to this method DNA is brought into contact with a buffer of acidic pH. As is well known in the relevant art, such treatment reduces the integrity of DNA resulting in a random breakage of the DNA strand and therefore the length of the DNA fragments.

SUMMARY OF ASPECTS OF THE INVENTION

Aspects of the present invention relate to compositions and methods for providing DNA fragments from an archived sample. Particular aspects provide compositions and methods for providing DNA fragments derived from an archived sample, wherein the yield of DNA before, for example, an amplification step is at least 20%, and amplicons up to a length of about 1,000 base pairs are amplifiable.

Additional aspects provide a method for the preparation of genomic DNA from archived paraffin-embedded formalin-fixed tissue samples, whereby high yields of DNA are isolated as well as a substantial portion of the DNA consists of long DNA fragments. In particular aspects, the isolated genomic DNA is free of associated or cross-linked contaminants like proteins, peptides, amino acids or RNA. In particular aspects, the methods are characterized by high reproducibility and high reliability. In particular aspects, the methods are easy to handle, have a low handling effort, and are cost-effective.

Particularly preferred embodiments provide compositions and methods is further characterized in that
i) DNA extracted from an archived sample is subject to a bisulfite treatment;
ii) the yield of DNA after a bisulfite treatment step and a subsequent purification step and before an amplification step is 30-50%;
iii) amplicons up to a length of 600 base pairs are amplifiable after bisulfite treatment and subsequent purification; and
iv) in the average at least 10% of the DNA fragments are amplifiable after bisulfite treatment and subsequent purification in a PCR reaction resulting in fragments of at least 110 bp length.

Additional aspects provide a test kit for carrying out the method of the invention or an embodiment of the method of the invention. In particular aspects, the test kits comprise one or more of the following: a container, organic solvents for the removal of paraffin, proteinase K, buffer for the lysis of tissue, solutions and/or devices for DNA extraction, solutions and/or devices for bisulfite treatment, solutions and/or devices for DNA purification, solutions and/or substances for DNA amplification, a manual and/or description for carrying out the method according to the invention.

DETAILED DESCRIPTION OF ASPECTS OF THE INVENTION

Figure 1:
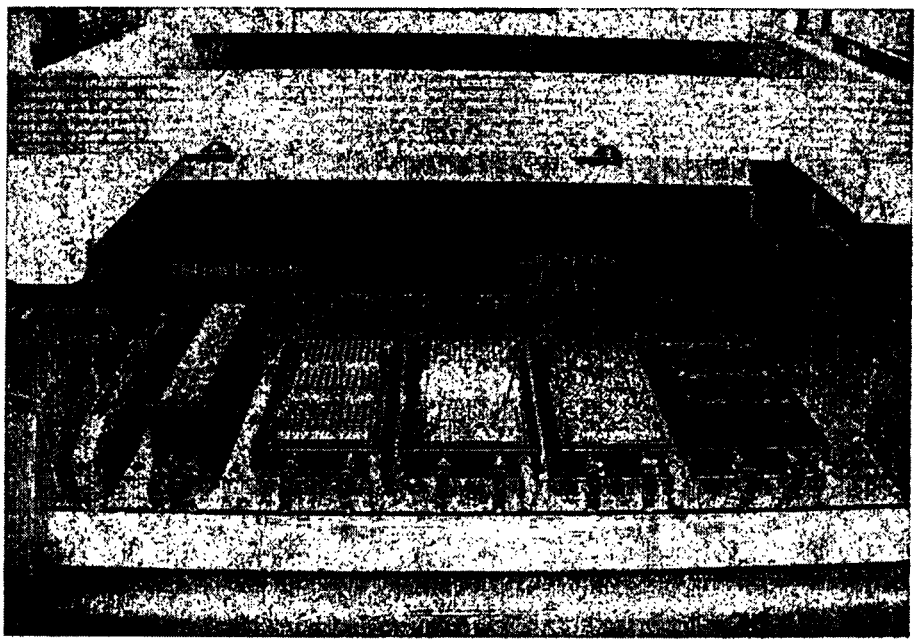
FIG. 1 shows, according to particular aspects, positions of the DNA samples and PCR plates on a TECAN® workstation.

For achieving various technical objects, aspects the invention teach compositions and methods for providing DNA fragments derived from an archived sample, characterized in that the yield of DNA before an amplification step is at least 20%, and amplicons up to a length of 1,000 base pairs are amplifiable. Particular aspects provide methods to find amongst an enormous plurality of known methods for paraffin removal, tissue lysis, DNA extraction, bisulfite treatment, DNA purification and DNA amplification those methods, which in principle can be used to solve the technical object of the invention. Particular aspects provide suitable combinations and adjustments of these methods with each other in a manner that actually meets the technical object(s).

ADVANTAGES OF ASPECTS OF THE INVENTION

In particular aspects, the exemplary inventive method has the following advantages: It has a low handling effort, because it includes only a very limited amount of steps which has to be carried out. Additionally, it is possible to carry out the method of the invention in a plate scale. Moreover the different steps can also be automated and therefore robotics can also be used. The execution in plate scale and the suitability of the method for automatisation also lead to a reduction in costs. In addition the costs are further reduced by the use of devices and solutions which are available at low expenses.

Another advantage of the method of the invention is that every step can easily be performed because only standard laboratory equipment is necessary for its execution.

Because of its simpleness, its suitability for automatisation, its low handling effort as well as its easy handling, the method of the invention has a high reliability and reproducibility.

In addition, DNA provided by this method is characterized by its high quality, even where an archieved paraffin-embedded formalin-fixed sample was used as a starting material. Furthermore, DNA provided according to this method comprises a notable fraction of long fragments (in the average 10% of the fragments have at least a length of 110 bp) and surprisingly long fragments are amplifiable (up to 600 bp). The DNA is further characterised that only minor contaminant proteins or peptides are linked to it. These contaminations are only so slightly that the bisulfite treatment is only faintly impaired if at all.

On the other hand, relatively high yields of DNA can be obtained reliably from the archieved sample with an additional high reproducibility. Therefore it is possible to obtain from only very small samples sufficient DNA for methylation analysis.

METHOD OF ASPECTS OF THE INVENTION

The method of the invention is a method for providing DNA fragments derived from an archived sample. According to the method of the invention, the yield of DNA before any amplification is at least 20%. For determination of the yield of DNA, the yield of DNA of every step of the method according to the invention is determined. The overall yield is then calculated by multiplication of the yields of the individual steps as known by those skilled in the art. The yield of DNA for each individual step can be carried out (determined) as described in detail in the instant EXAMPLES 10, 12, and 14-18, or by any other suitable method known to those skilled in the art, for example UV 260/280 nm or gel electrophoresis especially in combination with a detection system like a phosphor imager.

Furthermore, particular aspects of the exemplary inventive are characterized in that amplicons up to a length of 1,000 bp are amplifiable, whether or not a bisulfite treatment is carried out. A bisulfite treatment step carried out according to the state of the art reduces the ability of amplification of amplicons if the bisulfite treated DNA is used as a template. However, the single steps of the exemplary inventive methods are harmonised in such a way and the bisulfite treatment step is carried out in such a way that the application of a bisulfite treatment has nearly no influence on the ability/efficiency of amplification.

In brief, the method of the invention is a method for providing DNA fragments derived from an archived sample, which is characterized in that
  the yield of DNA before an amplification step is at least 20%, and
  amplicons up to a length of 1,000 base pairs are amplifiable.

At this, amplifiable means that any amplicon of a desired length can be amplified by the corresponding primers during a PCR amplification. The PCR amplification can be standard PCR or real time PCR or any known PCR amplification known to those skilled in the art. Of course, also methods which lead to similar results like ligase mediated chain reaction (LCR) or the NASBA/TMA technique can be used. The amplicon is then detected by means of fluorescence by standard techniques, for example by means of intercalating dyes like ethidium bromide or SYBR green or labels attached to the used primers or nucleotides. Suitable methods for detection are known to those skilled in the art.

In a further embodiment, the method of the invention is characterized in that
  the yield of DNA before an amplification step is 20-60%, and
  amplicons up to a length of 600 base pairs are amplifiable.

In a particular preferred embodiment the method of the invention comprises a bisulfite treatment step. After the then necessary DNA purification step, the overall yield of DNA is at least 20%, preferable in the range of 30-50%. Furthermore, the DNA after bisulfite treatment and the purification step is further characterized in that at least 5 of the DNA fragments are amplifiable in a PCR reaction resulting in fragments of at least 110 bp in length. In a particularly preferred embodiment, this DNA is characterized in that 5-60% of the DNA fragments are amplifiable in a PCR reaction resulting in fragments of at least 110 bp in length. In an especially preferred embodiment, an average of 10% of the purified DNA is amplifiable in a PCR reaction resulting in fragments of at least 110 bp length. These values can be determined as exemplified in example 10 and 14.

Therefore, in an embodiment, the method of the invention is a method for providing DNA fragments derived from an archived sample, characterized in that
a) the DNA is extracted,
b) the extracted DNA is treated with bisulfite
c) the bisulfite treated DNA is purified, whereby
  (i) the yield of purified DNA is at least 20% of the DNA contained in the archived sample,
  (ii) at least 5% of the purified DNA is amplifiable in a PCR reaction generating fragments of at least 110 bp length.

In a preferred embodiment, the method of the invention is characterised in that the yield of the DNA in step c (i) is between 30-50%

In a preferred embodiment, the method of the invention is charaterised in that in step c (ii) 5-60% of the purified DNA is amplifiable in a PCR reaction generating fragments of at least 110 bp length In a preferred embodiment, the method of the invention is characterised in that in step c (ii) an average of 10% of the purified DNA is amplifiable in a PCR reaction generating fragments of at least 110 bp length.

In a especially preferred embodiment, the method of the invention is further characterized in that in the average at least 10% of the DNA fragments are amplifiable after bisulfit treatment and subsequent purification in a PCR reaction resulting in fragments of at least 110 bp length.

In another especially preferred embodiment, the method of the invention is further characterized in that between 7-60% of the DNA fragments are amplifiable after bisulfite treatment and subsequent purification in a PCR reaction resulting in fragments of at least 70 bp in length. More preferably, in the average 15% are amplifiable after bisulfite treatment and subsequent purification in a PCR reaction resulting in fragments of at least 70 bp in length.

Archived Sample

According to the invention the archived sample is a paraffin embedded and/or fixed tissue biopsy or a paraffin embedded and/or fixed tissue section or parts thereof for example microdissected samples. Thereby the term "biopsy" refers to any kind of needle biopsy or any kind of tissue sample collected during a surgery. Moreover, the term "tissue section" refers to any part of a biopsy for example derived by microtom sectioning of the biopsy.

As it is well known by those skilled in the art, it is difficult to determine the actual weight of a tissue section. These difficulties are caused therein that the section are usually brittle, teeny and sticky. Furthermore, it is also important to have in mind the percentage of paraffin which surrounds the tissue. According to the invention, samples are preferred which have a paraffin percentage of 50% or less. Typically 1-6, in particularly three sections of 10 µm thickness with a tissue area in the range of 0.7 cm×0.7 cm to 2.5 cm×3.5 cm are used as a starting material. A person with ordinary skills in the art will know how to adjust the method according to invention to use samples which have a paraffin percentage of more than 50% or in case sections are used with a smaller or larger tissue area. For samples obtained by biopsies, different amounts are chosen as a starting material. Typically 1-6, in particularly three sections of 10 µm thickness of a biopsy sample are used. The biopsy sample comprises 1-6, preferable 3 biopsies embedded into paraffin. Typical biopsies are cylindrical having a diameter of about 1 cm, the length cannot be standardised. A person with ordinary skills in the art will know to choose an sufficient amount of starting material from a biopsy sample if the sample contains more biopsies. In addition he would also knew how to choose an equivalent amount of non-sectioned biopsy, which can be used according to the invention. Again, a person with ordinary skills in the art will know how to choose an appropriate amount of starting material. Of course, the method of the invention is also applicable for samples fixed with other fixatives like glutaraldehyde, Bouin' fixative, isopentane, or alcohol based fixatives like methanol or ethanol.

In an embodiment of the invention, the archived sample is a formalin-fixed sample, typically embedded into paraffin. But also formalin treated samples which are not embedded into paraffin can be used as a starting material. Of course fresh or fresh frozen samples can also be subject of the method according to the invention which will than start directly with the lysis step.

In an embodiment of the invention the archived sample is a paraffin embedded and/or fixed tissue biopsy or a paraffin embedded and/or fixed tissue section.

STEPS OF THE METHOD ACCORDING TO THE INVENTION

An embodiment of the invention comprises an optional paraffin removal step, a lysis step, an optional DNA extraction step, an optional bisulfite treatment step, an optional purification step and an amplification step. The method can be carried out in plate scale or tube scale. It can be conducted manually or by a roboter. So, it is possible to carry out the method of the invention manually in tube scale as well as in plate scale manually or by a roboter. This latter possibility has the advantage of a low handling effort and a reduction in costs.

An embodiment of the invention comprises a paraffin removal step, a lysis step, a DNA extraction step, a bisulfite treatment step, a purification step and an amplification step.

In another embodiment, the archived sample is directly subjected to a lysis step, wherein the paraffin is liquefied by heating. This lysis step typically leads to DNA free from cross-links, making it possible to also leave out the DNA extraction step and continuing with the bisulfite treatment step if desired, followed by the amplification step.

For the two above mentioned embodiments, it is preferred that the bisulfite step can be left out as well as the subsequent purification step for suitable applications that may follow. Therefore in a particular embodiment it is preferred, that the DNA extraction step is carried out by means of MINELUTE™ columns which are part of the QIAAMP® DNA Micro Kit. Very surprisingly, such a proceeding leads to the advantage that the portion of amplificable DNA is comparably large if the eluate of the first step of elution from the MINELUTE™ columns is used (see below)

To leave out the bisulfite treatment step and the subsequent DNA purification step is also particularly preferred if a bisulfite treatment is not necessary for the analysis of the DNA methylation for example by use of restriction enzymes. An example for such a method is the DMH method as it is described below or the restriction assay also known as Mest evaluation method as described in DE102004029700.2 or in PCT/DE205/001109 (both references incorporated by its entirety.

In principle, for the above named embodiments, it is also possible to leave out the amplification step if it is not necessary for subsequent analysis like methylation sensitive restriction and subsequent southern blot analysis. On the other hand, an amplification step might be advantageous even it is not necessary for the real detection of the DNA methylation status. This is for example the case, if only low amounts of large DNA fragments are provided. An amplification will in this case cause a lowering of the sensitivity of the subsequent methods for the DNA methylation analysis.

The method according to invention comprises the following steps:
a) optional, a paraffin removal step,
b) a lysis step,
c) optional, a DNA extraction step
d) optional, a bisulfite treatment step
e) optional, a purification step
f) an amplification step Paraffin Removal Step According to the invention the paraffin removal step comprises the dissolving of paraffin by an organic solvent. In a preferred embodiment the sample is additional washed with another organic solvent which enables afterwards a better rehydratisation. Therefore in an embodiment the paraffin removal step comprises the dissolving of paraffin by an organic solvent or the dissolving of paraffin by an organic solvent and washing by another organic solvent.

In a preferred embodiment, the organic solvent which dissolves paraffin is a solvent of the group "limonene, xylene or any mixture of these solvents". In particular, it is preferred that the organic solvent is limonene. This is especially favourable because limonene is less hazardous, less harmful to health and environment than other suitable solvents. Additionally, it is also possible to use organic solvents like benzene, ethylbenzene, toluene, isoparaffin (also known as x-tra-solve (medite medizintechnik)) or any solvent with similar chemical properties or any mixture of said solvents.

A organic solvent which is suitable for washing the sample and preparing it for a better rehydratisation after dissolving paraffin is a solvent of the group of "ethanol, methanol, isopropanol or any mixture of these solvents with each other or with water". It is particularly preferred to use ethanol as a washing solvent after dissolving paraffin. Of course also additional solvents with comparable chemical properties can be used.

In an embodiment of the invention the organic solvent for dissolving paraffin is a solvent of the group "limonene, xylene or any mixture of these solvents", and wherein the washing solvent is a solvent of the group of "ethanol, methanol, isopropanol or any mixture of these solvents with each other or with water".

In a preferred embodiment of the invention the paraffin removal step comprises the addition of a suitable volume of limonene to the archived sample. The volume of limonene is thereby dependent on the amount of sample. For 1-6 10 μm sections which are typically used as a starting material (see above) 0.1-3 ml of limonene are used. A person with ordinary skills in the art will know how to adjust the volume of limonene to smaller or larger samples. After incubation, preferably for at least 5 min at 10-70° C., and centrifugation the limonene with the dissolved paraffin is removed.

In an embodiment of the invention, the paraffin removal step comprises
    addition of 0.1-3 ml of limonene to the archived sample,
    incubation for at least 5 min at 10-70° C.,
    centrifugation, and
    removal of the limonene.

In a particularly preferred embodiment 0.5-1.5 ml, preferably 1 ml, of limonene is added to the archived sample in order to remove the paraffin. Subsequently the sample is incubated with agitation for 5-120 min at 15-30° C., preferable for 10-60 min at room temperature. The agitation can be continuous or is briefly repeated several times. After centrifugation for at least 5,000×g for 1-20 min, preferably for 5 min, the tissue is located at the bottom of the tube and the mixture of limonene and paraffin is removed.

In an embodiment of the invention, the paraffin removal step comprises
    addition of 1 ml of limonene to the archived sample,
    incubation for 10 min-1 h at room temperature mixing the sample,
    centrifugation at least 5,000×g for 5 min, and
    removal of the limonene.

In a preferred embodiment of the invention the tissue sample after the removal of paraffin is washed with ethanol. If the typical amount of sample (1-6 10 μm thick sections) are used, a suitable volume of ethanol for this washing step is 0.1-3 ml. A person with ordinary skills in the art will know how to adjust this volume if smaller or larger samples are used. After the addition of ethanol, the sample is incubated at 15-30° C. for up to 10 min. But even longer incubations are possible because they are not unfavourable. After centrifugation, the ethanol is removed and the tissue sample is dryed at 15-65° C.

In an embodiment of the invention, the washing solvent is ethanol, and the embodiment comprises
    addition 0.1-3 ml of ethanol,
    optional, incubation for up to 10 min at 15-30° C.,
    centrifugation,
    removal of the ethanol, and
    drying.

In a particularly preferred embodiment, 0.5-1.5 ml preferably 1.0 ml of ethanol is added as a washing solution. The incubation takes place for 1-10 min, preferable for 10 min at room temperature with agitation. The agitation can be continuous or is briefly repeated several times. After centrifugation for at least 5,000×g for 1-20 min, preferably for 5 min, the tissue is located at the bottom of the tube and the ethanol is removed. The tissue sample is dried at 45-65° C. for 5-60 min, preferable at 50° C. for 10-30 min.

A preferred embodiment of the invention comprises the following steps:
    addition of 1 ml ethanol,
    incubation for 10 min at room temperature mixing the sample,
    centrifugation at least 5,000×g for 5 min,
    removal of the ethanol, and
    incubation for 10-30 min at 50° C.

Lysis Step

In an embodiment of the invention the lysis step is carried out by the use of protease. This protease can be a serin protease, a thiol protease, a carboxy protease, a metalloprotease, proteinase K or any mixture of these proteases.

Depending on the protease, the time for digestion may vary. The reason for this are the different activities of the proteases. According to the invention it is preferred to choose a protease with a high enzymatic activity. But according to the invention it is also preferred to choose a protease which is available at low cost. Therefore it is particularly preferred to choose a protease with a high enzymatic activity/cost ratio. Because of that it is particularly preferred to choose proteinase K for lysis.

In addition, the time for digestion varies also dependent on the texture and nature of the tissue sample. For example, tissues like breast tissue are digested rather quickly, because of the loose cohesion of the cells. On the hand, tissues like colon or liver tissue might need longer digestions because of the compactness of the tissue.

Another important factor which has an significant influence on the time of digestion is the geometrical shape of the sample. In general, samples with a large surficial area are easier digestable than samples with a smaller surficial area if they have the same texture and nature and if the same protease is used for digestion. Therefore it is preferred to use tissue sections or to cut larger tissue samples into pieces. But, according to the invention, it is also preferred to adjust the time for digestion on the geometrical shape of the tissue samples. In doing so, it is not necessary any more to cut larger tissue sections into pieces. Because this also lowers the handling effort, it is particularly preferred to use long times for digestion.

Longer digestions times are also particularly more preferred, because it is supposed that they enable a better removal of cross-linked proteins or peptides form the DNA. The importance of a complete removal of contamined protein or peptides is already explained in detail above. According to the invention, it is preferred to lyse the tissue samples with proteinase K not longer than 60 h, in particular not longer than 48 h because of efficiency reasons. This is usually sufficient for a complete digestion removing all contamined proteins and peptides.

Taken the above said into account, the minimum time of digestion is 2.5 h, preferably 3 h. This is especially the case for easy to digest tissues with have a large surficial area and the use of proteinase K.

Furthermore, for a better removal of contaminant proteins or peptides, it is particularly preferred to add an additional amount of protease after the first 24 h of digestion. This is recommended because the enzymatic activity decreases over time because of self-digestion. For some tissues it might be advantageous to add additional amounts of protease for several times. For example for colon or prostate tissue it is particularly preferred to add three times proteinase K.

In an embodiment of the invention, the lysis step is carried out by the use of a protease selected from the group "a serine protease, a thiol protease, a carboxy protease, a metalloprotease, proteinase K or any mixture of these proteases".

In a preferred embodiment the lysis step comprises the addition of 0.05-1 ml of a lysis buffer to 1-10 deparaffinated formalin-fixed tissue sections of 10 μm thickness or an equal amount of a deparaffinated formalin-fixed tissue biopsy. The lysis buffer comprises 50 mmol/l Tris(tris-hydroxymethyl-amino-methan) pH 8.0, 1 mmol/l EDTA, 0.5% Tween 20 v/v. Of course, the use of any other lysis buffer as it is known by those skilled in the art is possible. Subsequently 0.1-3 mg of proteinase K is added. Proteinase K may be dissolved in a suitable buffer, preferentially the used lysis buffer. This can be done by addition of 10-100 μl of a proteinase K solution comprising 10-30 g/l proteinase K. After the addition of the protease, the mixture is agitated. The mixture is incubated for at least 2.5 h at 40-70° C. Thereafter, if desired, the proteinase K can be inactivated by heating or by the use of inhibitors. A person with ordinary skills in the art knows how to adjust the volume of said solutions if the thickness of the section varies or if smaller or larger amount of sample are used.

In a preferred embodiment, the lysis step comprises
addition 0.05-1 ml of lysis buffer comprising 50 mmol/l tris-hydroxymethyl-amino-methan pH 8.0, 1 mmol/l EDTA, 0.5% Tween v/v to 1-10 deparaffinated formalin-fixed tissue sections or an equal amount of a deparaffinated formalin-fixed tissue biopsy,
addition a 10-100 μl of proteinase K comprising 10-30 g/l proteinase K, subsequently agitating the sample,
incubation for at least 2.5 h at 40-70° C., and
optional, inactivation of the proteinase K by heating or by use of an inhibitor.

In a particularly preferred embodiment the lysis step comprises the addition of 100-300 μl, preferably 190 μl of lysis buffer to 1-10 deparaffinated formalin-fixed tissue sections of 10 μm thickness or an equal amount of a deparaffinated formalin-fixed tissue biopsy. Furthermore 0.45-1.5 mg, preferably 0.6 mg of proteinase K are added. In particular the proteinase K is added as 15-50 μl, preferably as 20 μl of a proteinase K solution comprising 30 μg/μl proteinase K. The subsequent agitation is carried out by rigorous vortexing. After this, the mixture is incubated for 2.5-60 h at 45-65° C., preferably for 3-48 h at 50-60° C., wherein the mixture is agitated continuously or briefly repeated many times. The inactivation of the proteinase K can be achieved by incubation of the mixture for 5-20 min at least at 90° C., preferably for 10 min at least at 95° C. Storage temperaturen alle rausnehmen!!! In a especial variant it is preferred that at least 0.6 mg of proteinase K, for example 20 μl of a 30 μg/μl proteinase K solution after the first 24 h of the incubation are added. A person with ordinary skills in the art knows how to adjust the volume of said solutions if the thickness of the section varies or if smaller or larger amount of sample are used.

In a preferred embodiment, the lysis step comprises
addition of 190 μl of lysis buffer to 1-6 deparaffinated formalin-fixed tissue sections or an equal amount of a deparaffinated formalin-fixed tissue biopsy,
addition of 20 μl of proteinase K solution comprising 30 g/l proteinase K, subsequent rigorously vortexing,
incubation for 3-48 h at 50° C.-60° C. mixing the sample, and optional, addition of at least 20 μl proteinase K solution after the first 24 h incubation at 50° C.-60° C., and
incubation for 10 min at least at 95° C.

In another preferred embodiment, the archived sample is directly subjected to the lysis step which comprises the addition of 0.05-1 ml of a lysis buffer to 1-10 deparaffinated formalin-fixed tissue sections of 10 μm thickness or an equal amount of a deparaffinated formalin-fixed tissue biopsy. The lysis buffer comprises 50 mmol/l Tis(tris-hydroxymethyl-amino-methan) pH 8.0, 1 mmol/l EDTA, 0.5% Tween 20 v/v. Preferably it also comprises 5 ng/μl poly-dA DNA. Of course, other suitable lysis buffers as they are known to those skilled in the art can also be used. Subsequently the mixture is incubated for 5-20 min at 40-75° C. After this, 0.15-1.2 mg of proteinase K, for example 5-40 μl of a 30 μg/μl proteinase K solution is added. The mixture is then incubated for at least 2.5 h at 40-70° C. with agitation. Thereafter, if desired, the proteinase K can be inactivated by heating or by the use of inhibitors. A person with ordinary skills in the art knows how to adjust the volume of said solutions if the thickness of the section varies or if smaller or larger amount of sample are used.

In a preferred embodiment, the archived sample is directly subjected to the lysis step which comprises
addition of 50-1,000 μl lysis buffer to 1-10 deparaffinated formalin-fixed tissue sections or an equal amount of a deparaffinated formalin-fixed tissue biopsy, the lysis buffer pH 8.0 comprising 50 mmol/l tris-hydroxymethyl-amino-methan, 1 mmol/l EDTA, 0.5% Tween v/v, and optional 5 ng/μl poly-dA DNA,
incubation for 5-20 min at 40-75° C.,
addition of 5-40 μl proteinase K solution, the proteinase K solution comprising 30 mg/ml proteinase K,
incubation for at least 2.5 h at 40-70° C., and
optional, inactivation of the proteinase K by heating or by use of an inhibitor.

In a particularly preferred variant 75-200 μl, preferably 100 μl of lysis buffer are added to 1-6 deparaffinated formalin-fixed tissue sections of 10 μm thickness or an equal amount of a deparaffinated formalin-fixed tissue biopsy. After the addition, the mixture is incubated for 7-15 min at 50-70° C. in a thermomixer at 500-2,000 rpm, preferably for 10 min at 65° C. in a thermomixer at 1,000 rpm. Subsequently, 0.21-0.6 mg, preferably 0.3 mg of proteinase K, for example 7-20 μl, preferably 10 μl for a 30 μg/μl proteinase K solution is added. The mixture is then incubated for 2.5-60 h at 50-65° C. in a thermomixer at 1,000-2,000 rpm, preferably for 3-48 h at 60° C. in a thermomixer at 1,400 rpm. The proteinase K can be inactivated by incubation of the mixture for 5-20 min at least at 90° C., preferably for 10 min at least at 95° C. The inactivation of proteinase K can also be achieved by the addition of proteinase K inhibitors. A person with ordinary skills in the art knows how to adjust the volume of said solutions if the thickness of the section varies or if smaller or larger amount of sample are used.

In a particularly preferred embodiment, the lysis step comprises
addition of 100 μl lysis buffer to 1-6 deparaffinated formalin-fixed tissue sections or an equal amount of a deparaffinated formalin-fixed tissue biopsy,
incubation for 10 min at 65° C. in a thermomixer at 1,000 rpm,
incubation at 50° C. in a thermomixer at 1,400 rpm addition of 10 µl proteinase K solution,
incubation for 3-48 h at 60° C. in thermomixer at 1,000 rpm, and
incubation for 10 min at >95° C.

In case the archived sample is directly subjected to the lysis step, it is preferred that the DNA may be directly subjected to the bisulfite treatment leaving out the DNA extraction step. This is in particular preferred if the amount of archived sample is small or if a person with ordinary skills in the are would expect only small yields of DNA.

DNA Extraction Step

A lot of methods are known to those skilled in the art for DNA extraction from tissue samples (Sambrook et al., Molecular Cloning: A Laboratory Manual, $2^{nd}$ edition, 1989, Cold Spring Harbor Laboratory Press).

To reduce the handling effort and also to ensure a high reproducibility as well as reliability, it is preferred to use a kit for DNA extraction. For one with ordinary skills in the art a high amount of kits are known which might be suitable for DNA extraction.

Therefore in a first step the most promising kits were chosen for subsequent tests. These kits are: QIAAMP® DNA Mini Kit, ZR GENOMIC™ DNA II kit, MAGNASIL® Genomic, Fixed Tissue System, MAGNA-PURE™ LC DNA Isolation Kit II (Tissue), Nexttec tissue kit, CHARGE SWITCH® Forensic DNA Purification Kit, and CHARGE SWITCH® genomic DNA Purification kit.

In a second step these kits were tested in view of a DNA extraction, wherein the following criteria were used: i) a minimal handling effort; ii) a minimal length of time; iii) yield of DNA; iv) the ability of amplification after the extraction step; and v) purity of the DNA by means of UV light (260 nm/280 nm ratio preferably in the range of 1.7-1.9). The QIAAMP® DNA Mini Kit was used as a reference. Best results were just obtained by the QIAAMP® DNA Mini Kit.

Therefore, according to the invention and for best results, the QIAAMP® DNA Mini Kit is preferably used. In addition, also kits are preferably used which contain the same solutions and/or equivalent materials such as columns or buffers. Such kinds of kits are for example the DNEASY® 96 Tissue Kit, the QIAAMP® 96 DNA Blood Kit, the QIAAMP® DSP 96 Virus MDX Kit, the DNEASY® Tissue Kit, the QIAAMP® DNA Micro Kit, QIAAMP® Viral RNA Mini kit or the QIAAMP® DSP Virus Kit (all QIAGEN®).
QIAGEN®

In an embodiment of the invention the DNA extraction step is characterized in that the DNA to be extracted binds to silica surfaces, in particular to silica membranes.

In an embodiment, the DNA extraction step is characterized by a binding of DNA to silica surfaces, in particular to silica membranes.

It is particularly preferred that the DNA extraction step is carried out by means of the DNEASY® 96 Tissue Kit, the QIAAMP® 96 DNA Blood Kit, the QIAAMP® DSP 96 Virus MDX Kit, the DNEASY® Tissue Kit, the QIAAMP® DNA Mini Kit, or the QIAAMP® DNA Micro Kit, the QIAAMP® Viral RNA Mini or the QIAAMP® DSP Virus Kit (all QIAGEN®).

In principle also other kits are useable according to the invention as long as they lead to similar results. Those kits are for example kits which are based on the "charge-switch"-technology (Invitrogen) or the "nexttec"-technology (nexttec GmbH). These can be the Nexttec tissue kit, the ChargeSwitch® Forensic DNA Purification Kit, and the CHARGE SWITCH® genomic DNA Purification kit.

In an embodiment one or more of the following kits are used in the DNA extraction step: DNEASY® 96 Tissue Kit, QIAAMP® 96 DNA Blood Kit, QIAAMP® DSP 96 Virus MDX Kit, DNEASY® Tissue Kit, QIAAMP® DNA Mini Kit, QIAAMP® DNA Micro Kit, QIAAMP® Viral RNA Mini or the QIAAMP® DSP Virus Kit.

In embodiments of the invention the binding buffer AL is replaced by the binding buffers ATL or AVL. A person with ordinary skills in the art knows how to adjust the method of the invention accordingly. The buffers ATL and AVL can also be premixed like the buffer AL with ethanol as known to those skill in the art. Therefore, in embodiments of the invention, the binding buffer AL/E is replaced by the binding buffers ATL/E or AVL/E. A person with ordinary skills in the art knows how to adjust the method of the invention accordingly.

In an especially preferred embodiment, the DNA extraction step is carried out according to the DNEASY® 96 Tissue Kit or the QIAAMP® 96 DNA Blood Kit. Also the QIAAMP® DSP 96 Virus MDx Kit can be used if only small amounts of DNA are expected. According to this embodiment, 100-600 µl of the binding buffer AL/E, ATL/E or AVL/E (QIAGEN®) are added to the mixture derived from the lysis step. The lysate is derived from 1-10 deparaffinated formalin-fixed tissue sections of 10 µm thickness or an equal amount of a deparaffinated formalin-fixed tissue biopsy. After agitation, the mixture is applied onto a column of a plate of the DNEASY® 96 Tissue Kit, the QIAAMP® 96 DNA Blood Kit or the QIAAMP® DSP 96 Virus MDX Kit (all QIAGEN®). The column is washed with the buffers AW1 (QIAGEN®) and AW2 (QIAGEN®), before the DNA is eluted by 20-200 µl of elution buffer. The elution buffer can be AE, AVE or EB (all QIAGEN®) or water. Typically the elution buffer is adjusted to 15-80° C. After the addition of the preheated elution buffer, the column is incubated for at least 30 s at 15-40° C., before it is centrifugated. The flow-through of the column contains the DNA to be extracted. A person with ordinary skills in the art knows how to adjust the volume of the solutions if the thickness of the section varies or if smaller or larger amount of sample are used.

In an embodiment, the DNA extraction step is carried out according to the DNEASY® 96 Tissue Kit, the QIAAMP® 96 DNA Blood Kit or the QIAAMP® DSP 96 Virus MDx Kit comprising
addition of 100-600 µl of binding buffer AL/E, ATL/E or AVL/E to a lysate derived from 1-10 deparaffinated formalin-fixed tissue sections or an equal amount of a deparaffinated formalin-fixed tissue biopsy,
application of the mixture onto a plate,
washing with washing buffer AW1 and AW2, and
elution by addition of 20-200 µl elution buffer AE, AVE, EB or water adjusted to 15-80° C., incubation for at least 30 s at 15-40° C., and centrifugation.

According to this embodiment it is particularly more preferred, that 300-500 µl of binding buffer AL/E, ATL/E or AVL/E are added to 100-300 µl of lysate derived from to 1-6 deparaffinated formalin-fixed tissue sections of 10 µm thickness or an equal amount of a deparaffinated formalin-fixed tissue biopsy, preferably 400 µl of binding buffer AL/E are added to 200 µl of lysate. The shaking is performed by shaking with both hands for 10-30 s, preferably for 15 s. After application of the mixture onto a column of a plate, the plate is centrifuged for 5-20 min at 4,000-6500×g, preferably for 10 min at 5,790×g. The washing with the buffers AW1 and AW2, respectively, is carried out by application of 300-700 µl, preferably of 500 µl of washing buffer followed by a centrifugation for 5-20 min at 4,000-6500×g, preferably for 10 min at 5,790×g. After the washing steps the columns of a plate are dried by centrifugation for 10-30 min at 4,000-6,500×g, preferably for 15 min at 5,790×g. The DNA is eluted by addition of 90-150 µl, preferably of 120 µl of elution buffer preheated to 50-75° C., preferably to 70° C., followed by an incubation for 1-20 min at 17-30° C., preferably for 5 min at room temperature, and a subsequent centrifugation for 1-10 min at 4,000-6,500×g, preferably for 2 min at 5,790×g. The flow-through of the column containing the DNA can be stored +4° C. to −80° C. A person with ordinary skills in the art knows how to adjust the volume of the solutions if the thickness of the section varies or if smaller or larger amount of sample are used.

In an embodiment, the DNA extraction step comprises
addition of 400 µl of binding buffer AL/E, ATL/E or AVL/E to 200 µl lysate derived from 1-6 deparaffinated formalin-fixed tissue sections or an equal amount of a deparaffinated formalin-fixed tissue biopsy
shaking for 15 s with both hands
application of the mixture onto a plate,
centrifugation for 10 min at 5790×g
application of 500 µl washing buffer AW1 and subsequent centrifugation at 5,790×g for 5 min,
application of 500 µl washing puffer AW2 and subsequent centrifugation at 5,790×g for 5 min,
drying of the column by centrifugation at 5,790×g for 15 min, and
elution by addition of 120 µl elution buffer AE, AVE or EB or water preheated to 70° C., incubation for 5 min at room temperature and centrifugation for 2 min at 5,790×g.

In a further especially preferred embodiment, the DNA extraction step is carried out according to the DNEASY® Tissue Kit, the QIAAMP® DNA Mini Kit or the QIAAMP® DNA Micro Kit. Also the QIAAMP® Viral RNA Mini or the QIAAMP® DSP Virus Kit can be used if only small amounts of DNA are expected. According to this embodiment, 150-300 µl of the binding buffer AL, ATL or AVL (QIAGEN®) are added to the lysate derived from to 1-6 deparaffinated formalin-fixed tissue sections of 10 µm thickness or an equal amount of a deparaffinated formalin-fixed tissue biopsy. The mixture is incubated for at least 5 min at 45° C.-80° C. with agitation. Subsequently, 150-300 µl of ethanol are added, after which the sample is agitated, centrifuged and applied onto a column of the DNEASY® Tissue Kit, the QIAAMP® DNA Mini Kit, the QIAAMP® DNA Micro Kit, the QIAAMP® Viral RNA Mini, or the QIAAMP® DSP Virus Kit. After centrifugation, the column is washed with the washing buffers AW1 and AW2. To dry the column it is favourable to centrifuge the column, but this is not necessary. The DNA is eluted from the column by applying in one or two elution steps up to 180 µl of elution buffer onto the column. The elution buffer can be AE, AVE or EB (all QIAGEN®) or water adjusted to room temperature. Of course other similar buffers are also suitable as long as do not interfere with the subsequent steps. After addition of the elution buffer, the column is incubated at room temperature, before it is centrifuged. The flow-through of the column contains the DNA to be extracted. A person with ordinary skills in the art knows how to adjust the volume of the solutions if the thickness of the section varies or if smaller or larger amount of sample are used.

In a particular embodiment, the DNA extraction step is carried out by means of a MINELUTE™ column. These columns are for example part of the QIAAMP® DNA Micro Kit. Very surprisingly, DNA eluted in the first step of the elution of extracted DNA from these columns results in better ability of amplification. As already mentioned above, the use of a MINELUTE™ column improves the ability of amplification if a bisulfite treatment step and subsequent DNA purification step is carried out or not.

In an embodiment, the DNA extraction step is carried out according to the DNEASY® Tissue Kit, the QIAAMP® DNA Mini Kit, the QIAAMP® DNA Micro Kit, the QIAAMP® Viral RNA Mini, or the QIAAMP® DSP Virus Kit comprising
addition of 150-300 µl of binding buffer AL, ATL or AVL to the lysate derived from 1-6 deparaffinated formalin-fixed tissue sections or an equal amount of a deparaffinated formalin-fixed tissue biopsy,
incubation for at least 5 min at 45° C.-80° C. agitating the sample,
addition of 150-300 µl of ethanol, subsequently agitating the sample and centrifugation,
application of the mixture onto a column,
centrifugation,
washing with washing puffer AW1 and AW2,
optional, centrifugation, and
elution in one or two steps by addition of up to 180 µl elution buffer AE, AVE or EB or water adjusted to room temperature, incubation at room temperature and centrifugation.

According to this embodiment it is particularly more preferred, that 175-250 µl of binding buffer AL are added to 175-250 µl of lysate, preferable 200-210 µl of binding buffer AL, ATL or AVL are added to 210 µl of lysate derived from 1-6 deparaffinated formalin-fixed tissue sections of 10 µm thickness or an equal amount of a deparaffinated formalin-fixed tissue biopsy. The mixture is incubated for 5-25 min at 50° C.-75° C. with agitation, preferably for 10 min at 56° C.-70° C. with agitation. Subsequently, 175-250 µl, preferably 200-210 ml of ethanol are added, after which the sample is agitated by pulse-vortexing for 15 s, and centrifuged for 1-20 s at 1,000-14,000×g, preferably for 5 s at 5,000×g. The mixture is then added on a column of the DNEASY® Tissue Kit, the QIAAMP® DNA Mini Kit, the QIAAMP® DNA Micro Kit, the QIAAMP® Viral RNA Mini, or the QIAAMP® DSP Virus Kit. Subsequently the columns are centrifuged for 0.5-10 min at 4,000-8,000×g, preferably for 1 min at 6,000×g. The washing with the buffers AW1 is carried out by application of 300-700 µl, preferably of 500 µl of AW1 followed by a centrifugation for 0.5-10 min at 4,000-8,000×g, preferably for 1 min at 6,000×g. Subsequently, the washing with the buffers AW2 is carried out by application of 300-700 µl, preferably of 500 µl of AW2 followed by a centrifugation for 1-10 min at 15,000-25,000×g, preferably for 3 min at 20,000×g. To dry the column it is favourable to centrifuge the column for 0.5-5 min at 15,000-25,000×g, preferably for 1 min at 20,000×g, but this is not necessary. The DNA is eluted from the column by applying 20-150 µl, preferably 35-120 µl of elution buffer onto the column. The elution buffer can be AE, AVE or EB (all QIAGEN®) or water adjusted to room temperature. After addition of the elution buffer, the column is incubated at room temperature for 0.5-15 min, preferably for 1-5 min. The column is then centrifuged for 0.5-10 min at 4,000-8,000×g, preferably for 1 min at 6,000×g. The flow-through of the column contains the DNA to be extracted. Although it is not necessary, it is favourable to carry out a second elution step, wherein 20-80 µl, preferably 35-60 µl of elution buffer are added onto the column. The elution buffer can be AE, AVE or EB (all QIAGEN®) or water adjusted to room temperature. After addition of the elution buffer, the column is incubated at room temperature for 0.5-15 min, preferably for 1-5 min. The column is then centrifuged for 0.5-10 min at 4,000-8,000×g, preferably for 1 min at 6,000×g. The flow-through of the column is combined with the flowthrough of the first elution step and can be stored at 0° C.-10° C., preferably at 4° C. for no more than 2 days. If a longer storage is intended, a the flow-through is stored at −20° C. to −80° C. A person with ordinary skills in the art knows how to adjust the volume of the solutions if the thickness of the section varies or if smaller or larger amount of sample are used.

In an embodiment, the DNA extraction step comprises
a) addition of 200-210 μl of binding buffer AL, ATL or AVL to 210 μl lysate derived from 1-6 deparaffinated formalin-fixed tissue sections or an equal amount of a deparaffinated formalin-fixed tissue biopsy,
b) incubation for 10 min at 56° C.-70° C. mixing the sample,
c) addition of 200-210 μl of ethanol, pulse-vortexing for 15 s and centrifugation for 5 s at 5,000×g,
d) application of the mixture onto a column,
e) centrifugation for 1 min at 6,000×g
f) application of 500 μl washing puffer AW1 and subsequent centrifugation at 6,000×g for 1 min
g) application of 500 μl washing buffer AW2 and subsequent centrifugation at 20,000×g for 3 min,
h) optional, centrifugation at 20,000×g for 1 min using new tubes, and
i) elution by a first addition of 35-120 μl elution buffer AE, AVE or EB or water adjusted to room temperature, incubation for 1-5 min at room temperature and centrifugation for 1 min at 6,000×g, and an optional second addition of 35-60 μl elution buffer AE, AVE or EB or water adjusted to room temperature, incubation for 1-5 min at room temperature and centrifugation for 1 min at 6,000×g.

An alternative to the last embodiment is a variant, wherein it is favourable to dry the column after the washing step with buffer AW2 by beating the column on a kleenex tissue on the bench with a subsequent centrifugation for 0.5-10 min at 4,000-8,000×g, preferably for 1 min at 6,000×g. After this the elution is carried out by applying 25-200 μl, preferably of 50-150 μl of elution buffer onto the column. The elution buffer can be AE, AVE or EB (all QIAGEN®) or water preheated to 30-50° C., preferably to 40° C. After addition of the elution buffer, the column is incubated at room temperature for 0.5-15 min, preferably for 1-5 min. The column is then centrifuged for 0.5-10 min at 4,000-8,000×g, preferably for 1 min at 6,000×g. The flow-through containing DNA is again applied onto the same column. After the addition, the column is incubated at room temperature for 0.5-5 min, preferably for 1 min. The column is then centrifuged for 0.5-10 min at 4,000-8,000×g, preferably for 1 min at 6,000×g. This proceeding has the advantage that a higher recovery of DNA can be eluted from the column not extending the elution buffer. A person with ordinary skills in the art knows how to adjust the volume of the solutions if the thickness of the section varies or if smaller or larger amount of sample are used.

In a particular embodiment, steps h) and i) of the DNA extraction step are replace by the following steps k) and l), respectively:
k) optional, beating the column on a kleenex tissue on the bench with a subsequent centrifugation at 6,000×g for 1 min,
l) elution by addition of 50-150 μl of buffer AE or water preheated to 40° C., incubation for 1-5 min at room temperature, centrifugation at 6,000×g for 1 min, repeated application of this first eluate onto the column, incubation for 1 min at room temperature and centrifugation at 6,000×g for 1 min.

Bisulfite Treatment Step

In an embodiment the bisulfite treatment step is essentially carried out as described in WO05/038051 (this reference is incorporated by its entirety). According to this, in one embodiment DNA is reacted with a bisulfite reagent, characterized in that said reaction is carried out in the presence of a compound out of the group of dioxane, one of its derivatives and a similar aliphatic cyclic ether.

In another embodiment DNA is reacted with a bisulfite reagent, characterized in that said reaction is carried out in the presence of a compound of the following formula:

n = 1-35000
m = 1-3
R1 = H, Me, Et, Pr, Bu
R2 = H, Me, Et, Pr, Bu

Preferred are thus n-alkylene glycol compounds, particularly their dialkyl ethers, and especially diethylene glycol dimethyl ether (DME).

The bisulfite conversion may take place both in solution as well as also on DNA bound to a solid phase. Preferably sodium disulfite (=sodium bisulfite/sodium metabisulfite) is used, since it is more soluble in water than sodium sulfite. The disulfite salt disproportionates in aqueous solution to the hydrogen sulfite anions necessary for the cytosine conversion. When bisulfite concentration is discussed below, this refers to the concentration of hydrogen sulfite and sulfite anions in the reaction solution. For the method according to the invention, concentration ranges of 0.1 to 6 mol/l are possible. Particularly preferred is a concentration range of 1 to 6 mol/l, and most particularly preferred, 2-4 mol/l. However, when dioxane is used, the maximal concentration of bisulfite that can be used is smaller (see below). In selecting the bisulfite concentration, one must consider that a high concentration of bisulfite leads to a high conversion, but also leads to a high decomposition rate due to the lower pH.

Dioxane can be utilized in different concentrations. Preferably, the dioxane concentration amounts to 10 to 35% (vol/vol), particularly preferred is 20 to 30%, and most particularly preferred is 22 to 28%, especially 25%. A dioxane concentration higher than 35% is problematic, since this results in a formation of two phases within the reaction solution. In the particularly preferred embodiments with a dioxane concentration of 22-28%, the final preferred bisulfite concentration amounts to 3.3 to 3.6 mol/l, and in the most particularly preferred embodiment with a dioxane concentration of 25%, it amounts to 3.5 mol/l (see Examples).

The n-alkylene glycol compounds according to the invention can be utilized in a different concentration range. DME is preferably used in concentrations between 1-35% (vol/vol). There is preferably between 5 and 25%, and most preferably 10% DME.

The preferred scavengers utilised according to the invention are chromane derivatives, e.g., 6-hydroxy-2,5,7,8,-tetramethylchromane 2-carboxylic acid (also known as: Trolox-C™). Further scavengers are listed in the patent application WO 01/98528 (=DE 100 29 915; =U.S. application Ser. No. 10/311,661; incorporated herein in its entirety).

The bisulfite conversion can be conducted in a wide temperature range from 0 to 95° C. However, as at higher temperatures the rates of both the conversion and decomposition of the DNA increase, in a preferred embodiment the reaction temperature lies between 0-80° C., preferably between 30-80° C. Particularly preferred is a range between 50-70° C.; most particularly preferred between 57-65° C. The optimal reaction time of the bisulfite treatment depends on the reaction temperature. The reaction time normally amounts to between 1 and 18 hours (see: Grunau et al. 2001, Nucleic Acids Res. 2001, 29(13):E65-5; incorporated by reference herein in its entirety). The reaction time is ordinarily 4-6 hours for a reaction temperature of 60° C.

In a particularly preferred embodiment of the method according to the invention, the bisulfite conversion is conducted at mild reaction temperatures, wherein the reaction temperature is then clearly increased for a short time at least once during the course of the conversion. In this way, the effectiveness of the bisulfite conversion can be surprisingly clearly be increased. The temperature increases of short duration are named "thermospikes" below. The "standard" reaction temperature outside the thermospikes is denoted as the basic reaction temperature. The basic reaction temperature amounts to between 0 and 80° C., preferably between 30-80° C., more preferably between 50-70° C., most preferably between 57-65° C., as described above.

The reaction temperature during a thermospike is increased to over 85° C. by at least one thermospike. The optimal number of thermospikes is a function of the basic reaction temperature. The higher the optimal number of thermospikes is, the lower is the basic reaction temperature. At least one thermospike is necessary in each case. And, on the other hand, in principle, any number of thermospikes is conceivable. Of course, it must be considered that with a large number of temperature increases, the decomposition rate of the DNA also increases, and an optimal conversion is no longer assured. The preferred number of thermospikes is thus between 1 and 10 thermospikes each time, depending on the basic reaction temperature. A number of two to 5 thermospikes is thus particularly preferred. The thermospikes increase the reaction temperature preferably to 85 to 100° C., particularly preferably to 90-100° C., and most preferably to 94° C.-100° C.

The duration in time of the thermospikes also depends on the volume of the reaction batch. It must be assured that the temperature is increased uniformly throughout the total reaction solution. For a 20 µl reaction batch when using a thermocycler a duration between 15 seconds and 1.5 minutes, especially a duration between 20 and 50 seconds is preferred. In a particular preferred embodiment the duration is 30 seconds. Operating on a volume of 100 µl the preferred range lies between 30 seconds and 5 minutes, especially between 1 and 3 minutes. Particularly preferred are 1.5-3 minutes. For a volume of 600 µl, a duration of 1 to 6 minutes, is preferred, especially between 2 and 4 minutes. Particularly preferred is a duration of 3 minutes. A person skilled in the art will easily be able to determine suitable durations of thermospikes in relation to a variety of reaction volumes. The above-described use of thermospikes leads to a significantly better conversion rates in the bisulfite conversion reaction, even when the above-described denaturing solvents are not utilized.

In a preferred variant 10-60 µl of the solution containing the extracted genomic DNA is mixed with 50-120 µl of bisulfite solution. The bisulfite solution has a pH in the range of 4.7 to 6.5, preferably in the range of 5.0 to 6.0, and particularly preferred in the range of 5.45 to 5.50. The bisulfite solution comprises hydrogensulfite in a concentration of 3.5-6.0, preferably in the range of 4.4-5.3, and particularly preferred in a concentration of 4.83-4.93 mol/l. For Example, such kind of bisulfite solution can be obtained by adding 4.708 g of sodium disulfite and 1.128 g of sodium sulfite to 10 ml of water. After dissolving of the salts, the final volume is about 12 ml. To the mixture of genomic DNA solution and the bisulfite solution 8-45 µl of an organic radical scavenger solution is added. The organic radical scavenger solution comprises an organic solvent and 50-1.000 mmol/l, preferably 100-750 mmol/l, and particularly preferred 158-500 mmol/l of the radical scavenger 6-hydroxy-2,5,7,8-tetramethyl-chroman-2-carboxylic acid or any other suitable radical scavenger. After the addition of the radical scavenger solution, a temperature protocol is applied for 3-8 h. The protocol is characterized in that the reaction is conducted in a temperature range of 0-80° C. with additional 2-5 temperature increases (thermospikes) for 1-10 min to 85-100° C. including an initial temperature increase (thermospike) to 85-100° C.

In an embodiment, the bisulfite treatment step comprises
  mixing of 10-60 µl of the solution containing the genomic DNA with 50-120 µl of bisulfite solution, the bisulfite solution having a pH in the range of 5.45 to 5.50 comprising 4.83-4.93 mol/l hydrogensulfite,
  addition of 8-45 µl of an organic radical scavenger solution, the organic radical scavenger solution comprising an organic solvent and 158-500 mmol/l 6-hydroxy-2,5,7,8-tetramethyl-chroman-2-carboxylic acid, and
  applying a temperature protocol for 3-8 h, characterized in that the reaction is conducted in a temperature range of 0-80° C. with additional 2-5 temperature increases for 1-10 min to 85 to 100° C. including an initial temperature increase to 85-100° C.

In a particularly preferred embodiment the bisulfite step is carried out as described in the following: 44-50 µl of a solution containing the extracted genomic DNA are mixed with 83-95 µl of a bisulfite solution. The bisulfite solution has a pH in the range of 5.45 to 5.50 and comprises hydrogensulfite in a concentration of 4.83-4.93 mol/l. For Example, such kind of bisulfite solution can be obtained by adding 4.708 g of sodium disulfite and 1.128 g of sodium sulfite to 10 ml of water. After dissolving of the salts, the final volume is about 12 ml. After the addition of the bisulfite solution 13-15 µl of a DME solution are added, the DME solution comprising 250-1.000 mmol/l, preferably 350-750 mmol/l, and particularly preferred 500 mmol/l 6-hydroxy-2,5,7,8-tetramethyl-chroman-2-carboxylic acid dissolved in diethyleneglycoldimethylether (DME). Thereafter a temperature protocol is applied for 4-7 h. The protocol is characterized in that the reaction is conducted in a temperature range of 57-65° C. with additional 2-5 temperature increases (thermospikes) for 3-5 min to 94-100° C. including an initial temperature increase (thermospike) to 94-100° C.

In an preferred embodiment, the bisulfite treatment step comprises
  mixing of 44-50 µl of solution containing the genomic DNA with 83-95 µl of the bisulfite solution
  addition of 13-15 µl of DME solution, the DME solution comprising 500 mmol/l 6-hydroxy-2,5,7,8-tetramethyl-chroman-2-carboxylic acid dissolved in diethyleneglycoldimethylether, and
  applying a temperature protocol for 4-7 h, characterized in that the reaction is conducted in a temperature range of 57-65° C. with additional 2-5 temperature increases for 3-5 min to 94-100° C. including an initial temperature increase to 94-100° C.

In another particularly preferred embodiment 15-20 µl of solution containing the isolated genomic DNA is mixed with 60-85 µl of a bisulfite solution. The bisulfite solution has a pH in the range of 5.45 to 5.50 and comprises hydrogensulfite in a concentration of 4.83-4.93 mol/l. After the addition of the bisulfite solution 25-35 µl of dioxane solution is added. The dioxane solution comprises 50-500 mmol/l, preferably 75-300 mmol/l, and particularly preferred 158 mmol/l 6-hydroxy-2,5,7,8-tetramethyl-chroman-2-carboxylic acid dissolved in 1,4-dioxane. Thereafter a temperature protocol is applied for 4-7 h. The protocol is characterized in that the reaction is conducted in a temperature range of 57-65° C. with additional 2-5 temperature increases (thermospikes) for 3-5 min to 94-100° C. including an initial temperature increase (thermospike) to 94-100° C.

In a preferred embodiment, the bisulfite treatment step comprises
- mixing of 15-20 µl of solution containing the genomic DNA with 60-85 µl of the bisulfite solution,
- addition of 25-35 µl of dioxane solution, the dioxane solution comprising 158 mmol/l 6-hydroxy-2,5,7,8-tetramethyl-chroman-2-carboxylic acid dissolved in 1,4-dioxane,
- applying a temperature protocol for 4-7 h, characterized in that the reaction is conducted in a temperature range of 57-65° C. with additional 2-5 temperature increases for 3-5 min to 94-100° C. including an initial temperature increase to 94-100° C.

DNA Purification Step

After the bisulfite conversion is completed, the DNA is desulfonated and purified. Different methods are known for this purpose (e.g., see: DE 101 54 317 A1=U.S. Ser. No. 10/416,624; Grunau et al. 2001, loc. cit.). Normally, the reaction solution is first treated with sodium hydroxide. Subsequently a neutralization and alcohol precipitation of the DNA are carried out.

In a preferred embodiment of the above-described embodiments according to the invention, the purification is performed by means of a gel filtration, e.g., with Sephadex-G25 columns or with Sephadex-G50 columns. The bisulfite salt can be removed very effectively in this way, without the need for further washing steps. In a second preferred embodiment, the purification is conducted via DNA-binding surfaces, e.g., via the WIZARD® DNA purification resin of Promega (see: Kawakami et al., Journal of the National Cancer Institute, Vol. 92, No. 22, 2000, pp. 1805-11). A third preferred embodiment utilizes magnetic particles for purification, e.g., with the help of the MAGNA-PURE™ process. These purification methods lead to particularly good results in combination with the n-alkylene glycol compounds according to the invention, particularly with DME. The purification is conducted according to the manufacturer's instructions. It is known to the person skilled in the art that an even further increased yield may be attainable by variation of the manufacturer's instructions by using standard experiments. Correspondingly, optimized protocols are also part of this invention. Further technical instructions for purifying nucleic acids via gel filtration, DNA-binding surfaces and magnetic particles are known to the person skilled in the art and are provided, e.g., from the manufacturer's instructions.

In a most particularly preferred embodiment, purification is conducted by means of an ultrafiltration. Such a procedure has several technical advantages and results in a surprisingly successful purification of the converted DNA. The recovery rate of the converted DNA which was initially derived from an archieved sample is very high (>25%). Ultrafiltration also has other advantages. For instance, purification is very flexible with respect to the volume of the samples to be used. In addition, the bisulfite salts can be removed almost completely. Furthermore, a desulfonation can be performed on the filter membrane, which additionally results in a savings in time.

Different commercially available ultrafiltration systems are known to the person skilled in the art, which may be used for the method according to the invention. In a preferred embodiment, Microcon™ columns of MILLIPORE® are used.

It is known to the person skilled in the art that other procedures may be indicated with other ultrafiltration systems, and that a good yield can also be obtained by varying the above-indicated conditions. The corresponding embodiments are also part of this invention.

In addition bisulfite treated DNA can also be purified according to the invention by means of the ability of DNA to bind to silica surfaces, in particular to silica membranes. Because of their high reliability and reproducability and also to reduce the handling effort silica based kits are preferred. For one with ordinary skills in the art a high amount of kits are known which might be suitable for bisulfite treated DNA purification.

Therefore, in a first step the most promising kits were chosen. These kits are: QIAAMP® Viral RNA Mini, ZYMO-SPIN™ IC columns in combination with buffer supplied with the QIAAMP® Viral RNA Mini kit, STRATAPREP® PCR purification, AUTOSEQ® G50, MICROSPIN™ G25, ChargeSwitch® Forensic DNA Purification Kit, and CHARGE SWITCH® genomic DNA Purification kit. In a second step these kits were test according to the following criteria: i) a minimal handling effort; ii) a minimal length of time; iii) yield of DNA; and iv) concentration of sulfite in the DNA solution after purification. As a reference, the purification by means of a Microcon™ device (example 2d) was used. Comparably good results as by means of a Microcon™ device were just obtained with the QIAAMP® Viral RNA Mini kit.

In addition, also kits are preferably used which contain the same solutions and/or equivalent materials such as columns or buffers. These kits are the DNEASY® 96 Tissue Kit, the QIAAMP® 96 DNA Blood Kit, the QIAAMP® DSP 96 Virus MDX Kit, the DNEASY® Tissue Kit, the QIAAMP® DNA Mini Kit, the QIAAMP® DNA Micro Kit, the QIAAMP® Viral RNA Mini or the QIAAMP® DSP Virus Kit (all QIAGEN®). These kits are all based on binding of DNA to silica surfaces.

For purification after the bisulfite treatment, the manufacturer's instructions are each amended in preferred embodiments by addition of an alkaline hydrolytic step. This alkaline hydrolytic step is carried out by incubation with an alkaline solution comprising a high content of an alcohol. According to the invention the alkaline solution comprises sodium hydroxide or any other hydroxides with similar chemical properties like potassium hydroxide or any mixture of these as well as ethanol or any other alcohol with similar chemical properties like isopropanol or any mixture of these. In particular, it is preferred that the alkaline solution comprises sodium hydroxide and ethanol. It is especially preferred that the concentration of sodium hydroxide is in the range of 0.1-0.3 mol/l, preferably 0.15-0.25 mol/l, and particularly preferred 0.2 mol/l, while the content of ethanol is in the range of 60-95%, preferably 75-93%, and particularly preferred 90%. According to the invention, the recovery rate of converted DNA is as good as the recovery rate obtained with Microcon™ devices (>25%).

According to the invention also other kits may be used, for example other kits which are based on DNA binding to silica surfaces, in particular to silica membranes. In principle also other kits are useable as long as they lead to similar results. Those kits are for example kits which are based on the "charge-switch"-technology (Invitrogen). These can be the ChargeSwitch® Forensic DNA Purification Kit, and CHARGE SWITCH® genomic DNA Purification kit.

According to the invention, the DNA purification step follows the bisulfite treatment step. In case the bisulfite treatment step is not carried out, this purification step might be dispensible and therefore it is not necessary according to the invention to carry out this step.

In a preferred embodiment of the invention the purification step is carried out by means of the DNEASY® 96 Tissue Kit, the QIAAMP® 96 DNA Blood Kit, the DNEASY® Tissue Kit, the QIAAMP® DNA Mini Kit, and the QIAAMP® DNA Micro Kit. Also the QIAAMP® DSP 96 Virus MDx Kit, QIAAMP® Viral RNA Mini or the QIAAMP® DSP Virus Kit can be used. These kits are favourable in case only small amounts of DNA are expected. According to the invention also devices and solutions of other kits can be used if they lead to similar results regarding the quality and quantity of purificated DNA. For example, this can be devices and solutions of kits which are based on the "charge-switch"-technology (invitrogen). According to this embodiment, the bisulfite treated sample is mixed with 500-620 μl binding buffer, the binding buffer comprising 1-50 ng/μl, preferably 5-25 ng/μl, particularly preferred 10 ng/μl RNA or a comparable amount of any nucleic acid dissolved in the buffer AVL. After this 500-620 μl of ethanol are added. The mixture is then incubated at 0-37° C. for 5-20 min, before it is applied onto a column of a plate of the DNEASY® 96 Tissue Kit, the QIAAMP® 96 DNA Blood Kit, or the QIAAMP® DSP 96 Virus MDx Kit or onto a column of the DNEASY® Tissue Kit, the QIAAMP® DNA Mini Kit, the QIAAMP® DNA Micro Kit, the QIAAMP® Viral RNA Mini, the QIAAMP® DSP Virus Kit. In any case the DNA binds to a column. Thereafter the column is washed with 300-1,000 μl washing buffer AW1. This is followed by an alkaline hydrolysis, wherein 450-550 μl of a solution containing 0.2 mol/l sodium hydroxide and 90% ethanol is applied for 10-25 min at 15-26° C. to the column and therewith to the DNA. Afterwards the column is washed with 300-1,000 μl of washing buffer AW2, before the DNA is eluted form the column by addition of 50-150 μl of one of the elution buffers AE, AVE, EB oder water.

It is also possible to carry out the purification step with a binding buffer comprising not any RNA or any comparable amount of any nucleic acid. Corresponding embodiments are also part of the invention.

In an embodiment of the invention, the purification step is carried by means of the DNEASY® 96 Tissue Kit, the QIAAMP® 96 DNA Blood Kit, the QIAAMP® DSP 96 Virus MDx Kit, the DNEASY® Tissue Kit, the QIAAMP® DNA Mini Kit, the QIAAMP® DNA Micro Kit, the QIAAMP® Viral RNA Mini, the QIAAMP® DSP Virus Kit, comprising mixing of the bisulfite treated sample with 500-620 μl binding buffer, optionally the binding buffer containing 10 ng/μl RNA dissolved in the buffer AVL, addition of 500-620 μl ethanol, incubation at 0-37° C. for 5-20 min, binding of the DNA onto a plate of the DNEASY® 96 Tissue Kit, the QIAAMP® 96 DNA Blood Kit, or the QIAAMP® DSP 96 Virus MDx Kit or onto a column of the DNEASY® Tissue Kit, the QIAAMP® DNA Mini Kit, the QIAAMP® DNA Micro Kit, the QIAAMP® Viral RNA Mini, the QIAAMP® DSP Virus Kit, washing with 300-1,000 μl washing buffer AW1, treatment with 450-550 μl of a solution containing 0.2 mol/l sodium hydroxide and 90% ethanol for 10-25 min at 15-26° C., washing with 300-1,000 μl washing buffer AW2, elution with 50-150 μl of one of the elution buffers AE, AVE, EB oder water.

In a particularly preferred embodiment 100-200 μl of bisulfite treated sample is mixed with 520-600 μl binding buffer AVL optionally comprising 10 ng/μl RNA, preferably 140 μl of bisulfite treated sample is mixed with 560 μl of binding buffer. After this 520-600 μl, preferably 560 μl of ethanol are added. The mixture is then centrifuged at 750-2000×g at least for 1 s, preferably at 1.450×g for 1 s. After this it is incubated at 15-25° C. for 7-15 min, preferably at room temperature for 10 min. Subsequently, it is added onto a column of a plate of the DNEASY® 96 Tissue Kit, the QIAAMP® 96 DNA Blood Kit, or the QIAAMP® DSP 96 Virus MDx Kit or onto a column of the DNEASY® Tissue Kit, the QIAAMP® DNA Mini Kit, the QIAAMP® DNA Micro Kit, the QIAAMP® Viral RNA Mini, or the QIAAMP® DSP Virus Kit. After centrifugation of the plate at 4,000-6,000×g for 1-10 min, preferably at 5,790×g for 4 min, or of the column at >15,000×g for 0.5-10 min, preferably for 20,000×g for 1 min, the DNA is bound to a column. Thereafter the column is washed with 300-750 μl, preferably with 500 μl of washing buffer AW1. Subsequently the plate is centrifuged at 4,000-6,500×g for 1-5 min, preferably at 5.790×g for 2 min and the column is centrifuged at >15,000×g for 0.5-5 min, preferably for >20,000×g for 1 min, respectively. This is followed by an alkaline hydrolysis, wherein 470-530 μl, preferably 500 μl of a solution comprising 0.2 mol/l sodium hydroxide and 90% ethanol is added for 11-20 min at 17-24° C., preferably for 15 min at room temperature to the column and therewith to the DNA. This solution is withdrawn by centrifugation of the plate at 4,000-6,500×g for 1-5 min, preferably at 5.790×g for 2 min and of the column at >15,000×g for 0.5-5 min, preferably for >20,000×g for 1 min, respectively. Although it is not necessary it can be favourable to repeat the washing step including the subsequent centrifugation step with the washing buffer AW1 as it is described above. However the column is washed by addition of 300-750 μl, preferably 500 μl of washing buffer AW2. This is followed by a centrifugation of the plate at 4,000-6,500×g for 5-30 min, preferably at 5.790×g for 15 min and of the column at >15,000×g for 0.5-10 min, preferably for 20,000×g for 3 min, respectively. In addition, after removal of the flow-through the column is centrifuged at >15,000×g for 0.5-5 min, preferably for 20,000×g for 1 min. The elution of the DNA from a column of a plate is carried out by addition of 75-170 μl, preferably 120 μl of elution buffer which can be AE, AVE or EB (all QIAGEN®) or water each preheated to 60-80° C., preferably to 70° C. The plate is incubated for 1-20 min at 15-30° C., preferably for 5 min at room temperature, before it is centrifuged at 4,000-6,500×g for 0.5-20 min, preferably at 5,790×g for 2 min. The elution of the DNA from a column of the DNEASY® Tissue Kit, the QIAAMP® DNA Mini Kit, the QIAAMP® DNA Micro Kit, the QIAAMP® Viral RNA Mini, or the QIAAMP® DSP Virus Kit is carried out as in the following: In a first application 25-150 μl, preferably 35-120 μl of elution buffer is added. The elution buffer can be AE, AVE or EB (all QIAGEN®) or water each adjusted to 15-30° C., preferably to room temperature. After incubation for 0.5-20 min at 15-30° C., preferably for 1-5 min at room temperature, the column is centrifuged for 0.5-5 min at 4,000-8,000×g, preferably for 1 min at 6,000×g. Although it is not necessary, it might be favourably to carry out a second elution step. In doing so, 25-75 μl, preferably 35-60 μl of the above specified elution buffer is added. Again, the column is incubated for 0.5-20 min at 15-30° C., preferably for 1-5 min at room temperature, before it is centrifuged for 0.5-5 min at 4,000-8,000×g, preferably for 1 min at 6,000×g. The flow-through of the first and second elution step containing the DNA are combined.

In a preferred embodiment, the DNA purification step comprises
- mixing of 140 µl of bisulfite treated sample with 560 µl binding buffer,
- addition of 560 µl ethanol,
- centrifugation at 1.450×g for 1 s,
- incubation at room temperature for 10 min,
- application of the reaction mixture in one or two steps onto a plate of the DNEASY® 96 Tissue Kit, the QIAAMP® 96 DNA Blood Kit, or the QIAAMP® DSP 96 Virus MDx Kit or onto a column of the DNEASY® Tissue Kit, the QIAAMP® DNA Mini Kit, the QIAAMP® DNA Micro Kit, the QIAAMP® Viral RNA Mini, the QIAAMP® DSP Virus Kit,
- centrifugation of the plate at 5.790×g for 4 min or of the column at >20,000×g for 1 min,
- application of 500 µl buffer AW1 and subsequent centrifugation of the plate at 5.790×g for 2 min or of the column at >20,000×g for 1 min,
- application of 500 µl of a solution containing 0.2 mol/l sodium hydroxide and 90% ethanol, incubation for 15 min at room temperature and subsequent centrifugation of the plate at 5.790×g for 2 min or of the column at >20,000×g for 1 min,
- optional, application of 500 µl buffer AW1 and subsequent centrifugation of the plate at 5.790×g for 2 min or of the column at >20,000×g for 1 min,
- application of 500 µl of buffer AW2 and subsequent centrifugation of the plate at 5.790×g for 15 min or of the column at 20,000×g for 3 min,
- centrifugation of the column at 20,000×g for 1 min,
- elution of the DNA from the plate by application of 120 µl elution buffer AE, AVE or EB or water preheated to 70° C., incubation for 5 min at room temperature and centrifugation for 2 min at 5,790×g or elution of the DNA from a column by a first application of 35-120 µl elution buffer AE, AVE or EB or water adjusted to room temperature, incubation for 1-5 min at room temperature and centrifugation for 1 min at 6,000×g, and an optional second application of 35-60 µl elution buffer AE, AVE or EB or water adjusted to room temperature, incubation for 1-5 min at room temperature and centrifugation for 1 min at 6,000×g.

In a preferred embodiment the purification step is carried out by means of a MICROCON™ filter device (MILLIPORE®). This is done essentially as described in the manufacturer's instruction with an additional alkaline hydrolysis step and some modifications. The sample after the bisulfite treatment is adjusted with water to a volume of 350-500 µl, before it is applied to a MICROCON™ filter device which detains the DNA. Thereafter 25-1,000 µl of a solution comprising 0.1-0.3 mol/l, preferably 0.15-0.25 mol/l, and particularly preferred 0.2 mol/l sodium hydroxide are applied, wherein it is favourable but not necessary to incubate the alkaline solution for 3-25 min at 15-26° C. The device is then washed with 200-1,000 µl TE buffer. The TE buffer has a pH of 8.0 and comprises 10 mmol/l Tris(tris-hydroxymethyl-amino-methan) and 0.1 mmol/l EDTA. The DNA is removed from the device by means of 30-100 µl of TE buffer preheated to 40-65° C. The buffer on the device is incubated for 5-25 min at 10-60° C. and will then contain the DNA.

In an embodiment, the purification step is carried out by means of a MICROCON™ filter device, comprising
- adjustment of the sample after the bisulfite reaction with water to a volume of 350-500 µl,
- application of the DNA onto a MICROCON™ filter device,
- treatment with 25-1,000 µl of 0.2 mol/l sodium hydroxide, optional incubation for 3-25 min at 15-26° C.,
- washing with 200-1,000 µl TE buffer, the TE buffer pH 8.0 containing 10 mmol/l tris-hydroxymethyl-amino-methan and 0.1 mmol/l EDTA,
- removal of the DNA by means of 30-100 µl TE buffer preheated to 40-65° C. incubated for 5-25 min at 10-60° C.

In a particularly preferred embodiment the sample after bisulfite reaction is adjusted with water to a volume of 370-450 µl, preferably of 400 µl for purification. The mixture is then added to a MICROCON™ filter device. Subsequently the device is centrifuged at 10,000-18,000×g for 5-30 min, preferably at 14,000×g for 15 min. Although it is not necessary it is favourable to follow with 1-2 repetitions of a washing step. For each washing step 400 µl TE buffer as described above are added and subsequently the device is centrifuged at 10,000-18,000×g for 5-30 min, preferably at 14,000×g for 12 min. Afterwards 50-700 µl, preferably 100-400 µl of 0.2 mol/l sodium hydroxide are added to the device. Although not necessary it is favourable to incubate the solution of the device for 5-20 min at 15-30° C., preferably for 10 min at room temperature. Subsequently the device is centrifuged at 10,000-18,000×g for 5-30 min, preferably at 14,000×g for 10-12 min. After this the device is washed for 1-4 times as described before. The DNA is recovered by elution in one or two steps. Thereby 30-85 µl, preferably by 37.5-75 µl of the TE buffer preheated to 45-60° C., preferably to 50° C. are added. The buffer on the device is then incubated for 7-15 min at 12-55° C., preferably for 10 min at 15-50° C., before the device is inverted and centrifuged at 500-5,000×g at 0.5-20 min, preferably at 1,000×g for 5 min. This embodiment is essentially carried out as it is described in WO05/038051 (this reference is incorporated by its entirety).

In a preferred embodiment, the purification step comprises
- adjustment of the sample after the bisulfite reaction with water to a volume of 400 µl,
- application of the mixture onto a MICROCON™ filter device and subsequent centrifugation at 14,000×g for 15 min,
- optional, 1-2 repetitions of the following washing step: application of 400 µl TE buffer, the TE buffer pH 8 containing 10 mmol/l tris-hydroxymethyl-amino-methan and 0.1 mmol/l EDTA, subsequent centrifugation at 14,000×g for 12 min,
- application of 100-400 µl of 0.2 mol/l sodium hydroxide, optional incubation for 10 min at room temperature, and subsequent centrifugation at 14,000×g for 10-12 min
- 1-4 repetitions of the following: application of 400 µl water or TE buffer and subsequent centrifugation at 14,000×g for 12 min
- elution in one or two steps by application of 37.5-75 µl TE buffer preheated to 50° C., incubation for 10 min at 15-50° C., and subsequent inversion of the MICROCON™ filter device and centrifugation at 1,000×g for 5 min.

Amplification Step

In an embodiment of the invention the amplification step comprises a detection of positions which are methylated in the genomic DNA of the archived sample. Alternatively, it also comprises a detection of positions which are unmethylated in the genomic DNA of the archived sample. Of course, it is also possible to detect simultaneously positions which are methylated and to detect positions which are unmethylated in the genomic DNA of the archived sample by the amplification step.

It is especially preferred that the methylation pattern is analysed by means of bisulfite sequencing, the COBRA method, the Ms-SNuPE (Methylation-sensitive Single Nucleotide Primer Extension) method, the MSP (Methylation Specific PCR) method, including the nested MSP method, the HEAVYMETHYL™ method, the METHYLIGHT™ method, or the QM assay. Of course, if desired, it is also possible to combine two or more of these methods.

In an embodiment of the invention, the amplification step is carried out by one or more of the following methods and/or by a combination of one or more of the following methods with each other: PCR, the bisulfite sequencing method, the COBRA method, the Ms-SNuPE (Methylation-sensitive Single Nucleotide Primer Extension) method, the MSP (Methylation Specific PCR) method, the nested MSP method, the HEAVYMETHYL™ method, the METHYLIGHT™ method, or the QM assay.

According to the invention, a better ability of amplification is given if one or more of the following amendments are made in comparison to normal conditions as a person with ordinary skills in the art would probably choose them with respect to the methods specified above: i) increase in the concentration of the polymerase activity; ii) increase in the concentration of each nucleotide, whereby simultaneously the concentration of magnesium chlorid has also be adjusted as explained below; and iii) elongation of the time for the elongation and annealing step as explained below. This is the case for bisulfite treated DNA derived from archieved samples as well as for non-bisulfite treated genomic DNA derived from archieved samples.

In a preferred embodiment of the invention the amplification step is carried out with use of a DNA polymerase and comprises one or more of the following: A) The DNA polymerase concentration is in the range of 0.05-0.3 U/µl of the reaction mixture. B) The concentration of each nucleotide is in the range of 200-800 µmol/l. Thereby the concentration of magnesium chlorid ($MgCl_2$) in the reaction mixture is adjusted to the concentration of nucleotides as it is well known for those skilled in the art. C) The time for elongating the template DNA is in the range of 0.1-1.0 s/bp of the template DNA. This time usually comprises for a PCR the elongation step as well as the annealing step if the case may be. If the annealing is performed at temperatures below 53° C., this time corresponds only to the elongation step.

In an embodiment, the method of the invention includes a method for amplifying DNA derived from an archived sample, comprising one or more of the following:
the polymerase concentration is in the range of 0.05-0.3 U/µl,
the concentration of each nucleotide is in the range of 200-800 µmol/l,
the time of the elongation step is in the range of 0.1-1.0 s/bp.

In a particularly preferred embodiment the amplification step comprises one or more of the following: A) A polymerase concentration in the range of 0.08-0.25 U/µl, preferably the concentration is 0.15 U/µl in the reaction mixture. B) The concentration of each nucleotide is in the range of 350-650 µmol/l, preferably the concentration of each nucleotide is 400 µmol/l in the reaction mixture. As already explained before the concentration of magnesium chlorid ($MgCl_2$) in the reaction mixture is thereby adjusted to the concentration of the nucleotides as it is well known for those skilled in the art. C) The time for elongating the template DNA is in the range of 0.25-0.75 s/bp of the template DNA, preferably it is 0.5 s/bp of the template DNA. As already described, this time usually comprises for a PCR the elongation step as well as the annealing step if the case may be. If the annealing is performed at temperatures below 53° C., this time corresponds only to the elongation step.

In a preferred embodiment, the amplification step comprises one or more of the following:
the polymerase concentration is 0.15 U/µl,
the concentration of each nucleotide is 400 µmol/l,
the time of the elongation step is 0.5 s/bp.

In a preferred embodiment of the invention, the amplification step is carried out in order to amplify a defined fragment, a subfraction of fragments or to amplify the whole genome. For this, one or more of the methods as they are known to those skilled in the art can be used. For this, the amplification step can be carried out by amplification reactions which are non-PCR based methods for example by the NASBA/TMA technique. But more preferably, ligase mediated chain reaction (LCR), and in particular polymerase chain reaction (PCR) methods are used.

Preferably, such an amplification is used for an enrichment of the DNA of interest carrying the epigenomic information of the archieved sample. Thereafter any method for methylation analysis can be performed, in particular the bisulfite sequencing method, the COBRA method, the Ms-SNuPE (Methylation-sensitive Single Nucleotide Primer Extension) method, the MSP (Methylation Specific PCR) method, the nested MSP method, the HEAVYMETHYL™ method, the METHYLIGHT™ method, or the QM assay.

Furthermore, it is also preferred that after an amplification of a defined fragment, a subfraction of fragments or the whole genome the amplified DNA is subject to additional analyses, for example for the analysis of point mutations or SNPs.

In principle, according to the invention it is possible that the amplification reaction mixtures comprise more than two primers. Therefore the amplification will result in more than one amplicon. In case the amplification is carried out by PCR, such a procedure is known as multiplex PCR by those skilled in the art. Such a procedure is in particular advantageous if only small amounts of DNA are available. Additional it has also the advantage of a reduction of costs, lowering the handling effort, and shorting of the experiment, e.g. results earlier obtained.

Embodiments for Small Amounts of an Archived Sample as Starting Material

In an embodiment of the invention, small amounts of an archived sample are used as starting material. Such small amounts can be any part of a tissue of an archived sample. This tissue part is in the following size range: The area is between 0.025-50 $mm^2$, preferably between 0.05-10 $mm^2$, and most preferably between 0.1-3 $mm^2$. Thereby the thickness of the tissue part is in the range of 5-20 µm, preferably in the range of 7-13 µm, and most preferably the tissue part has a thickness of 10 µm. Of course, tissue parts with other dimensions are also applicable. If the tissue part is of a different volume, a person with ordinary skills in the art will know how to adjust the following embodiments for small amounts of an archived sample as starting material.

Microdissection

In an preferred embodiment, cell of an archived sample are microdissected. Therefore a section of an archived sample in the range of 5-20 µm, preferably in the range of 7-13 µm, and most preferably of 10 µm thickness is mounted on a slide as specified below. The microdissection can be done for example by means of a laser capture processing. But any other method known to those skilled in the art is as well suitable.

Various methods for microdissection by means of a laser capture processing are known to those skilled in the art (for example Eltoum I A, Siegal G P and Frost A R. 2002. Microdissection of histologic sections: past, present, and future. Adv Anat Pathol. September; 9(5):316-22). In a preferred embodiment, the laser capture method is the AutoPix™ LCM System (Arcturus, USA). In brief, a film is thermally fused to the respective tissue area by means of a laser, whereby the tissue area is dissected.

In another preferred embodiment, the laser mediated microdissection is carried out by mounting the tissue section onto a membrane coated slide for example onto MembraneSlides (P.A.L.M.® Microlaser Technologies AG, Germany).

In further preferred embodiment, the tissue section is mounted onto a conventional microscopic slide. After this the tissue section is subjected to a staining before the desired areas are microdissected. Of course, also similar procedures are also applicable as long as they enable the identification of desired parts of the sample, in particular as long as they enable the identification of desired cell or group of cells in the sample. Such a staining can be for example also a hematoxylin-eosin staining, a methylene blue staining, a hemalum-eosin staining, an azan staining, a periodic acid-schiff staining, a prussian blue staining, a Masson-Goldner staining, a Ladewig staining, a elastica-van Gieson staining, a Gomori staining, a methyl green staining, a nuclear fast red staining, a Evans blue staining, a light-green SF yellowish staining, a Wright's staining, a May-Grunwald staining, a toluidine blue O staining, an azure B staining, a Giemsa staining or any other histological or histopathological staining. But also any immunohistological staining can be used, for example any kind of staining which is based on antibodies or on DNA or RNA hybridisation. These staining methods are well described and are well known to those skilled in the art. The corresponding embodiments are herewith enclosed in the method according to the invention. Of course, any staining can be completely omitted if it is not desired or suitable for microdissection.

Microdissection is carried out by means of a Microbeam instrument (P.A.L.M.® Microlaser Technologies AG, Bernried, Germany). But also similar instruments which enable a dissection of single cells, of group of cells or of tissue parts can be used according to the invention. These techniques are well known to those skilled in the art and are therefore herewith included as preferred embodiments.

The dissected material is collected in tubes preferably with adhesive caps for further processing. The adhesive caps can be any kind of adhesive caps for example Adhesive Caps 200 (P.A.L.M.® Microlaser Technologies AG, Bernried, Germany). Because of the microdissection no removal of paraffin is necessary.

In another preferred embodiment, the dissected material is collected in the cap of a normal tube which contains the below specified volume of lysis buffer.

Lysis Step

In an embodiment, the microdissected sample material is subjected to a lysis step. Therefore 20 µl lysis buffer (50 mmol/l Tris-HCl, pH 8.0, 1 mmol/l EDTA, 0.5 v/v % Tween, 10 ng/µl poly-dA, 3 mg/ml proteinase K) were carefully added to the cap. As already described above, other lysis buffers as they are known to those skilled in the art are also applicable. The tubes were closed carefully avoiding a loosening of the drop from the cap. Subsequently the tubes were incubated for 1-48 h, preferably for 5-24 h, and most preferably for 12 h at 40-80° C., preferably at 50-70° C., and most preferably at 60° C. This can be done for example in a water-bath, thermomixer or PCR cycler. If a PCR cycler is used, preferably also the lid of the cycler is set to same temperature as the cycler, because the sample material is located at the caps.

After incubation the sample is centrifuged to transfer the lysed sample to the bottom of the tube.

In an preferred embodiment, the amount of lysis buffer is adjusted to the sizes of the dissected material. This is characterized in that at least the dissected material is completely covered by the lysis buffer. After lysis of the material, the lysis buffer is concentrated to 20 µl by vacuum centrifugation, lyophilisation or any other suitable methods as they are known to those skilled in the art.

Bisulfite Treatment

In an embodiment, the lysed sample is then directly subjected to bisulfite treatment because of the small amount of starting material and hence DNA. For bisulfite treatment, 9-70 µl, preferably 12-52 µl, and most preferably 38 µl bisulfite solution are added to the cap. A bisulfite solution is used as it is already described above. Subsequently the bisulfite solution at the cap is incubated for 0.5-15 min, preferably for 2-10 min, and most preferably for 5 min at 0-80° C., preferably at 10-40° C., in particular preferably at 15-30° C., and most preferably at room temperature. The addition and incubation of the bisulfate solution at the cap dissolves any remaining DNA in the cap. After the incubation, the sample is centrifuged.

In an preferred embodiment, the addition of bisulfite solution is carried by two steps which resemble themselves. This has the advantage that all DNA attached to the cap is subject for further processing. In the first step, 9-35 µl, preferably 12-26 µl, and most preferably 19 µl bisulfite solution are added to the cap. A bisulfite solution is used as it is already described above. Subsequently the bisulfite solution at the cap is incubated for 0.5-15 min, preferably for 2-10 min, and most preferably for 5 min at 0-80° C., preferably at 10-40° C., in particular preferably at 15-30° C., and most preferably at room temperature. The addition and incubation of the bisulfate solution at the cap dissolves any remaining DNA in the cap. After the incubation, the sample is centrifuged, before again bisulfite solution is added in a second step which is a repetition of the first step.

Thereafter, in an embodiment, 2-12 µl, preferably 4-8 µl, and most preferably 6 µl of DME solution as it is described above are added. The bisulfite conversion is in the following conducted as described already above. The corresponding embodiments for small amounts of starting material are herewith enclosed. In a particular embodiment the following temperature protocol is applied: 5 min 99° C., 22 min 60° C., 3 min 99° C., 97 min 60° C., 3 min 99° C. and 177 min 60° C. Therefore one or more waterbath, thermomixer or PCR cycler are used.

DNA Purification

In an embodiment, the DNA after bisulfite treatment is purified.

Therefore methods for purification of small amounts of DNA as they are known to those skilled in the art can be used. In a preferred embodiment the purification is carried out by means of ZYMO-SPIN™ IC columns (Zymo Research, USA). Therefore, 75-250 µl, preferably 125-210 µl, and most preferably 166 µl of buffer AVL, AL or ATL (all QIAGEN®, Germany) were added to the ZYMO-SPIN™ IC columns. Thereafter the bisulfite reaction mix is added to the column. The used pipett tip can be placed in the respective bisulfite reaction tube for further use in order to avoid DNA loss due to drops sticking at the tip, but this is not strictly necessary according to the invention. According to the invention also a new pipett tip may be used. In addition, 20-170, preferably 60-120 µl, and most preferably 90 µl of buffer AVL, AL or ATL are added to the empty bisulfite reaction tube and subsequently transferred to the corresponding ZYMO-SPIN™ IC column. The bisulfite reaction mix and the transferred buffer AVL, AL or ATL are mixed in the columns by pipetting up and down several times. Subsequently, the mixture is incubated in the column for 1-30 min, preferably for 3-15 min, and most preferably for 10 min at 0-60° C., preferably at 10-40° C., in particular preferably at 15-30° C., and most preferably at room temperature. After this incubation, 175-400 µl, preferably 225-275 µl, most preferably 250 µl of ethanol are added to the columns and mixed. Subsequently the column is centrifuged for 0.5-10 min, preferably for 1-5 min, most preferably for 1 min at 10,000-20,000×g, preferably for 14,000-18,000×g, and most preferably for 16,000×g. The column is then transferred to a new 2 ml collection tube. After this, 250-750 µl, preferably 350-650 µl, and most preferably 500 µl of a buffer or solution comprising 0.2 mol/l NaOH and/or 90% v/v ethanol are added to the column. Also instead, suitable buffers or solutions as they are already described above can be used. In the following the column is centrifuged for 0.5-10 min, preferably for 1-5 min, most preferably for 1 min at 10,000-20,000×g, preferably for 14,000-18,000×g, and most preferably for 16,000×g. The column is then transferred to a new 2 ml collection tube. After this, 250-750 µl, preferably 350-650 µl, and most preferably 500 µl of buffer AW1 (QIAGEN®, Germany) are added to each column. Again, the column is centrifuged for 0.5-10 min, preferably for 1-5 min, most preferably for 1 min at 10,000-20,000×g, preferably for 14,000-18,000×g, and most preferably for 16,000×g and transferred to a new 2 ml collection tube. Thereafter, 250-750 µl, preferably 350-650 µl, and most preferably 500 µl of buffer AW2 (QIAGEN®, Germany) are added to each column. Again, the column is centrifuged for 0.5-15 min, preferably for 1-8 min, most preferably for 3 min at 10,000-20,000×g, preferably for 14,000-18,000×g, and most preferably for 16,000×g. Afterwards, the column is placed in a collection tube for DNA elution which is suitable for further analysis. The elution is carried out by one step. Therefore, the DNA is eluted by the addition of 15-50 µl, preferably of 20-30 µl, and most preferably of 25 µl of water or of buffer AE, AVE or EB (all QIAGEN®) prewarmed to 30-70° C., preferably 40-60° C., and most preferably to 50° C. Thereafter the column is incubated for 0-10 min, preferably for 1-5 min, most preferably for 1 min, before it is centrifuged for 0.5-10 min, preferably for 1-5 min, most preferably for 1 min at 1,000-10,000×g, preferably for 4,000-8,000×g, and most preferably for 6,000×g.

In a preferred embodiment, the elution is carried out in two steps. In a first step, the DNA is eluted by the addition of 7.5-25 µl, preferably of 10-15 µl, and most preferably of 12.5 µl of water or of buffer AE, AVE or EB (all QIAGEN®) prewarmed to 30-70° C., preferably 40-60° C., and most preferably to 50° C. Thereafter the column is incubated for 0-10 min, preferably for 1-5 min, most preferably for 1 min, before it is centrifuged for 0.5-10 min, preferably for 1-5 min, most preferably for 1 min at 1,000-10,000×g, preferably for 4,000-8,000×g, and most preferably for 6,000×g. Afterwards the second elution step is carried out as a repetition of the first elution step.

Subsequent Analysis

In an embodiment, DNA is quantificated directly after lysis or after bisulfite treatment and subsequent purification by means of a real time assay (see example 10).

In an embodiment of the invention the lysed sample is directly subject to subsequent analysis without any bisulfite treatment or any DNA purification. This is in particular preferred if a bisulfite treatment is not necessary for subsequent analysis. For example for the analysis of the methylation pattern by means of restriction enzymes. Examples for such methods are as already mentioned the DMH method or the restriction assay also known as MestVal method (see above).

In an preferred embodiment, the DNA after bisulfite treatment and subsequent purification is subject to subsequent analysis or amplification. In an particular embodiment it is preferred that the subsequent analysis is an analysis of the methylation pattern of the original DNA derived from the archived sample.

For the analysis or amplification of bisulfite treated and purified DNA derived from small amounts of an archived sample refer to the said above according to the amplification step. Corresponding embodiments are included herewith.

Test Kits

The subject of the present invention is also a kit, comprising one or more of the following:

A container.

One or more organic solvents for removal of paraffin. This can be a solvent which dissolves paraffin and is a solvent of the group "limonene, xylene or any mixture of these solvents". Of course, the kit may comprise organic solvents like benzene, ethylbenzene, toluene or solvents with similar chemical properties or any mixture of these solvents. Furthermore the kit may comprise one or more organic solvents which are suitable for washing the sample after dissolving paraffin and which enable a better rehydratisation of the sample. Such kind of solvent or solvents is a solvent of the group of "ethanol, methanol, isopropanol or any mixture of these solvents with each other or with water". Of course, the kit may also comprise solvents with comparable chemical properties.

Protease in solution or as a powder. This protease can be a serin protease, a thiol protease, a carboxy protease, a metalloprotease, proteinase K or any mixture of these proteases. In a preferred variant of the kit the protease is proteinase K in from of a powder or dissolved in an appropriate solution.

One or more lysis buffer, the lysis buffer comprising 50 mmol/l Tris(tris-hydroxymethyl-amino-methan) pH 8.0, 1 mmol/l EDTA, 0.5% Tween 20 v/v. Of course, the kit may also comprise any other lysis buffer with similar properties. Such a buffer may include detergents and/or chaotropic salts.

One or more solutions for DNA extraction. According to the invention the kit may comprise one or more of the following buffers: a) binding buffer AL/E (QIAGEN®); b) binding buffer AL (QIAGEN®); c) binding buffer ATL (QIAGEN®); d) binding buffer AVL (QIAGEN®); e) ethanol, preferentially at least 96% pure ethanol; f) washing buffers AW1 (QIAGEN®); g) washing buffer AW2 (QIAGEN®); h) elution buffer AE (QIAGEN®); i) elution buffer AVE (QIAGEN®); j) elution buffer EB (QIAGEN®); k) water One or more devices for DNA extraction. According to the invention the kit may comprise one or more of the following plates or columns as they are part of the following kits: DNEASY® 96 Tissue Kit, QIAAMP® 96 DNA Blood Kit, QIAAMP® DSP 96 Virus MDx Kit, DNEASY® Tissue Kit, QIAAMP® DNA Mini Kit, QIAAMP® DNA Micro Kit, QIAAMP® Viral RNA Mini or QIAAMP® DSP Virus Kit (all QIAGEN®). According to the invention also devices of other kits may comprise to a kit of the invention. For example this can be devices which are based on the "nexttec"-technology (nexttec) or the "charge-switch"-technology (invitrogen). If the case may be, the kit comprises also additional solutions suitable for extracting DNA.

One or more solutions for bisulfite treatment. This can be any solution as described in WO05/038051. Preferably the kit may comprise:

A) A bisulfite solution with a pH in the range of 4.7 to 6.5, preferably in the range of 5.0 to 6.0, and particularly preferred in the range of 5.45 to 5.50. The bisulfite solution comprises hydrogensulfite in a concentration of 3.5-6.0, preferably in a concentration of 4.4-5.3, and particularly preferred in a concentration of 4.83-4.93 mol/l. For example, such kind of bisulfite solution can be obtained by adding 4.708 g of sodium disulfite and 1.128 g of sodium sulfite to 10 ml of water. Of course, as known to those skilled in the art, a kit may also comprise solutions with other concentrations. As the case may be, appropriate volumes have then to be taken. After dissolving of the salts, the final volume of the solution is about 12 ml. Therefore the kit may comprise sodium disulfite and/or sodium sulfite each alone or combined in form of salts or dissolved in solution.

B) Additionally a kit may comprise water.

c) An organic radical scavenger solution comprising an organic solvent and 50-1.000 mmol/l, preferably 100-750 mmol/l, and particularly preferred 158-500 mmol/l of the radical scavenger 6-hydroxy-2,5,7,8-tetramethyl-chroman-2-carboxylic acid or any other suitable radical scavenger as described in WO01/98528 or WO05/038051. For preferred variants of the kit, a kit may comprise a DME solution comprising 250-1.000 mmol/l, preferably 350-750 mmol/l, and particularly preferred 500 mmol/l 6-hydroxy-2,5,7,8-tetramethyl-chroman-2-carboxylic acid dissolved in diethylenegly-coldimethylether (DME) or a dioxane solution comprising 50-500 mmol/l, preferably 75-300 mmol/l, and particularly preferred 158 mmol/l 6-hydroxy-2,5,7,8-tetramethyl-chroman-2-carboxylic acid dissolved in 1,4-dioxane.

One or more devices for bisulfite treatment. This can be any device as described in WO01/98528 or WO05/038051.

One or more solutions for DNA purification. This can be in part the same solutions as described above as for the DNA extraction. According to the invention the kit may comprise one or more of the following buffers:

A) Binding buffer AVL (QIAGEN®), the binding buffer AVL may comprise 1-50 ng/µl, preferably 5-25 ng/µl, particularly preferred 10 ng/µl RNA or a comparable amount of any nucleic acid.

B) Ethanol, preferentially at least 96% pure ethanol.

C) Washing buffer AW1 (QIAGEN®).

D) Washing buffer AW2 (QIAGEN®).

E) One or more solutions suitable for an alkaline hydrolysis. Preferably such kind of solution comprises 0.1-0.3 mol/l, preferably 0.15-0.25 mol/l, and particularly preferred 0.2 mol/l sodium hydroxide and 60-90%, preferably 75-90%, and particularly preferred 90% ethanol. It is further preferably that such kind of solutions comprise 0.1-0.3 mol/l, preferably 0.15-0.25 mol/l, and particularly preferred 0.2 mol/l sodium hydroxide.

F) Elution buffer AE (QIAGEN®);

G) Elution buffer AVE (QIAGEN®);

H) Elution buffer EB (QIAGEN®);

I) Water.

One or more devices for DNA purification. According to the invention this can be the same device as already described for the extraction of DNA. It is preferable that the kit may comprise one or more of the following plates or columns as they are part of the following kits: DNEASY® 96 Tissue Kit, QIAAMP® 96 DNA Blood Kit, QIAAMP® DSP 96 Virus MDx Kit, DNEASY® Tissue Kit, QIAAMP® DNA Mini Kit, QIAAMP® DNA Micro Kit, QIAAMP® Viral RNA Mini or QIAAMP® DSP Virus Kit (all QIAGEN®). Also ZYMO-SPIN™ columns I, II and/or III may be comprised. According to the invention also devices of other kits may comprise to a kit of the invention. For example this can be devices which are based on the "charge-switch"-technology (invitrogen). If the case may be, the kit comprises also additional solutions suitable for extracting DNA. According to the invention the kit may also comprise columns or devices with are based on the MICROCON™ technology.

solutions and/or substances for DNA amplification. According to the invention this may be one or more of the following:

A) One or more primers, which are suitable for the amplification of one or more DNA amplificates, amongst others the primer or primers can be modified, for example with a label for detection as well known by a person skilled in the art like the dye FAM, Cy 3, Cy 5, biotin, digoxigenin, B) One or more probes, which can be used to specifically record the amplification of one or more amplificates for example in a real-time-assay, amongst others the probe or probes can be modified, for example with a quencher and/or a label for detection as well known by a person skilled in the art like the dye FAM or the quencher BHQ black hole or dabcyl, C) One or more blockers, which are nucleic acids and can be used to block the binding of a specific primer or the replication by DNA polymerase, amongst others the blocker or blockers can be modified, for example with 3' phosphate as well known by a person skilled in the art, D) One or more reaction buffers, which are suitable for a PCR reaction, E) Nucleotides, which can be dATP, dCTP, dTTP, dUTP and dGTP or any derivative of these nucleotides, F) $MgCl_2$ as a substance or in solution and/or any other magnesium salt, which can be used to carry out a DNA polymerase replication, G) DNA polymerase, for example Taq DNA polymerase or any other polymerase with or without proof-reading activity, H) Dye or quencher, which can be used for the detection of the amplificates as known in the art, for example an intercalating dye like SYBR Green or a dye for linkage to a primer or probe or blocker like the dye FAM or the quencher BHQ black hole or dabcyl, a manual and/or description to carry out the method of the invention or only to carry an embodiment of the method according to the invention, and/or any reagent, solution, device and/or instruction which is useful for realisation of an assay according to the invention.

Subject of the invention is a test kit for carrying out a method according to one or more of the embodiments of the inventions, comprising a container organic solvents for removal of paraffin, proteinase K and/or buffer for lysis, solutions and/or devices for DNA extraction, solutions and/or devices for bisulfite treatment, solutions and/or devices for DNA purification, solutions and/or substances for DNA amplification a manual and/or description for carrying out the method of the invention.

Use of the Methods and Test Kits

The methods and test kits disclosed herein are preferably used for the detection of the DNA methylation status of a sample taken from a tissue of a diseased or healthy person or of a person who's status of health is not determined so far regarding a defined disease. In a particularly preferred manner the so determined DNA methylation statuses are then compared with each other and/or with a reference DNA methylation status.

Therefore the invention also comprises the use of the method according to one or more of the embodiments or of a test kit according to the invention for the detection of the DNA methylation status.

In case the status of health of a person from whom the sample is derived is not or only insufficiently determined so far, the results of the DNA methylation status analysis can be used to determine the status of health of said person regarding a specific disease or any predispositions for a specific disease. Therefore it is particularly preferred that the DNA methylation status is used for diagnosing a disease or for diagnosing a predisposition for a disease. Furthermore, it is also particularly preferred that the DNA methylation status is used for diagnosing a progression of a disease, if the status of health of a person regarding said specific disease has been already been determined.

According to the invention, the use of the methods and kits described herein are especially preferred if the disease is a cancer disease.

The use of methods and kits described herein is in particular preferred, if the use is characterized in that the DNA methylation status is used for diagnosing a disease, for diagnosing a predisposition for a disease and/or for diagnosing a progression of a disease, wherein in particular the disease is a cancer disease.

The use of methods and kits described herein is in particular preferred, if it is characterized in that it is predicted if the health status of a person will be positively or negatively be influenced by a drug or chemical substance or not. This is particularly preferred if the use of the methods and kits described herein is characterized in that the DNA methylation status is used for predicting if the health status of a person will be positively or negatively influenced by a drug or chemical substance or not. The use is especially preferred if the health status is characterised by a disease, a predisposition for a disease and/or by a progression of a disease. This is most especially preferred if the disease is a cancer disease.

The use of the methods and kits described herein is especially preferred if the DNA methylation status is characterized in that positions are methylated or non-methylated compared to normal conditions and if a single defined disease or a predisposition for a single defined disease exists. Of course, the use of the methods and kits described herein is also preferred if the DNA methylation status may also be characterized in that positions are methylated or non-methylated compared to various levels of diseased conditions and if a gradually progressive disease exists.

The use of methods and kits described herein is especially preferred, if the DNA methylation status is characterized in that positions are methylated or non-methylated compared to normal conditions if a single defined disease exists.

If status of health of a person from whom the sample is derived is independently determined from the DNA methylation status, the results of the DNA methylation status analysis can be used to identify a disease specific DNA methylation status. Such disease specific DNA methylation status may include one or more sites of a potential DNA methylation and/or the knowledge of the presence or absence of a methylation at CG dinucleotides, in case of the presence or absence of a particular disease. Therefore it is particularly preferred to use any method or kit described herein for the identification of an indication-specific target. According to this, a) DNA of an archived sample originating from a diseased tissue is prepared and the DNA methylation status is determined; b) DNA of a sample originating from a healthy tissue is prepared and the DNA methylation status is determined; c) a indication-specific target is defined as differences in the DNA methylation status of a DNA derived from a diseased tissue in comparison to a DNA derived from a healthy tissue. Thereby the sample of the diseased tissue and the sample of the healthy tissue can originate from different persons. Preferably these persons are relatives. It is particularly preferred that the sample of the diseased tissue and the sample of the healthy tissue originate from the same person, and it is especially preferred that the samples originate from adjacent tissues.

Of course, in the same manner also indication-specific targets can be identified which are specific for a predisposition for a disease or which are specific for a progression of a disease.

The use according to one or more of the embodiments or of a test kit according to the invention is preferred for identifying an indication-specific target, wherein a) DNA of an archived sample originating from a diseased tissue is prepared and the DNA methylation status is determined, b) DNA of sample originating from a healthy tissue is prepared and the DNA methylation status is determined, c) a indication-specific target is defined as differences in the DNA methylation status of a DNA derived from a diseased tissue in comparison to a DNA derived from a healthy tissue.

The use of the methods or kits described herein is preferred if the indication-specific target is a protein, peptide or RNA or any other endogenous bioactive substance as for example hormones.

In particular, the use is preferred if the indication-specific target is a protein, peptide or RNA.

The said use is preferred if a per se known modulator of the protein, peptide, RNA or other endogenous bioactive substance is assigned to the specific indication of the diseased tissue.

In particular, a use is preferred wherein a per se known modulator of the protein, peptide or RNA is assigned to the specific indication of the diseased tissue.

Furthermore, the use of such a modulator is particularly preferred for preparing a pharmaceutical composition in case of a specific indication. This is especially preferred if the specific indication is a specific cancer indication.

In particular, the use of the modulator assigned to the specific indication of the diseased tissue is preferred for preparing a pharmaceutical composition with a specific indication, in particular a specific cancer indication.

The methods and test kits disclosed herein are preferable used for the diagnosis and/or prognosis of adverse events for patients or individuals, whereby diagnosis means diagnose of a adverse event, a predisposition for a adverse event and/or a progression of a adverse events. These adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction or damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

The methods and test kits disclosed herein are also preferable used for distinguishing cell types, tissues or for investigating cell differentiation. These serve in a particularly preferred manner for analysing the response of a patient to a drug treatment.

Methods for DNA Methylation Analysis

The following methods for the detection of the DNA methylation are all preferred embodiments of the invention. These methods allow for determination of the methylation state of one or a plurality of CpG dinucleotides (e.g., CpG islands) within a DNA sequence. Such methods involve, among other techniques, the DMH method, DNA sequencing of bisulfite-treated DNA, a number of PCR based methylation assays, some of them—known as COBRA, MS-SNuPE, MSP, nested MSP, HEAVYMETHYL™, METHYLIGHT™ and QM assay—are described in more detail now:

DMH METHOD. The DMH method is carried out according to the invention as it is described in principle in Huang et al. (Huang et al., Hum Mol Genet, 8:459-470, 1999), in U.S. Ser. No. 09/497,855, in DE 102005007185.6, in DE102005025 240.0, in DE102005036500.0, or in U.S. 60/710,556 (all incorporated by its entirety). According to these, genomic DNA is fragmented by restriction endonucleases before it is subject to a DNA microarray of cloned CpG islands.

But the DMH method may also include several improvements: After isolation of the DNA, an enrichment of methylated or unmethylated DNA takes place by different means. This means can be one or more of the following: for example restriction endonucleases or proteins, peptides or oligomers which specially bind to CpG dinucleotide either specific on methylated or on non-methylated CpG dinucleotides. Four variants of enrichment by means of restriction endonucleases are especially preferred:

The enrichment by use of only methylation specific restriction enzymes without a previous addition of non-methylation specific restriction enzymes but with a subsequent selective amplification of fragments in the range of 50-5.000 bp via linker (also known as adapters by those skilled in the art). Preferred restriction enzymes are of the group "BisI, BstUI, BshI2361, AccII, BstFNI, McrBC, MvnI, HpaII (HapII), HhaI, AciI, SmaI, HinP1I, HpyCH4IV and mixtures of two or more of the aforesaid enzymes".

Another enrichment is performed by at first, the restriction of DNA by one or more non-methylation specific restriction enzymes; secondly, fragments smaller than 50 bp are discarded and subsequently linker are ligated on each end of every fragment; thirdly, the fragments provided with linker are subject to a restriction by one or more methylation specific restriction enzymes; and fourthly, the resulted fragments are subjected to an amplification, wherein only fragments are amplified which are not restricted in step three. According to this procedure fragments of 50-5.000 bp are enriched. It is thereby preferably that three different methylation specific restriction enzymes are used, one or more of the methylation specific restriction enzymes have a restriction site in the length of 4 bp, in particular which do not contain any CG. The non-methylation specific restriction enzymes are selected from the group "MseI, BfaI, Csp6I, Tru1I, Tvu1I, Tru9I, Tvu9I, MaeI, XspI and mixtures of two or more of the aforesaid enzymes". Preferably a mixture of MseI, BfaI and Csp6I is used. The methylation specific restriction enzymes can be any enzyme which either cuts methylation specifically unmethylated or methylated DNA. Preferably the methylation specific enzyme is selected from the group of "BisI, BstUI, BshI2361, AccII, BstFNI, McrBC, MvnI, HpaII (HapII), HhaI, AciI, SmaI, HinP1I, HpyCH4IV, EagI and mixtures of two or more of the aforesaid enzymes". In particular the use of BstUI, HpaII, HpyCH4IV and HinP1I is preferred.

Besides that, an enrichment is also possible according to the method of "NotI representation" as exemplified in WO02/086163. According to this, DNA is restricted by suitable enzymes like BamHI of BglII. After inactivation of the enzymes, the fragments are circularized by self ligation, before they are subject to another restriction by NotI which only cut its unmethylated recognition side. Through this, fragments with only unmethylated NotI recognition sites are linearised onto which specific linker are ligated. Therefore it is possible to amplify those fragments. In principle this method can also be adjusted to other methylation specific restriction enzymes as listed above.

As the fourth procedure of enrichment by the means of restriction endonucleases, the MS AP-PCR (Methylation Sensitive Arbitrarily-Primed Polymerase Chain Reaction) is preferred. This technique is well known in the art and was described the first time by Gonzalgo et al., Cancer Res., 57:594-599, 1997. In principle, genomic DNA is subject to an restriction digestion, for example HpaII. The resulting fragments are then subject to an amplification wherein random primers are used which are rich in CG dinucleotides. According to this, DNA regions are amplified which are rich in CG dinucleotides.

An enrichment of methylated or non-methylated DNA can also occur by means of proteins, peptides or oligomers which specifically bind to methylated or non-methylated DNA. The binding can be sequence specific or unspecific. However, unbound DNA is separated by bound DNA through the binding. Depending on which kind of DNA is of interest, methylated or non-methylated DNA, or which kind of DNA is bound, the bound or unbound DNA fraction is further analysed. These means proteins may be used which specifically bind unmethylated DNA, as well as proteins which specifically bind methylated DNA. Furthermore, it is possible to bind that DNA, which is later analysed. Therefore the unbound DNA is removed before the bound DNA is released from the protein. On the other hand it is also possible to let bind the background DNA to the proteins and thereby it is removed from the reaction mixture. Of course, it is also possible to carry out such an enrichment in two subsequent steps whereby the order is not relevant. In one step, proteins which specifically bind unmethylated DNA and in the other step, proteins which specifically bind methylated DNA are used. Such a proceeding has the advantage that simultaneously unmethylated DNA and methylated DNA are enriched while DNA with no or only a view CpG positions is removed.

An enrichment can be achieved by proteins which methylation specifically bind to DNA and also by the use of their domains or peptides. Such proteins can be for example MeCP2, MBD1, MBD2, MBD4 and Kaiso. The later binds sequence specifically namely on symmetrical methylated CpGpCpG positions. Exemplary the Methyl-CpG-binding domain of MeCP2 protein or the CXXC-3 domain of the MBD1 protein is mentioned as suitable domains for enrichment (for an overview: Shiraishi et al., Anal Biochem. 2004 Jun. 1; 329 (1):1-10; Hendrich and Tweedie, Trends Genet.

2003 May, 19 (5): 269-77; Jorgensen et al., Molecular and Cellular Biology, 2004, 3387-3395; all incorporated by its entirety).

Typically, the proteins, domains or peptides are bound to a solid surface for example on beads which enable a separation of by means of a batch procedure or by a column chromatography (Cross et al., Nature Genetics, 1994 (6) 236-244; Shiraishi et al., Anal Biochem. 2004 Jun. 1; 329 (1):1-10). Biochemical Methods which have to be applied are known to those skilled in the art. This may for example include the use of biotin or histidine tags (for example Gretch et al., Anal Biochem., 1987, (163) 270-7; Janknecht et al., Prc Nat. Acad Sci, 1991, (88) 8972-6).

Moreover, an enrichment can also be achieved by methylation specific antibodies for example by means of the anti 5-methylcytosine antibody available from Abcam Inc. Again the enrichment can be performed in a batch procedure or by column chromatography. Details are known to persons skilled in the art (for example: Fisher et al., Nucleic Acids Res. 2004, 32(1), 287-97). On the hand, an enrichment can also be achieved by immunoprecipitation with methylation specific antibodies and suitable secondary antibodies, followed by a proteinase K treatment.

Another variant of enrichment is the chromatin immunoprecipitation (ChIP). Details are known to those skilled in the art (for example: Matarazzo et al., Biotechniques, 2004, 37(4), 666-8, 670, 672-3.) According to this, a immunoprecipitation is carried out with antibodies which are specific for 5-methylcytosine binding proteins like MeCP2, MBD1, MBD2, MBD4 or Kaiso. Thereby the proteins are fixed onto the DNA before the antibodies are added. In particular it is preferred to purify the DNA first and then add the DNA binding proteins. It is also particularly preferred to apply a suitable physical method like ultracentrifugation before the second precipitation step. A suitable kit is available from Panomics, Inc.

Furthermore, an enrichment can be achieved by triplex binding oligomers, which can PNA- or DNA-Oligomers. This method is described in detail in WO04/113564. In principle, a triplex-building oligomer is brought in contact with DNA. Thereafter it preferentially forms a triple helix with unmethylated DNA in comparison to methylated DNA. From this advantage is taken for enrichment.

In principle, a DNA may be fragmented randomly or non-randomly before it is subject to enrichment by any method using proteins, peptides or oligomers. This is done as it is known by those skilled in the art. Fragmentation can be performed randomly for example with sonification or shearing. But is also can be performed non-randomly, preferentially by the use of methylation specific restriction endonucleases, in particular of the group of "BisI, BstUI, BshI2361, AccII, BstFNI, McrBC, MvnI, HpaII (HapII), HhaI, AciI, SmaI, HinP1I, HpyCH4IV and any mixture of two or more of the aforesaid enzymes".

A further reduction of complexity can be achieved by physical methods which are applied before or after an amplification. Such physical methods can for example be gel electrophoresis, size-exclusion chromatography or filtration.

After enrichment of the DNA, the fragments are labelled preferentially with a suitable fluorescent dye. Such a dye enables selective one or two dimensional scanning. Typically Cy3 and/or Cy5 are used as dyes. But also other suitable dyes are known to those skilled in the art. Furthermore, it is preferred that the fragments are labelled with biotin, which interacts with another substance in the actually detection process. Thereby it is necessary to carry out two arrays which are compared with each other.

The labelling is carried out preferentially by means of an amplification, in particular whole genome amplifications. Several suitable methods are known by those skilled in the art.

The labelled fragments are then subject to a DNA microarray which can be either a array of cloned CpG islands or array of oligonucleotides. The oligonucleotides of the oligonucleotide microarray can be any oligonucleotide suitable for the detection of methylation or non-methylation of CpG dinucleotides. Preferably the oligonucleotides are design after fragments derived according to the following two strategies:

According to the first strategy, A) the genome of an organism of desire is analysed for first fragments, which are flanked by recognition sites of non-methylation specific restriction enzymes of interest and which are in the range of 100-1.200 bp. B) Second fragments are then selected under those first fragments which have no more than 50%, preferably no more than 20% of repeats. These two steps A) and B) can be performed in arbitrary order. Additionally, C) the second selected fragments are analysed for the presence of recognition sites of methylation specific restriction endonucleases of interest. Those second fragments which include such a recognition site are then selected as third fragments. Again, the steps A), B) and C) can be performed in arbitrary order.

According to the second strategy, A) the genome of an organism of desire is analysed for first fragments, which are flanked by recognition sites of methylation specific restriction enzymes of interest and which are in the range of 100-1.200 bp. B) Second fragments are then selected under those first fragments which have no more than 50%, preferably no more than 20% of repeats. C) The second selected fragments are analysed for the presence of recognition sites of methylation specific restriction endonucleases of interest. Those second fragments which include such a recognition site are then selected as third fragments. Again, the steps A), B) and C) can be performed in arbitrary order.

Fragments selected according to these strategies can match fragments obtained by the enrichment procedures. The sequence of the oligonucleotides of the array is chosen from the selected fragments, so that they would hybridise to the selected fragments or so that they are identical to them and therefore would hybridise to the counter strand. These oligonucleotides are then synthesised on the array or are linked to it after the synthesis. Typically 3-30 oligonucleotides are derived from one fragment, whereby it is possible that the oligonucleotide sequences are overlapping. Preferably the oligonucleotides have a defined distance between each other so that a so called "tiling array" results, similar as described by Kapranov et al., Science, 2002, 296(5569):916-9.

According to the DMH method, fragments hybridized on the immobilized oligonucleotides contain preferably nucleic acid sequences, which methylation positions are non-methylated or methylated in case of a definite disease in comparison to the normal condition. The oligonucleotides do not have to necessarily encode for the methylation positions by themselves, although it is possible. Moreover, it is possible that a oligonucleotide array carries different sets of oligonucleotides, suitable for the detection of different diseases or of predispositions for a disease or of the susceptibility for side effects for a definitive medical treatment. Additionally, it is also possible to predict the type, the aggressiveness or the progression of a disease or for the effectiveness of a medical treatment, in case it is based on methylation differences. Further conclusions can be made by comparison of the results obtained by means of an oligonucleotide array according to the DMH method with a results obtained with arrays with different oligonucleotide set, for example oligonucleotide sets suitable for SNP analysis.

BISULFITE SEQUENCING. DNA methylation patterns and 5-methylcytosine distribution can be analyzed by sequencing analysis of a previously amplified fragment of the bisulfite treated genomic DNA, as described by Frommer et al. (Frommer et al. Proc. Natl. Acad. Sci. USA 89:1827-1831, 1992). As the bisulfite treated DNA is amplified before sequencing, the amplification procedure according to the invention may be used in combination with this detection method.

COBRA. COBRA analysis is a quantitative methylation assay useful for determining DNA methylation levels at specific gene loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992) or as described by Olek et al (Olek A, Oswald J, Walter J. (1996) Nucleic Acids Res. 24: 5064-6). PCR amplification of the bisulfite converted DNA is then performed using methylation unspecific primers followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Additionally, restriction enzyme digestion of PCR products amplified from bisulfite-converted DNA is also used, in the method described by Sadri & Hornsby (Nucl. Acids Res. 24:5058-5059, 1996)

The bisulfite conversion and amplification procedure according to the invention may be used in combination with this detection method.

Ms-SNuPE (Methylation-sensitive Single Nucleotide Primer Extension). The Ms-SNuPE technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

The bisulfite conversion and amplification procedure according to the invention may be used in combination with this detection method.

MSP. MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA.

MSP primer pairs contain at least one primer, which hybridizes to a bisulfite treated CpG dinucleotide. Therefore, the sequence of said primers comprises at least one CpG dinucleotide. MSP primers specific for non-methylated DNA contain a "T" at the 3' position of the C position in the CpG. Preferably, therefore, the base sequence of said primers is required to comprise a sequence having a length of at least 9 nucleotides which hybridizes to the bisulfite converted nucleic acid sequence, wherein the base sequence of said oligomers comprises at least one CpG dinucleotide. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes. The bisulfite conversion and amplification procedure according to the invention may be used in combination with this detection method.

NESTED MSP (Belinsky and Palmisano in US application 20040038245). Considering the apparent conflict of requiring high specificity of the MSP primer to sufficiently differentiate between CG and TG positions but allowing for a mismatch in order to create a unique restriction site it is preferred to use an amended version of MSP, known as nested MSP, as described in WO 02/18649 and US patent application 20040038245 by Belinsky and Palmisano. This method to detect the presence of gene-specific promoter methylation, comprises the steps of: expanding the number of copies of the genetic region of interest by using a polymerase chain reaction to amplify a portion of said region where the promoter methylation resides, thereby generating an amplification product; and using an aliquot of the amplification product generated by the first polymerase chain reaction in a second, methylation-specific, polymerase chain reaction to detect the presence of methylation. In other words a non methylation specific PCR is performed prior to the methylation specific PCR. The bisulfite conversion and amplification procedure according to the invention may be used in combination with this detection method.

HEAVYMETHYL™. (WO 02/072880; Cottrell S E et al. Nucleic Acids Res. 2004 Jan. 13; 32(1):e10) A further preferred embodiment of the method comprises the use of blocker oligonucleotides. In the HEAVYMETHYL™ assay blocking probe oligonucleotides are hybridized to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridize to the bisulfite treated nucleic acid in a methylation status specific manner. For example, for detection of methylated nucleic acids within a population of unmethylated nucleic acids, suppression of the amplification of nucleic acids which are unmethylated at the position in question would be carried out by the use of blocking probes comprising a 'CpA' or 'TpA' at the position in question, as opposed to a 'CpG' if the suppression of amplification of methylated nucleic acids is desired.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivatized at the 3' position with other than a "free" hydroxyl group. For example, 3'-O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-termini thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker—a process that normally results in degradation of the hybridized blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

Preferably, therefore, the base sequence of said blocking oligonucleotide is required to comprise a sequence having a length of at least 9 nucleotides which hybridizes to the chemically treated nucleic acid sequence, wherein the base sequence of said oligonucleotides comprises at least one CpG, TpG or CpA dinucleotide.

The bisulfite conversion and amplification procedure according to the invention may be used in combination with this detection method.

Preferably, real-time PCR assays are performed specified by the use of such primers according to the invention. Real-time PCR assays can be performed with methylation specific primers (MSP-real time) as methylation-specific PCR ("MSP"; as described above), or with non-methylation specific primers in presence of methylation specific blockers (HM real-time) ("HEAVYMETHYL™", as described above). Real-time PCR may be performed with any suitable detectably labeled probes. For details see below. Both of these methods (MSP or HM) can be combined with the detection method known as METHYLIGHT™ (a fluorescence-based real-time PCR technique) (Eads et al., Cancer Res. 59:2302-2306, 1999), which generally increases the specificity of the signal generated in such an assay. Whenever the real-time probe used is methylation specific in itself, the technology shall be referred to as METHYLIGHT™, a widely used method.

Another assay makes use of the methylation specific probe, the so called "QM" (quantitative methylation) assay. A methylation unspecific, therefore unbiased real-time PCR amplification is performed which is accompanied by the use of two methylation specific probes (METHYLIGHT™) one for the methylated and a second for the unmethylated amplificate. That way two signals are generated which can be used to a) determine the ratio of methylated (CG) to unmethylated (TG) nucleic acids, and at the same time b) the absolute amount of methylated nucleic acids can be determined, when calibrating the assay with a known amount of control DNA.

METHYLIGHT™. The METHYLIGHT™ assay is a high-throughput quantitative methylation assay that utilizes fluorescence-based real-time PCR (TAQMAN®) technology that requires no further manipulations after the PCR step (Eads et al., Cancer Res. 59:2302-2306, 1999). Briefly, the METHYLIGHT™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The METHYLIGHT™ assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The METHYLIGHT™ process can by used with a "TAQMAN®" probe in the amplification process. For example, double-stranded genomic DNA is treated with sodium bisulfite and subjected to one of two sets of PCR reactions using TAQMAN® probes; e.g., with either biased primers and TAQMAN® probe, or unbiased primers and TAQMAN® probe. The TAQMAN® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TAQMAN® probe to remain fully hybridized during the PCR annealing/extension step. As the Taq polymerase enzymatically synthesizes a new strand during PCR, it will eventually reach the annealed TAQMAN® probe. The Taq polymerase 5' to 3' endonuclease activity will then displace the TAQMAN® probe by digesting it to release the fluorescent reporter molecule for quantitative detection of its now unquenched signal using a real-time fluorescent detection system.

Variations on the TAQMAN™ detection methodology that are also suitable for use with the described invention include the use of dual-probe technology (LIGHTCYCLER™) or fluorescent amplification primers (SUNRISE™ technology). Both these techniques may be adapted in a manner suitable for use with bisulfite treated DNA, and moreover for methylation analysis within CpG dinucleotides. Typical reagents (e.g., as might be found in a typical METHYLIGHT™-based kit) for METHYLIGHT™ analysis may include, but are not limited to: PCR primers for specific bisulfite sequences, i.e. bisulfite converted genetic regions (or bisulfite converted DNA or bisulfite converted CpG islands); probes (e.g. TAQ-MAN® or LIGHTCYCLER™) specific for said amplified bisulfite converted sequences; optimized PCR buffers and deoxynucleotides; and a polymerase, such as Taq polymerase.

The bisulfite conversion and amplification procedure according to the invention may be used in combination with this detection method.

The fragments obtained by means of the amplification can carry a directly or indirectly detectable label. Preferred are labels in the form of fluorescence labels, radionuclides, or detachable molecule fragments having a typical mass, which can be detected in a mass spectrometer. Where said labels are mass labels, it is preferred that the labeled amplificates have a single positive or negative net charge, allowing for better detectability in the mass spectrometer. The detection may be carried out and visualized by means of, e.g., matrix assisted laser desorption/ionization mass spectrometry (MALDI) or using electron spray mass spectrometry (ESI).

Matrix Assisted Laser Desorption/Ionization Mass Spectrometry (MALDI-TOF) is a very efficient development for the analysis of biomolecules (Karas & Hillenkamp, Anal Chem., 60:2299-301, 1988). An analyte is embedded in a light-absorbing matrix. The matrix is evaporated by a short laser pulse thus transporting the analyte molecule into the vapour phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut & Beck, Current Innovations and Future Trends, 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionization process via the matrix is considerably less efficient. In MALDI-TOF spectrometry, the selection of the matrix plays an eminently important role. For desorption of peptides, several very efficient matrixes have been found which produce a very fine crystallisation. There are now several responsive matrixes for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut & Beck, Nucleic Acids Res. 23: 1367-73, 1995). The coupling of a charge tag to this modified DNA results in an increase in MALDI-TOF sensitivity to the same level as that found for peptides.

The amplificates may also be further detected and/or analysed by means of oligonucleotides constituting all or part of an "array" or "DNA chip" (i.e., an arrangement of different oligonucleotides and/or PNA-oligomers bound to a solid phase). Such an array of different oligonucleotide- and/or PNA-oligomer sequences can be characterized, for example, in that it is arranged on the solid phase in the form of a rectangular or hexagonal lattice. The solid-phase surface may be composed of silicon, glass, polystyrene, aluminum, steel, iron, copper, nickel, silver, or gold. Nitrocellulose as well as plastics such as nylon, which can exist in the form of pellets or also as resin matrices, may also be used. An overview of the Prior Art in oligomer array manufacturing can be gathered from a special edition of Nature Genetics (Nature Genetics Supplement, Volume 21, January 1999, and from the literature cited therein). Fluorescently labeled probes are often used for the scanning of immobilized DNA arrays. The simple attachment of Cy3 and Cy5 dyes to the 5'-OH of the specific probe are particularly suitable for fluorescence labels. The detection of the fluorescence of the hybridized probes may be carried out, for example, via a confocal microscope. Cy3 and Cy5 dyes, besides many others, are commercially available.

The bisulfite conversion and amplification procedure according to the invention may be used in combination with this detection method.

Furthermore, additional methods for methylation analysis are known by persons skilled in the art. Such methods are for example methods in which bisulfite treated DNA is subject to DNA array based analysis methods as described in WO 99/28498, WO 01/38565, or in WO 02/18632.

All references cited herein are incorporated in their entirety.

EXAMPLES

Example 1 a) Paraffin Removal Step

Chemical Needed:
Limonene145, Fluka Chemika, Art Nr. 89188
Procedure:
1. Spin safe look or screw cap reaction tubes (containing 1-5 sections of a paraffin-embedded formalin-fixed tissue) for 1 min at 5,000×g
2. Add 1 ml limonene to each tube. Push all pieces into the liquid. In some cases sample material is already very brittle with small pieces of paraffin/tissue in tube—make sure that material sticking to the tube cap goes back into the tube.
3. 1 h incubation at room temperature at 1,000 rpm in thermomixer, vortex vigorously at least 3 times during incubation.
4. Place tubes into centrifuge and spin at 16,000 rcf (=16,000×g) for 5 min, the tissue will pellet at the tube bottom.
5. Use a 1 ml pipet to suck up the limonene from each sample. Great care should be taken not to disturb the pellet! Place pipet tip opposite the pellet onto the tube and gently allow limonene to enter the pipet tip; for removal of last droplets a yellow tip should be used.
6. If the tissue settles only weakly at the bottom (i.e. not forming a nice pellet) do the following:
   repeat centrifugation again for 5 min on EPPENDORF® 5417 centrifuge at max speed (>20,000 rcf)
   then repeat the removal of limonene: make sure the pipet tip is pressed against the bottom of the tube and limonene is removed very slowly such as not to suck in the tissue. Remove as much limonene as possible.

b) Lysis Step

Prepare a larger volume of the lysis buffer (0.5 or 1 l), depending on the number of samples to be processed for a project. This buffer can be stored at room temperature for 3 months. Check for contamination and carry out filter sterilization of an aliquot before each use.

Chemicals:
TRIS (tris-hydroxymethyl-amino-methan), Merck, Art. Nr. 1.01549.0500,
MW=121.14 g/mol
Prepare a 1 mol/l Stock Solution:
dissolve 121.14 g in 800 ml $H_2O$ and adjust to pH 8.0 with HCl and fill up to 1 l
EDTA (ethylendiaminetetraacetic acid),
Sodium EDTA (Titriplex III) from Merck, Art. Nr. 159294
MW=372.24 g/mol
Prepare a 0.5 mol/l stock solution: Dissolve 186.1 g in 800 ml $H_2O$ and adjust to pH 8.0 with NaOH, fill up to 1 l.
Tween (Tween 20), Fluka, Chemika Art Nr. 93773
This detergent is added to the buffer in volume percent. To add Tween to the buffer take 1 ml of Tween (in 2 ml tube), warm it at 50° C. and add desired volume to buffer with a widened pipet tip.
Lysis buffer composition: 50 mmol/l TrisHCl, pH 8.0, 1 mmol/l EDTA,
0.5% Tween (volume %)
Proteinase K, Roth
Always prepare a fresh 30 mg/ml stock solution in $H_2O$. The size of the stock solution should be adjusted to the number of samples to be processed. For example 300 mg proteinase K dissolved in 10 ml $H_2O$ will be sufficient for ~400 samples.

Procedure:
1. Add 190 µl of the prepared lysis buffer to each sample. It is important to ensure that all sample material is covered by lysis buffer.
2. Add 20 µl of the prepared proteinase K solution.
3. Vortex the tube rigorously to ensure proper mixing of sample with lysis buffer and proteinase K. Make sure the tube caps are tightly closed—otherwise loss of liquid will happen!
4. Incubate at 60° C., shaking 1,000 rpm (thermoshaker).
5. Incubate for 40 to 48 hours, no further additions of proteinase K necessary.
6. Spin in the morning and the evening of each day to remove droplets from the cap, vortex vigorously.
7. Incubate samples at >95° C. for 10 min in to order to inactive proteinase K. For this, set the thermomixer at a temperature of 99° C., since the real temperature at the highest setting is some degrees below the indicated temperature.
   (active proteinase K in the lysate will reduce PCR performance, especially if lysate is used directly for quantitation of genomic DNA by real time PCR)

Quality Check of Lysis (During Lysis)
After lysis step 5, there should be a homogeneous, maybe turbid solution in the tube with no visible pieces of tissue left. However, should there be visible pieces of tissues in MANY of the samples left after the first ON-incubation additional proteinase K step and increase of lysis volume should be considered. If only individual samples have some undigested material left this may be neglected. Have a careful look!

Storage:
Lysed samples may be stored at either −20° C. or −80° C. (depending on storage time) or be used immediately for downstream processing.

c) DNA Extraction Step

Equipment Needed:
plate centrifuge (Sigma or QIAGEN®, capable of up to 5,758×g (6,000 rpm))
pipettors for volumes of from 10 µl to 1,000 µl (multichannel for large volumes)
waste container for DNA flowthrough (e.g. bowl with DNA-off)
Material Needed:
DNEASY® 96 Tissue Kit (QIAGEN® #69581 or 69582)
pipet tips (100 µl, 1,000 µl)
15 ml and 50 ml Falcon tubes
Chemicals Needed:
ethanol, molecular biology grade
Procedure:
Make sure by respective labeling, that all plates in an assembly are turned in the same direction (well A1 over well A1 etc.).

1. Distribute 400 µl AL/E in collection microtubes and transfer lysate (200 µl) to the tubes; seal tubes with caps for collection tubes; use plate lid to fix tubes in rack
2. Mix by shaking 15 s with BOTH hands; spin shortly (let centrifuge reach 1,450×g and stop);
3. Place the DNEASY® 96 plate on an S-block (seal unused wells of DNEASY® plate with AIRPORE™ Tape sheet). Carefully apply the mixture from step 2 onto columns. Seal with AIRPORE™ Tape. Centrifuge at 5,790×g for 10 min. If there's still fluid visible on membranes, add centrifugation step.
4. Remove the tape. Add 500 µl AW1. Seal with new AIRPORE™ Tape sheet. Empty S-block. Spin for 5 min at 5,790×g.
5. Remove the tape. Add 500 µl AW2. Seal with new AIRPORE™ Tape sheet. Empty S-block. Spin for 15 min at 5,790×g, this should leave the membrane dried.
6. Place DNEASY® plate on elution microtube plate. To elute DNA add 120 µl buffer AE or dd$H_2O$ preheated to 70° C. to each well. Seal the plate with a new AIRPORE™ Tape sheet. Incubate for 5 min at room temperature. Spin for 2 min at 5,790×g.
7. Seal elution microtubes with caps provided. Store at −20° C. or −80° C. (depending on storage time)

d) Bisulfite Treatment Step and e) DNA Purification Step

Equipment Needed:
Thermocycler (e.g. EPPENDORF®, Tetrad)
Plate centrifuge (Sigma or QIAGEN®, capable of up to 5,700×g)
Pipettors for volumes of from 10 µl to 1,000 µl (multichannel EPPENDORF®+Matrix pipettors)
Material Needed:
PCR-plates+cap strips
QIAAMP® 96 DNA Blood Kit (QIAGEN® #51161 for 4 plates or 51162 for 12)
Additional round well blocks and caps (1 needed additional for each purification of 96 samples; #19576 for 24 plates)
QIA Buffer AVL (#19073 for 155 ml, 560 µl per sample needed)

pipet tips (100 µl, 1,000 µl, EPPENDORF®+Matrix)
15 ml and 50 ml Falcon tubes
waste container for DNA-flowthroughs (e.g. bowl with DNA-off)
Chemicals Needed:
sodium bisulfite ($Na_2S_2O_5$, 190.1 g/mol), Merck 1.06528.0500
sodium sulfite, anhydrous ($Na_2SO_2$, 126.04 g/mol), Fluka 71988
dd$H_2O$ molecular biology grade (0.2 µm filtered, DEPC-treated, autoclaved, free of DNases- and RNases)
diethyleneglycoldimethylether (DME), Merck 8.02934.0250
6-hydroxy-2,5,7,8-tetramethylchroman-2-carboxylic acid (250.29 g/mol), Aldrich 23, 881-3
ethanol, molecular biology grade
sodium hydroxide pellets (NaOH, 40.0 g/mol), Merck 1.06482.1000

Preparation of Solutions (Sufficient for 80 Reactions, Always to be Prepared Freshly!):

Bisulfite solution: Sodium disulfite (4.708 g) and sodium sulfite (1.128 g) are dissolved by adding 10 ml dd$H_2O$ (the solution is 4.9 M). The final volume is around 12 ml. Check pH of the solution—if it is not between 5.45 and 5.5, discard solution and repeat preparation. Shake rigorously and if needed, heat the solution to 50° C. in a waterbath than vortex at maximum speed for 30 sec. Repeat this procedure as often until the salt is completely dissolved.

DME-radical scavenger solution: Dissolve 125.3 mg of 6-hydroxy-2,5,7,8-tetramethyl-chroman-2-carboxylic acid by adding 1.0 ml DME. Vortex rigorously in order to ensure that no undissolved particles remain. DME is hazardous and potentially carcinogenic. Therefore take appropriate precautions when handling this chemical. If only few samples are to be bisulfite treated, prepare smaller volumes.

Desulfonation buffer: Dissolve 0.8 g sodium hydroxide in 10 ml dd$H_2O$ to prepare a 2 mol/l stock-solution. For the desulfonation buffer mix 1.0 ml 2 mol/l sodium hydroxide and 9.0 ml ethanol. The solution has to prepared freshly before each purification!

Procedure Bisulfite Reaction (Final Volume of 140 µl):

Pipet the following solutions into PCR-plates in the order shown.

1. 44 µl buffer/water containing the DNA to be bisulfite treated
2. 83 µl bisulfite solution (pipetting of bisulfite and sample can be interchanged)
3. 13 µl DME solution, containing the radical scavenger
4. mix thoroughly
5. place in 0.2 ml wells of thermocycler. Use cap-strips to close wells!

Temperature Program in a Thermocycler
5:00 min denaturation of DNA at 99° C.
22:00 min incubation at 60° C.
3:00 min denaturation of DNA at 99° C.
1:27:00 hours incubation at 60° C.
3:00 min denaturation of DNA at 99° C.
2:57:00 hours incubation at 60° C.
cooling at 20° C.

DNA purification by using a combination of QIAAMP® Viral RNA Mini Kit and QIAAMP® 96 DNA Blood Kit:

1. Preparation of Binding Buffer AVL
   Add 1 ml of buffer AVL to 310 µg of lyophilized carrier RNA. Dissolve thoroughly.
   Transfer to the buffer AVL bottle (30 ml), and mix thoroughly before using buffer AVL for the first time.
   This buffer can be stored at 2-8° C. for future use up to 6 months. However, if a precipitate develops, then redissolve by heating at 80° C. no longer than 5 min. This should be done no more than a total of 6 times. Cool to room temperature before use. An aliquot of prepared buffer AVL can also be stored at room temperature for up to 2 weeks.

Figure 22:
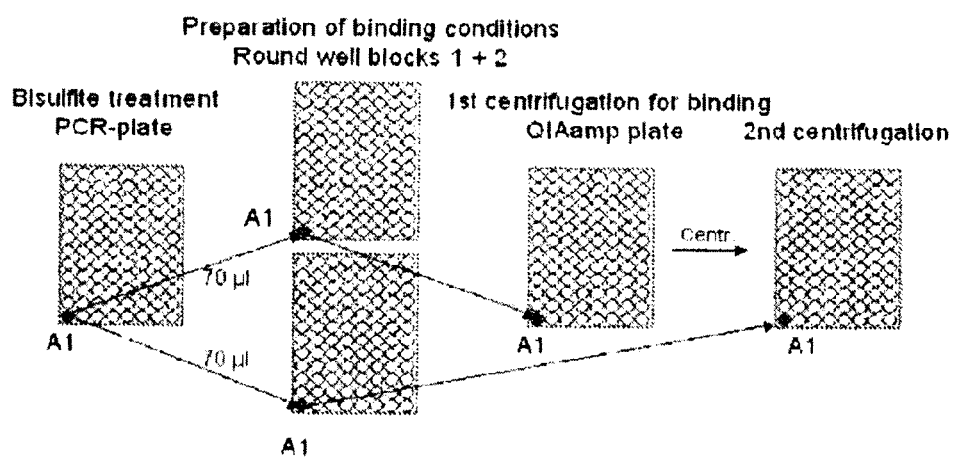
FIG. 22 schematically depicts the preparation of binding conditions in the DNA purification procedure using a combination of QIAAMP® Viral RNA Mini Kit and QIAAMP® 96 DNA Blood Kit.

2. Preparation of Binding Conditions
   For each sample two wells have to be used; these should be on 2 round well blocks in order to keep the original layout (e.g. well A1 of bisulfite plate will be split into 70 µl in well A1 block 1 and 70 µl in well A1 block 2, see FIG. 22).
   Into each well of blocks pipet 280 µl of prepared buffer AVL/carrier RNA.
   Add 70 µl DNA/bisulfite solution from PCR-plate, place DNA directly into buffer and pipet up and down 3 times to ensure complete transfer of DNA and mixing.
   Add 280 µl Ethanol. Seal the wells by using caps for blocks. Mix vigorously for at least 15 sec. (Ethanol tends to refuse to mix with fluids based on water.)
   Alternatively, if DNA amounts are very critical: Pipet only 200 µl into blocks, use remaining 80 µl to wash wells of bisulfitation-plate after transfer of DNA.
   Spin briefly at 1,450×g (reach 1,450×g and stop) to get the drops down. Incubate at room temperature for 10 minutes.

3. Binding
   Both wells are loaded subsequently onto ONE column (see illustration above)
   Place QIAAMP® 96 plate on top of an S-block
   apply 630 µl of the first well per sample QIAAMP® 96 plate
   Seal plate with a AIRPORE™ Tape sheet, spin at 5,790×g for 4 min
   Empty the S-block
   Repeat binding with second well of each sample onto the same column like first well (load, seal, spin, empty S-block)

4. Washing and 5. Desulfonation
   Place QIAAMP® 96 plate of S-block
   Add 500 µl buffer AW1
   Seal the plate with new AIRPORE™ Tape sheet
   Spin at 5,790×g for 2 min
   Empty S-block, place plate on S-block
   Add 500 µl 0.2 mol/l NaOH to the QIAAMP® 96 plate
   Seal with a fresh AIRPORE™ Tape sheet, incubation for 15 min at room temperature.
   Centrifuge at 5,790×g for 1 min.
   Empty S-block
   add 500 µl AW2
   Seal the plate with new AIRPORE™ Tape sheet
   Spin at 5,790×g for 15 min 6. Elution
   Place QIAqmp 96 plate on rack of elution microtubes.
   Add 100 µl AE or dd$H_2O$ preheated to 70° C.
   Seal plate with a new AIRPORE™ sheet and incubate at room temperature for 5 min
   Spin at 5,790×g for 4 min
   Seal tubes with caps The DNA can then be further amplified and analysed by means of the sensitive methods for DNA methylation analysis.

Example 2

All steps will be done in the tubes that the samples are provided in, i.e. the tubes provided by the supplier of the samples, these can be both 1.5 and 2.0 ml (preferred) tubes. Please double check that tube formats fit into the centrifuge.

The solvents and buffers can be delivered with either single channel pipettes or multipettes a) Removal of Paraffin

Chemical Needed:
Limonene145, Fluka Chemika, Art Nr. 89188
Procedure:
1. Add 1 ml limonene to each tube (containing 1 to 5 slides of paraffin-embedded formalin-fixed surgery sample). Push all pieces into the liquid. In some cases sample material is already very brittle with small pieces of paraffin/tissue in tube—make sure that material sticking to the tube cap goes back into the tube.
2. 1 h incubation at room temperature at 1,000 rpm, vortex vigorously at least 3 times during incubation.
3. Place tubes into centrifuge and spin at 16,000 rcf (=16,000×g) for 5 min, the tissue will pellet at the tube bottom.
4. Use a 1 ml pipet to suck up the limonene from each sample. Great care should be taken not to disturb the pellet! Place pipet tip opposite the pellet onto the tube and gently allow limonene to enter the pipet tip, in some cases it can be easier to remove the entire volume in two rather than one pipetting steps. It is o.k. if small amounts (up to 50 µl) of limonene remain in tube.
5. If the tissue settles only weakly at the bottom (i.e. not forming a nice pellet) do the following:
repeat centrifugation again for 5 min on EPPENDORF® 5417 centrifuge at max speed (>20,000 rcf)
then repeat the removal of limonene: make sure the pipet tip is pressed against the bottom of the tube and limonene is removed very slowly such as not to suck in the tissue. Remove as much limonene as possible.
Leave out ethanol step, if it was possible to remove nearly all limonene (if there are 50 µl left, this will be ok)
6. Add 1 ml of ethanol (purity>99%).
7. Vortex, 10 min incubation at room temperature at 1,000 rpm.
8. Place tubes into centrifuge and spin at 16,000 rcf for 5 min, the tissue will pellet again at the tube bottom.
9. Use pipet to suck up the ethanol, great care should be taken not to disturb the pellet! Place pipet tip opposite the pellet onto the tube wall and gently allow ethanol to enter the pipet tip.
10. Remove as much of ethanol as possible with the pipet.
11. Residual ethanol not removed by pipetting must be evaporated by incubation in a thermomixer at 50° C. This may take between 10 to 30 min, but take care not to overdry the samples.
No drying needed, if ethanol step was left out.

b) Lysis Step

Prepare a larger volume of the lysis buffer (0.5 or 1 l), depending on the number of samples to be processed for a project. This buffer can be stored at room temperature for 3 months. After this time it is prudent to prepare a fresh buffer.
Chemicals:
TRIS (tris-hydroxymethyl-amino-methan), Merck, Art. Nr. 1.01549.0500,
MW=121.14 g/ml
Prepare a 1 Mol/l Stock Solution:
Dissolve 121.14 g in 800 ml $H_2O$ and adjust to pH 8.0 with HCl and fill up to 1 l.
EDTA (ethylendiaminetetraacetic acid),
Sodium EDTA (Titriplex III) from Merck, Art. Nr. 159294
MW=372.24 g/mol
Prepare a 0.5 Mol/l Stock Solution:
Dissolve 186.1 g in 800 ml $H_2O$ and adjust to pH 8.0 with NaOH, fill up to 1 l.
Tween (Tween 20), Fluka, Chemika Art Nr. 93773
This detergent is added to the buffer in volume percent. To add Tween to the buffer take 1 ml of Tween (in 2 ml tube), warm it at 50° C. and add desired volume to buffer with a widened pipet tip.
Lysis Buffer Composition:
50 mmol/l TrisHCl, pH 8.0, 1 mmol/l EDTA, 0.5% Tween (volume %)
Proteinase K, Roth
Prepare a 30 mg/ml stock solution in $H_2O$. The size of the stock solution should be adjusted to the number of samples to be processed. For example: 300 mg proteinase K dissolved in 10 ml $H_2O$ will be sufficient for ~400 samples.
Proteinase K can be stored at 4° C. for up to one week safely. If more samples will be processed it is recommended to prepare fresh solutions repeatedly.
Procedure:
1. Add 190 µl of the prepared lysis buffer to each sample. It is important to ensure that all sample material is covered by lysis buffer.
2. Add 20 µl of the prepared proteinase K solution.
3. Vortex the tube rigorously to ensure proper mixing of sample with lysis buffer and proteinase K. Make sure the tube caps are tightly closed—otherwise loss of liquid will happen!
4. Incubate at 50° C., shaking 1,000 rpm (thermoshaker).
5. Incubate for 40 to 48 h, no further additions of Proteinase K necessary.
6. Spin in the morning and the evening of each day to remove droplets from the cap, vortex vigorously.
Quality Check of Lysis (During Lysis):
After these lysis steps, there should be a homogeneous, maybe turbid solution in the tube with no visible pieces of tissue left. However, should there be visible pieces of tissues in MANY of the samples left after the first ON-incubation additional proteinase K step and increase of lysis volume should be considered. If only individual samples have some undigested material left this may be neglected. Have a careful look!
7. Incubate samples at >95° C. for 10 min in to order to inactive proteinase K. For this set the temperature of the thermomixer at 99° C., since the real temperature at the highest setting is some degrees below the indicated temperature. (Active proteinase K in the lysate will reduce PCR performance, especially if lysate is used directly for quantitation of genomic DNA by RT-PCR).
8. Lysed samples may be stored at either −20° C. or −80° C. (depending on storage time) or be used immediately for downstream processing.

c) DNA Extraction with QIAGEN® DNEASY® Tissue Kit

Approximate Duration for 30 Samples:
Preparation of devices and materials: 15 min; Preparation: 30 min; Procedure: 1.5 h
The Following Devices are Needed:
centrifuge, e.g. model EPPENDORF® 5417R; EPPENDORF® pipettes and/or Multipettes; 1.5 ml and 2 ml reaction-tubes; thermomixer.

The Following Reagents are Needed:
paraffin sample lysates (~210 µl or more, if lysis buffer+proteinase K were added, the actual volumes may differ slightly, lower volumes may occur because aliqots were taken for quantitation, evaporation loss. Also larger volume may occur because lysed tissue amount was more than average)

Ethanol for molecular biology (96-100%)

DNEASY® kit (QIAGEN® cat nr. 69504 [50 columns] or 69506 [250 columns])

Preparation (Before Starting the Actual Extraction):
1. Mix buffer AL thoroughly by shaking before use. Buffer AL is stable for 1 year when stored at room temperature. If a precipitate has formed in buffer AL, dissolve by incubating at 70° C.
2. Buffer AW 1 is supplied as a concentrate. Add the appropriate amount of ethanol (96-100%) before first use (these amounts differ for the 69504 and 69506 kits, respectively). Buffer AW 1 is stable for 1 year when stored closed at room temperature.
3. Buffer AW 2 is supplied as a concentrate. the appropriate amount of ethanol (96-100%) before first use (these amounts differ for the 69504 and 69506 kits, respectively). Buffer AW 2 is stable for 1 year when stored closed at room temperature.
4. If samples were frozen after tissue lysis make sure the samples are equilibrated to room temperature.
5. Heat a thermomixer to 70° C.
6. All centrifugation steps should be carried out at room temperature.
7. Be careful not to cause spills when using the Multipette instead of single pipettors.

Extraction Procedure:
1. Add 210 µl (if lysate had a larger volume: 1 volume of lysis buffer+proteinase K volume used) of buffer AL to the tube (1.5 or 2.0 ml) containing the lysate, mix thoroughly by vortexting. Place tube into a thermomixer and incubate at 70° C., shaking at 1,000 rpm for 10 min.
2. Add 210 µl (if lysate had a larger volume: again 1 volume of lysis buffer+proteinase K volume used) ethanol (96-100%) to the sample, and mix by pulse-vortexing for 15 sec. After mixing, briefly centrifuge the tube to remove drops from the inside of the lid.
3. Carefully apply the mixture from step 2 (up to 700 µl will fit into the column, include precipitates!) onto a DNEASY® spin column which is already placed into a 2 ml collection tube (QIAGEN® provided) without wetting the rim. Close the cap, and centrifuge at 6,000×g (=rcf, or 8,000 rpm) for 1 min. Place the DNEASY® spin column in a clean 2 ml collection tube (QIAGEN® provided), and discard the tube containing the filtrate.
4. If lysates were larger than 210 µl the column has be loaded a $2^{nd}$ time: place into a fresh 2 ml tube, add remaining volume of the mixture from step 2, spin like in step 3
5. Carefully open the spin column and add 500 µl buffer AW 1 (this stays the same for large lysates, too) without wetting the rim. Close the cap and centrifuge at 6,000×g for 1 min. Place the spin column in a clean 2 ml collection tube (provided), and discard the collection tube containing the filtrate.
6. Carefully open the spin column and add 500 µl Buffer AW 2 without wetting the rim. Close the cap and centrifuge at full speed 20,000×g (14,000 rpm) for 3 min.
7. Optional: Discard the filtrate. In order to avoid carry over of ethanol, new tubes (not provided by QIAGEN®) should be used. Centrifuge again for 1 min at 20,000×g (14,000 rpm).
8. Place the DNEASY® spin column in a clean and already labeled 1.5 ml reaction-tube (not provided by QIAGEN®), and discard the collection tube containing the filtrate. Carefully open the DNEASY® spin column and add 60 µl of elution buffer AE (at room temperature) to the center of the column. Incubate at room temperature for 1 min, then centrifuge at 6,000×g (8,000 rpm) for 1 min. Add again 60 µl of new elution buffer to the column center, incubate for 1 min and centrifuge at 6,000×g for 1 min using the same tube. Final volume is 120 µl (sufficient for 2 bis-reactions with new protocol), though some loss may occur due to liquid retention on column.

If final DNA concentration is not critical, also larger elution volumes can be chosen (volumes to be defined project-specifically!)
9. If samples are used for bisulfite treatment within the next 2 days keep them at +4° C. in a fridge. For long term storage −20° C. is recommended.

Analysis:
An aliqot of the eluate (3 µl) is used to quantiate the DNA concentration using a genomic real time PCR assay. UV quantitation is optional.

d) Bisulfite Treatment and e) DNA Purification with MICROCON™ Device

Equipment Needed:
thermo cycler (e.g. EPPENDORF®, Tetrad)
centrifuge (capable of up to 14,000×g)
pipettors for volumes of 100 µl and 1,000 µl
Material Needed:
MICROCON™ Centrifugal Filter devices, MICROCON™ YM-30 (MILLIPORE®/AMICON® 42410)
pipet tips (100 µl, 1,000 µl)
200 µl PCR-tubes (e.g. EPPENDORF® 0030 124.359)
1.5 ml tubes (e.g. EPPENDORF® 0030 120.086)
15 ml and 50 ml Falcon tubes
Chemicals Needed:
sodium bisulfite ($Na_2S_2O_5$, 190.1 g/mol), Merck 1.06528.0500
sodium sulfite, anhydrous ($Na_2SO_2$, 126.04 g/mol), Fluka 71988
ddH$_2$O molecular biology grade (0.2 µm filtered, DEPC-treated, autoclaved, free of DNases- and RNases)
diethyleneglycoldimethylether (DME), Merck 8.02934.0250
6-hydroxy-2,5,7,8-tetramethylchroman-2-carboxylic acid (250.29 g/mol), Aldrich 23, 881-3
Tris-hydroxymethyl-aminomethan ($C_4H_8O_2$, M=121.14 g/mol), Merck 1.01549.0500
sodium hydroxide pellets (NaOH, 40.0 g/mol), Merck 1.06482.1000
EDTA (Titriplex® III, $C_{10}H_{24}N_2O_8Na_2$ 2H$_2$O, 372.24 g/mol). Merck 1.08418.0250

Preparation of Solutions (Sufficient for 80 Reactions):
Bisulfite solution: Sodium disulfite (4.708 g) and sodium sulfite (1.128 g) are dissolved by adding 10 ml ddH$_2$O (the solution is 4.9 M). The final volume is around 12 ml. Check pH of the solution—if it is not between 5.45 and 5.5, discard solution and repeat preparation. Shake rigorously and if needed, heat the solution to 50° C. in a waterbath than vortex at maximum speed for 30 sec. Repeat this procedure as often until the salt is completely dissolved.

DME-radical scavenger solution: dissolve 125.3 mg of 6-hydroxy-2,5,7,8-tetramethyl-chroman-2-carboxylic acid by adding 1.0 ml DME. Vortex rigorously in order to ensure that no undissolved particles remain. DME is hazardous and potentially carcinogenic. Therefore take appropriate precautions when handling this chemical. If only few samples are to be bisulfite treated, prepare smaller volumes.

NaOH 0.2 mol/l: Dissolve 0.32 g sodium hydroxide in 40 ml ddH$_2$O. TE buffer: 10 mmol/l Tris/0.1 mmol/l EDTA, pH 8

General:

This procedure is designed to be applied in 200 µl PCR-tubes. The total number of samples is limited by the number of tubes that can be handled in the thermocyclers, centrifuges, etc.

The working solutions should not be stored over prolonged periods of time. It is best to prepare them fresh and scale the solutions according to the number of samples to be processed.

All solutions collected as waste in this procedure should be collected e.g. in a glass bottle and finally discarded as halogen-free organic solvents Procedure Bisulfite Treatment:

Pipet the following solutions into PCR-tubes in the order shown.

1. 50 µl buffer/water containing the DNA to be bisulfite treated.
2. 95 µl bisulfite solution.
3. 15 µl DME solution, containing the radical scavenger. The total volume of the reaction mixture is 160 µl! Tightly close the caps of PCR-tubes!

Temperature Program:

5:00 min denaturation of DNA at 99° C.
22:00 min incubation at 50° C.
3:00 min denaturation of DNA at 99° C.
1:27:00 hours incubation at 50° C.
3:00 min denaturation of DNA at 99° C.
2:57:00 hours incubation at 50° C.
Cooling at 20° C.

Due to the high molarity of the bisulfite salts some of the salt may precipitate. These precipitates will not affect the bisulfite reaction.

Procedure DNA Purification:

After incubation is over, transfer reaction solution (160 µl) into 1.5 ml collection tube.

Add 120 µl ddH$_2$O to the reaction tube. Mix by pipetting up and down and transfer solution into the same collection tube.

Repeat this step with additional 120 µl ddH$_2$O!

Close caps, vortex intensively and spin shortly to remove drops from lid.

Take all of this solution (400 µl) and pipet it into the sample reservoir of an assembled Microcon filter device—do not touch the membrane with the pipet tip!

Seal with the attached cap.

Place the assembly into the centrifuge, align the cap strap towards the center of the rotor and spin 15 min at 14,000×g.

After the spin, take out assembly and discard flowthrough. PLEASE NOTE: The centrifugation efficacies may vary depending on the particular centrifuge model and instrument used. Therefore for all centrifugation steps always check whether the sample volume passed through the membrane! If needed, increase the spin times in 2 min steps.

For desulfonation add 400 µl 0.2 mol/l NaOH to the membrane place assembly back to centrifuge and spin 12 min at 14,000×g. Take out assembly and discard flowthrough.

For washing add 400 µl ddH$_2$O place assembly back to centrifuge and spin 12 min at 14,000 g. Take out assembly and discard flowthrough.

repeat this step two additional times! PLEASE NOTE: After this the membrane should look moist, but should not be covered by a visible volume of liquid.

For elution take filter assembly out of centrifuge.

Add 75 µl of prewarmed TE buffer (50° C.) into the sample reservoir. (Note: If the total amount of is critical, elution should be performed by 2 subsequent elution steps, e.g. 2×37.5 µl—should be defined prior to each study).

Incubate for 10 min at room temperature while shaking in a thermomixer at 1,000 rpm.

Invert the filter device and place it into a new Microcon 1.5 ml tube.

Elute DNA from membrane by spinning 5 min at 1,000 g.

Optional: If desired transfer DNA to a new tube—the lid of Microcon tubes tends to open quickly.

Store DNA at −80° C. for long term storage or at +4° C. for immediate use.

Example 3

All steps will be done in the tubes that the samples are provided in. The tubes can be both 1.5 and 2.0 ml tubes. Please double check that tube formats fit into the centrifuge.

The solvents and buffers can be delivered with either single channel pipettes or multipettes a) Removal of Paraffin Chemical Needed:

Limonene145, Fluka Chemika, Art Nr. 89188

Procedure:

1. Add 1 ml limonene to each tube (containing 1 to 5 sections of a paraffin-embedded formalin-fixed tissue). Push all pieces into the liquid. In some cases sample material is already very brittle with small pieces of paraffin/tissue in tube. Make sure that material sticking to the tube cap goes back into the tube.
2. 1 h incubation at RT at 1,000 rpm, vortex vigorously at least 3 times during incubation.
3. Place tubes into centrifuge and spin at 16,000 rcf (=16,000×g) for 5 min, the tissue will pellet at the tube bottom.
4. Use a 1 ml pipet to suck up the limonene from each sample. Great care should be taken not to disturb the pellet! Place pipet tip opposite the pellet onto the tube and gently allow limonene to enter the pipet tip. In some cases it can be easier to remove the entire volume in two rather than one pipetting steps.

It is o.k. if small amounts (up to 50 µl) of limonene remain in tube.

5. If the tissue settles only weakly at the bottom (i.e. not forming a nice pellet) do the following:
   Repeat centrifugation again for 5 min on EPPENDORF® 5417 centrifuge at max speed (>20,000 rcf)
   Then repeat the removal of limonene: Make sure the pipet tip is pressed against the bottom of the tube and limonene is removed very slowly such as not to suck in the tissue. Remove as much limonene as possible.

Leave out Ethanol step, if it was possible to remove nearly all limonene (if there are 50 µl left, this will be ok).

6. Add 1 ml of Ethanol (purity>99%).
7. Vortex, 10 min incubation at RT at 1,000 rpm.
8. Place tubes into centrifuge and spin at 16,000 rcf for 5 min. The tissue will pellet again at the tube bottom.
9. Use pipet to suck up the ethanol, great care should be taken not to disturb the pellet! Place pipet tip opposite the pellet onto the tube wall and gently allow ethanol to enter the pipet tip.

10. Remove as much of Ethanol as possible with the pipet.
11. Residual ethanol not removed by pipetting must be evaporated by incubation in a thermomixer at 50° C. This may take between 10 to 30 min, but take care not to overdry the samples.

No drying needed, if ethanol step was left out.

b) Lysis Step

Prepare a larger volume of the lysis buffer (0.5 or 1 l), depending on the number of samples to be processed for a project. This buffer can be stored at room temperature for 3 months. After this time it is prudent to prepare a fresh buffer.

Chemicals:
TRIS (tris-hydroxymethyl-amino-methan), Merck, Art. Nr. 1.01549.0500,
MW=121.14 g/ml
Prepare a 1 Mol/l Stock Solution:
dissolve 121.14 g in 800 ml $H_2O$ and adjust to pH 8.0 with HCl and fill up to 1 l.
EDTA (ethylendiaminetetraacetic acid),
Sodium EDTA (Titriplex III) from Merck, Art. Nr. 159294
MW=372.24 g/mol
Prepare a 0.5 Mol/l Stock Solution:
Dissolve 186.1 g in 800 ml $H_2O$ and adjust to pH 8.0 with NaOH, fill up to 1 l.
Tween (Tween 20), Fluka, Chemika Art Nr. 93773
This detergent is added to the buffer in volume percent. To add Tween to the buffer take 1 ml of Tween (in 2 ml tube), warm it at 50° C. and add desired volume to buffer with a widened pipet tip.

Lysis Buffer Composition:
50 mmol/l TrisHCl, pH 8.0, 1 mmol/l EDTA, 0.5% Tween (volume %)

Proteinase K, Roth
Prepare a 30 mg/ml stock solution in $H_2O$. The size of the stock solution should be adjusted to the number of samples to be processed. For example, 300 mg proteinase K dissolved in 10 ml $H_2O$ will be sufficient for ~400 samples. Proteinase K can be stored at 4° C. for up to one week safely. If more samples will be processed it is recommended to prepare fresh solutions repeatedly.

Procedure:
1. Add 190 μl of the prepared lysis buffer to each sample. It is important to ensure that all sample material is covered by lysis buffer.
2. Add 20 μl of the prepared proteinase K solution.
3. Vortex the tube rigorously to ensure proper mixing of sample with lysis buffer and proteinase K. Make sure the tube caps are tightly closed—otherwise loss of liquid will happen!
4. Incubate at 50° C., shaking 1,000 rpm (thermoshaker).
5. Incubate for 40 to 48 h, no further additions of proteinase K necessary.
6. Spin in the morning and the evening of each day to remove droplets from the cap, vortex vigorously.

Quality Check of Lysis (During Lysis):
After these lysis steps, there should be a homogeneous, maybe turbid solution in the tube with no visible pieces of tissue left. However, should there be visible pieces of tissues in MANY of the samples left after the first over night incubation additional proteinase K step and increase of lysis volume should be considered. If only individual samples have some undigested material left this may be neglected. Have a careful look!
7. Incubate samples at >95° C. for 10 min in to order to inactive proteinase K. For this set the temperature of the thermomixer at 99° C., since the real temperature at the highest setting is some degrees below the indicated temperature. (Active proteinase K in the lysate will reduce PCR performance, especially if lysate is used directly for quantitation of genomic DNA by RT-PCR.)
8. Lysed samples may be stored at either –20° C. or –80° C. (depending on storage time) or be used immediately for downstream processing Example 4

All steps will be done in the tubes in which the samples are provided. The tubes can be both 1.5 and 2.0 ml tubes. Please double check that tube formats fit into the centrifuge.

The solvents and buffers can be delivered with either single channel pipettes or multipettes.

a) Removal of Paraffin

Chemical Needed:
Limonene145, Fluka Chemika, Art Nr. 89188
Procedure:
1. Add 1 ml limonene to each tube (containing 1-6 sections of a paraffin-embedded formalin-fixed surgery sample or an equal amount of a biopsy). In some cases sample material is already very brittle with small pieces of paraffin/tissue in tube—make sure that material sticking to the tube cap goes back into the tube.
2. 10 min incubation at room temperature, during incubation vortex rigorously several times (2-4×5 sec) such that the sample disintegrates as much as possible. This may vary from sample to sample.
3. Place tubes into centrifuge and spin at 16,000 rcf (=16,000×g) for 5 min. The tissue will pellet at the tube bottom.
4. Use a 1 ml pipet to suck up the limonene from each sample. Great care should be taken not to disturb the pellet! Place pipet tip opposite the pellet onto the tube and gently allow limonene to enter the pipet tip. In some cases it can be easier to remove the entire volume in two rather than one pipetting steps. It is o.k. if small amounts (few μl) of limonene remain in tube.
5. If the tissue settles only weakly at the bottom (i.e. not forming a nice pellet) do the following:
repeat centrifugation again for 5 min on EPPENDORF® 5417 centrifuge at max speed (>20,000 rcf)
then repeat the removal of limonene: make sure the pipet tip is pressed against the bottom of the tube and limonene is removed very slowly such as not to suck in the tissue. Remove as much limonene as possible.
6. Add 1 ml of Ethanol (purity>99%).
7. 10 min incubation at room temperature. During incubation vortex tubes 2-3 times such that the pellet loosens and all tissue is soaked in ethanol.
8. Place tubes into centrifuge and spin at 16,000 rcf for 5 min, the tissue will pellet again at the tube bottom.
9. Use pipet to suck up the ethanol, great care should be taken not to disturb the pellet! Place pipet tip opposite the pellet onto the tube wall and gently allow ethanol to enter the pipet tip. Remove as much of ethanol as possible with the pipet.
10. Residual ethanol not removed by pipetting must be evaporated by incubation in a thermomixer at 50° C. This may take between 10 to 30 min, but take care not to overdry the samples.

b) Lysis Step

Prepare a larger volume of the lysis buffer (0.5 or 1 l), depending on the number of samples to be processed for a project. This buffer can be stored at room temperature for 3 months. After this time it is prudent to prepare a fresh buffer.

Chemicals:

TRIS (tris-hydroxymethyl-amino-methan), Merck, Art. Nr. 1.01549.0500; MW=121.14 g/ml; Prepare a 1 mol/l stock solution: Dissolve 121.14 g in 800 ml H$_2$O and adjust to pH 8.0 with HCl and fill up to 1 l. A 50 mmol/l Tris solution should be prepared from this stock by dilution.

EDTA (ethylendiaminetetraacetic acid); sodium EDTA (Titriplex III) from Merck, Art. Nr. 159294; MW=372.24 g/mol; prepare a 0.5 mol/l stock solution: Dissolve 186.1 g in 800 ml H$_2$O and adjust to pH 8.0 with NaOH, fill up to 1 l.

Tween (Tween 20), Fluka, Chemika Art Nr. 93773; this detergent is added to the buffer in volume percent. To add Tween to the buffer take 1 ml of Tween (in 2 ml tube), warm it at 50° C. and add desired volume to buffer with a widened pipet tip.

Lysis Buffer Composition:

50 mmol/l TrisHCl, pH 8.0, 1 mmol/l EDTA, 0.5% Tween (volume %).

Proteinase K, Roth

Prepare a 10 mg/ml stock solution in H$_2$O. The size of the stock solution should be adjusted to the number of samples to be processed. For example, 100 mg proteinase K dissolved in 10 ml H$_2$O will be sufficient for ~160 samples. Proteinase K can be stored at 4° C. for up to two weeks safely. If more samples will be processed it is recommended to prepare fresh solutions repeatedly.

Procedure:

1. Add 150 μl of the prepared lysis buffer to each sample. It is important to ensure that all sample material is covered by lysis buffer.
2. Add 20 μl of the prepared proteinase K solution. Vortex the tube rigorously to ensure proper mixing of sample with lysis buffer and proteinase K. Very briefly spin to bring down droplets. Make sure the tube caps are tightly closed—otherwise loss of liquid will happen!
3. Incubate at 50° C., shaking 1,000 rpm (thermoshaker).
4. Incubate for 40 h, with a total of 3× proteinase K injections (always 20 μl).
5. After each incubation period the tubes should be briefly spinned to remove any liquid from the cap to prevent contamination risk (via gloves). After the proteinase K injection, samples should be vortexed to ensure proper mixing. Spin down and continue with incubation.

Incubation scheme: 1 overnight, 1 day, 1 overnight

Suggested workschedule:
a. Per person not more than 24 samples should be processed in parallel.
b. Sample deparaffination of 24 samples will take approximately 2 h.
c. First proteinase K step at 16:00.
d. Second proteinase K step next day 8:00.
e. Third proteinase K step this day at 16:00.
f. Lysis complete overnext day at 8:00.

Quality Check of Lysis (after End of Lysis):

After these lysis steps, there should be a clear solution in the tube with no visible pieces of tissue left. However, should there be visible pieces of tissues in MANY of the samples left additional proteinase K steps should be considered. If only individual samples have some undigested material left this may be neglected.

6. Incubate samples at >95° C. for 10 min in to order to inactive proteinase K. For this the temperature of the thermomixer is set to 99° C., since the real temperature at the highest setting is some degrees below the indicated temperature. (Active proteinase K in the lysate will reduce PCR performance, especially if lysate is used directly for quantitation of genomic DNA by RT-PCR)
7. Lysed samples may be stored at either −20° C. or −80° C. (depending on storage time) or be used immediately for downstream processing.

c. DNA Extraction with QIAGEN® DNA-Mini-Kit

Time Exposure for 30 Samples:

Provision of devices and materials (15 min); Preparation (0.5 h); Implementation (1.5 h).

Provision of Devices and Materials:

The following devices/means of labour are needed:

centrifuge EPPENDORF® 5417R, EPPENDORF® pipettes, 1.5 ml reaction-tubes, 2 ml reaction-tubes, thermomixer or waterbath.

The Following Reagents are Needed:

Sample units (liquid or tissue)

Phosphate buffered saline (PBS)

Ethanol (96-100%)

Water for molecular biology (0.2 μm-filtered, DEPC-treated, autoclaved, and free of DNases, RNases, proteases, and phosphatases)

QIAAMP® DNA-Mini-Kit

Preparation of Solutions:

1. Mix buffer AL thoroughly by shaking before use. Buffer AL is stable for 1 year when stored at room temperature. If a precipitate has formed in buffer AL, dissolve by incubating at 70° C.
2. Buffer AW 1 is supplied as a concentrate. Add 125 ml ethanol (96-100%) before first use. Buffer AW 1 is stable for 1 year when stored closed at room temperature.
3. Buffer AW 2 is supplied as a concentrate. Add 160 ml ethanol (96-100%) before first use. Buffer AW 2 is stable for 1 year when stored closed at room temperature.
4. Equilibrate samples to room temperature.
5. Heat a waterbath or thermomixer to 56° C.
6. Equilibrate the desired elution buffer (buffer AE or water) to room temperature.
7. All centrifugation steps should be carried out at room temperature.

Procedure:

1. Add 200 μl Buffer AL to the sample. Mix by pulse-vortexing for 15 sec.
2. Incubate at 56° C. for 10 min. A longer incubation may lead to DNA degradation!
3. Add 200 μl ethanol (96-100%) to the sample, and mix by pulse-vortexing for 15 sec. After mixing, briefly centrifuge the 1.5 ml reaction tube to remove drops from the inside of the lid.
4. Carefully apply the mixture from step 3 on a QIAAMP® spin column previously placed in a 2 ml collection tube without wetting the rim. Close the cap and centrifuge at 6,000×g (8,000 rpm) for 1 min. Place the QIAAMP® spin column in a clean 2 ml collection tube (provided), and discard the tube containing the filtrate.
5. Carefully open the QIAAMP® spin column and add 500 μl buffer AW 1 without wetting the rim. Close the cap and centrifuge at 6,000×g (8,000 rpm) for 1 min. Place the QIAAMP® spin column in a clean 2 ml collection tube (provided), and discard the collection tube containing the filtrate.
6. Carefully open the QIAAMP® spin column and add 500 μl buffer AW 2 without wetting the rim. Close the cap and centrifuge at full speed 20,000×g (14,000 rpm) for 3 min.

7. Discard the filtrate, dry the collection tubes by beating them on a kleenex tissue on the bench, insert the column and spin again for 1 min at 8,000 rpm to remove residual ethanol present in AW2.
8. Place the QIAAMP® spin column in a clean 1.5 ml reaction-tube, and discard the collection tube containing the filtrate. Carefully open the QIAAMP® spin column and add an adequate volume (50-150 µl) of warm (~40° C.) buffer AE or water. 9. Incubate at room temperature for 1 min, and then centrifuge at 6,000×g (8,000 rpm) for 1 min.
10. Take the eluate and pipet it a second time on the QIAAMP® spin column. Incubate at room temperature for 1 min, and then centrifuge at 6,000×g (8,000 rpm) for 1 min. Incubation of the QIAAMP® spin column loaded with buffer for 5 min at room temperature before centrifugation generally increases DNA yield.
11. For immediate use, a storage at +4° C. in the fridge is acceptable, while for long term, storage at −20° C. is recommended.
12. Optional, the quality and the quantity should be checked by measurement with the photometer. A sample of 200 µl whole human blood typically yields 6 µg of DNA in 200 µl water (30 ng/µl) with an A260/A280 ratio of 1.7-1.9. A further quality control of the DNA status would be to load around 5 µl (1 µl sample+4 µl water) on an 0.8% agarose gel. By this check, the level of DNA degradation and the average fragment size as well as the rough concentration can be determined.

Example 5 a) Bisulfite Treatment and b) DNA Purification with MICROCON™ Device and Using Dioxane Equipment Needed:
thermo cycler (e.g. EPPENDORF®, Tetrad)
centrifuge (capable of up to 14,000×g)
pipettors for volumes of 100 µl and 1,000 µl
Material Needed:
MICROCON™ Centrifugal Filter devices, MICROCON™ YM-30, MILLIPORE®/AMICON®
Pipet tips (100 µl, 1,000 µl)
200 ul PCR tubes, thin wall
1.5 ml reaction-tubes
15 ml and 50 ml Falcon tubes
Chemicals Needed:
sodium bisulfite ($Na_2S_2O_5$, MW=190.1 g/mol), Merck 1.06528.0500
sodium sulfite, anhydrous ($Na_2SO_3$, MW=126.04 g/mol), Fluka 71988
$ddH_2O$ molecular biology grade (0.2 µm filtered, DEPC-treated, autoclaved, free of DNases and RNases)
1,4-dioxane, stabilized (MW=88.11 g/mol), Riedel de Haen 33147
6-hydroxy-2,5,7,8-tetramethylchroman-2-carboxylic acid (MW=250.29 g/mol), Aldrich 23, 881-3
Tris-hydroxymethyl-aminomethan (M=121.14 g/mol), Merck 1.01549.0500
sodium hydroxide pellets (MW=40 g/mol), Merck 1.06482.1000
EDTA (Titriplex® III, MW=372.24 g/mol), Merck 1.08418.0250
Preparation of Solutions:
Bisulfite solution: Sodium disulfite (4.708 g) and sodium sulfite (1.128 g) are dissolved by adding 10 ml $ddH_2O$ (the solution is 4.9 M). Check pH of the solution—if it is not between 5.45 and 5.5, discard solution and repeat preparation. Shake rigorously and if needed, heat the solution to 50° C. in a waterbath than vortex at max speed for 30 sec. Repeat this procedure as often until the salt is completely dissolved.
Dioxane-radical scavenger solution: Dissolve 197.2 mg of 6-hydroxy-2,5,7,8-tetramethyl-chroman-2-carboxylic acid by adding 5 ml 1,4-dioxane. Vortex rigorously in order to ensure that no undissolved particles remain. Dioxane is hazardous. Therefore take appropriate precautions when handling this chemical. If only few samples are to be bisulfite treated, prepare smaller volumes.
NaOH 0.2 M: Dissolve 0.32 g sodium hydroxide in 40 ml $ddH_2O$. TE buffer: 10 mmol/l Tris, 0.1 mmol/l EDTA, pH 8.
General:
This procedure can be applied to a single sample or many samples in parallel.
The working solutions should not be stored over prolonged periods of time. It is best to prepare them fresh and scale the solutions according to the number of samples to be processed.
All solutions collected as waste in this procedure should be collected e.g. in a glass bottle and finally discarded as halogen-free organic solvents.
Procedure:
Pipet the following solutions into a 200 ul PCR tube in the order shown:
1. 20 µl buffer/water containing the DNA to be bisulfite treated.
2. 85 µl bisulfite solution.
3. 35 µl dioxane solution, containing the radical scavenger (total volume of the reaction mixture is 140 µl)
Temperature Program:
5:00 min denaturation of DNA at 99° C.
25 min incubation at 60° C.
5:00 min denaturation of DNA at 95° C.
1:25 hours incubation at 60° C.
5:00 min denaturation of DNA at 95° C.
2:55 hours incubation at 60° C.
cooling at 20° C. forever
Due to the high molarity of the bisulfite salts some of the salt may precipitate. These precipitates will not affect the bisulfite reaction.
DNA Purification:
1. After incubation is over, transfer reaction solution (140 µl) into 1.5 ml collection tube, add 260 µl $ddH_2O$ into the collection tube.
2. Mix by vortexing.
3. Take all of this solution (400 µl) and pipet it into the sample reservoir of an assembled Microcon filter device. (Do not touch the membrane with the pipet tip!)
4. Seal with the attached cap.
5. Place the assembly into the centrifuge, align the cap strap towards the center of the rotor and spin 15 min at 14,000×g (=rcf).
6. After the spin take out assembly and discard flowthrough.
PLEASE NOTE: the centrifugation efficacies may vary depending on the particular centrifuge model and instrument used. Therefore for all centrifugation steps always check whether the sample volume passed through the membrane! If needed, increase the spin times in 2 min steps.
7. Take filter assembly out of centrifuge.
8. Add 400 µl 0.2 mol/l NaOH to the membrane.
9. Place assembly back to centrifuge and spin 12 min at 14,000×g, discard flowthrough.
10. Wash the membrane with by adding 400 µl water and spin for 12 min, discard flowthrough.
11. Repeat washing-step two more times.

12. The membrane should look moist, but should not be covered by a visible volume of liquid.
13. For elution, take filter assembly out of centrifuge.
14. Add 75 µl of prewarmed (50° C.) TE buffer (Tris/HCl 10 mmol/l; EDTA 0.1 mmol/l) into the sample reservoir.
15. Incubate for 10 min while shaking on a thermomixer with 1,000 rpm (50° C.).
16. Invert the filter device and place it into a new Microcon 1.5 ml tube.
17. Spin 5 min at 1,000×g.
18. Store DNA at −20° C. for long term storage or at +4° C. for immediate use.

Example 6

DNA Purification by Means of a QIAAMP® Viral RNA Mini Kit

Equipment Needed:
Tube centrifuge
Pipettors for volumes of from 10 µl to 1,000 µl
Material Needed:
QIAAMP® Viral RNA Mini Kit (50) (QIAGEN® cat#52904)
Pipet tips (100 µl, 1,000 µl)
Chemicals Needed:
Ethanol, molecular biology grade
Sodium hydroxide pellets (NaOH, MW=40.0 g/mol), Merck 1.06482.1000
Preparation of Solutions:
Desulfonation buffer: Dissolve 0.8 g sodium hydroxide in 10 ml ddH$_2$O to prepare a 2 mol/l stock solution. For the desulfonation buffer mix 1.0 ml 2 mol/l sodium hydroxide and 9.0 ml ethanol. The solution has to prepared freshly before each purification!
AVL-buffer: Add 1 ml of buffer AVL to one tube of lyophilized carrier RNA. Dissolve thoroughly. Transfer to the buffer AVL bottle, and mix thoroughly before using buffer AVL for the first time. This buffer can be stored at 2-8° C. for future use. However, if a precipitate develops, then redissolve by heating at 80° C. This should be done no more than a total of 6 times. Cool to room temperature before use. A small aliquot can be kept at room temperature for up to 2 weeks.
Procedure:
1. For binding of bisulfite treated DNA, pipet 560 µl of prepared buffer AVL/carrier RNA into the tubes containing 140 µl bisulfite treated DNA solution. Add 560 µl ethanol to the samples. Pulse-vortex for 15 sec. Centrifuge briefly.
2. Incubate at room temperature for 10 min.
3. Load 630 µl of the mixture from step 2 to the QIAAMP® spin column, which is placed in a collection tube (pre-labeled). Close the cap and centrifuge at full speed for 1 min.
4. Place the spin column in a clean 2 ml collection tube and load the rest of the mixture from step 2. Close the cap and centrifuge at full speed for 1 minute.
5. For washing, add 500 µl buffer AW1 to the spin column in a clean 2 ml collection tube. Centrifuge at full speed for 1 min. Discard the filtrate.
6. For desulfonation, add 500 µl 0.2 mol/l NaOH/ethanol to the spin column in a clean 2 ml collection tube. Incubation for 15 min at room temperature. Centrifuge at full speed for 1 min.
7. Add 500 µl buffer AW2 spin column in a clean 2 ml collection tube. Centrifuge at 14,000 rpm for 3 min. Discard the filtrate.
8. Place the QIAAMP® spin column in a new 2 ml collection tube. Centrifuge at 14,000 rpm for 1 min to eliminate possible buffer AW2 carryover. Discard the filtrate.
9. Place the QIAAMP® spin column in a 1.5 ml pre-labeled micro-centrifuge tube. Add 75 µl buffer AVE to the QIAAMP® spin columns. Incubate for 5 min at room temperature. Centrifuge at 9.000 rpm for 1 min.

Example 7

Lysis Step by Means of Heating

1. Centrifuge 1-6 paraffin-embedded formalin-fixed tissue sections in a 1.5 ml reaction tube for 5 min at 16,000×g.
2. Add 100 µl lysis buffer (50 mmol/l TrisHCl, pH 8.0, 1 mmol/l EDTA, 0.5 v/v % Tween 20, 5 ng/µl polydA)
3. Incubate 10 min at 65° C. with agitation at 1,000 rpm in a thermomixer.
4. Set thermomixer to 50° C. and 1,400 rpm, leave samples in thermomixer and allow them to cool down.
5. Add 10 µl proteinase K (30 mg/ml).
6. Spin down to remove all droplets from the tube wall. Make sure the tube caps are tightly closed—otherwise loss of liquid will happen.
7. Incubate 40-48 h at 60° C. in a thermomixer with agitation at 1,000 rpm.
8. Incubate samples at >95° C. for 10 min in to order to inactive proteinase K. For this, set the thermomixer temperature to 99° C. Transfer tubes IMMEDIATELY to another thermomixer tempered to 50° C., agitate at 1,400 rpm and incubate for 5 min. This avoids the formation of a paraffin film.
9. Apply 44 µl of this lysate directly (without further extraction) to example 8.

Example 8 a) Bisulfite Treatment and b) DNA Purification by Means of MICROCON™ Device and Using DME Equipment Needed:
thermo cycler (e.g. EPPENDORF®, Tetrad)
centrifuge (capable of up to 14,000×g)
pipettors for volumes of 100 µl and 1,000 µl
Material Needed:
MICROCON™ Centrifugal Filter devices, MICROCON™ YM-30 (MILLIPORE®/AMICON® 42410)
pipet tips (100 µl, 1,000 µl)
200 µl PCR-tubes (e.g. EPPENDORF® 0030 124.359)
1.5 ml tubes (e.g. EPPENDORF® 0030 120.086)
15 ml and 50 ml Falcon tubes
Chemicals Needed:
sodium bisulfite (Na$_2$S$_2$O$_5$, MW=190.1 g/mol), Merck 1.06528.0500
sodium sulfite, anhydrous (Na$_2$SO$_3$, MW=126.04 g/mol), Fluka 71988
ddH$_2$O molecular biology grade (0.2 µm filtered, DEPC-treated, autoclaved, free of DNases- and RNases)
diethyleneglycoldimethylether (DME), Merck 8.02934.0250
6-hydroxy-2,5,7,8-tetramethylchroman-2-carboxylic acid (MW=250.29 g/mol), Aldrich 23, 881-3
Tris-hydroxymethyl-aminomethan ($C_4H_8O_2$, MW=121.14 g/mol), Merck 1.01549.0500
sodium hydroxide pellets (NaOH, MW=40.0 g/mol), Merck 1.06482.1000

EDTA (Titriplex® III, $C_{10}H_{14}N_2O_8Na_2$ · $2H_2O$, MW=372.24 g/mol), Merck 1.08418.0250

Preparation of Solutions (Sufficient for 80 Reactions):

Bisulfite solution: Sodium disulfite (4.708 g) and sodium sulfite (1.128 g) are dissolved by adding 10 ml dd$H_2O$ (the solution is 4.9 M). The final volume is around 12 ml. Check pH of the solution—if it is not between 5.45 and 5.5, discard solution and repeat preparation. Shake rigorously and if needed, heat the solution to 50° C. in a waterbath than vortex at maximum speed for 30 sec. Repeat this procedure as often until the salt is completely dissolved.

DME-radical scavenger solution: Dissolve 125.3 mg of 6-hydroxy-2,5,7,8-tetramethyl-chroman-2-carboxylic acid by adding 1.0 ml DME. Vortex rigorously in order to ensure that no undissolved particles remain. If only few samples are to be bisulfite treated, prepare smaller volumes.

NaOH 0.2 M: dissolve 0.32 g sodium hydroxide in 40 ml dd$H_2O$.

TE buffer: 10 mmol/l Tris, 0.1 mmol/l EDTA, pH 8.

General:

This procedure is designed to be applied in 200 µl PCR-tubes. The total number of samples is limited by the number of tubes that can be handled in the thermocyclers, centrifuges, etc.

The working solutions should not be stored over prolonged periods of time. It is best to prepare them fresh and scale the solutions according to the number of samples to be processed.

All solutions collected as waste in this procedure should be collected e.g. in a glass bottle and finally discarded as halogen-free organic solvents Procedure Bisulfite Treatment:

Pipet the following solutions into PCR-tubes in the order shown.
1. 45 µl buffer/water containing the DNA to be bisulfite treated.
2. 83 µl bisulfite solution.
3. 13 µl DME solution, containing the radical scavenger.
4. Mix thoroughly.
5. Place in 0.2 ml wells of thermocycler.

The total volume of the reaction mixture is 141 µl! Tightly close the caps of PCR-tubes!

Temperature Protocol:
5:00 min denaturation of DNA at 99° C.
22:00 min incubation at 60° C.
3:00 min denaturation of DNA at 99° C.
1:27:00 hours incubation at 60° C.
3:00 min denaturation of DNA at 99° C.
2:57:00 hours incubation at 60° C.
Cooling at 20° C.

Due to the high molarity of the bisulfite salts some of the salt may precipitate. These precipitates will not affect the bisulfite reaction.

Procedure DNA Purification:

After incubation is over, transfer reaction solution (141 µl) into 1.5 ml collection tube.

Add 260 µl dd$H_2O$ to the collection tube.

Close caps, vortex intensively and spin shortly to remove drops from lid.

Take all of this solution (400 µl) and pipet it into the sample reservoir of an assembled Microcon filter device—do not touch the membrane with the pipet tip!

Seal with the attached cap.

Place the assembly into the centrifuge, align the cap strap towards the center of the rotor and spin 15 min at 14,000×g (=rcf).

After the spin take out assembly and discard flowthrough. PLEASE NOTE: the centrifugation efficacies may vary depending on the particular centrifuge model and instrument used. Therefore for all centrifugation steps always check whether the sample volume passed through the membrane! If needed, increase the spin times in 2 min steps.

For desulfonation, add 400 µl 0.2 mol/l NaOH to the membrane.

Place assembly back to centrifuge and spin 12 min at 14,000×g. Take out assembly and discard flowthrough.

Add 400 µl dd$H_2O$.

Place assembly back to centrifuge and spin 12 min at 14,000×g. Take out assembly and discard flowthrough.

Repeat this step two additional times!PLEASE NOTE: after this the membrane should look moist, but should not be covered by a visible volume of liquid.

For elution of the DNA, take filter assembly out of centrifuge.

Add 75 µl of prewarmed TE buffer (50° C.) into the sample reservoir. (Note: If the total amount of is critical, elution should be performed by 2 subsequent elution steps, e.g. 2×37.5 µl—should be defined prior to each study)

Incubate for 10 min at 50° C. while shaking in a thermomixer at 1,000 rpm.

Invert the filter device and place it into a new MICROCON™ 1.5 ml tube.

Elute DNA from membrane by spinning 5 min at 1,000 g. (if desired transfer DNA to a new tube—the lid of MICROCON™ tubes tends to open quickly)

store DNA at −80° C. for long term storage or at +4° C. for immediate use.

Example 9

9.1. Sample Sets 9.1.1. Estrogen Receptor Positive (ER+) Nodal Status Negative (N0) Untreated Population ER+N0 tumor samples from patients not treated with any adjuvant therapy were analyzed. Markers that are able to show a significant survival difference in this population are considered to be prognostic. Since adjuvant therapy has become the routine regiment for breast cancer patients for many years, the collected sample set is a historical one from the Eighties of the last century.

All 508 samples of this set were obtained from the Erasmus Medical Center in Rotterdam as cell nuclei pellets (fresh frozen samples).

9.1.2. ER+N0 Tamoxifen (TAM) Treated Population

The target population of the final test is supposed to be patients with ER+N0 tumors that are treated with hormone therapy. To check the performance of the marker candidates in this population, 589 samples from ER+N0 tumors from patients treated with Tamoxifen were analyzed. All samples were received as paraffin-embedded formalin-fixed tissues (PET). Three to ten 10 µm sections were provided.

In addition, for 89 PET patient samples matching fresh frozen samples from the same tumor were included into the study as controls.

9.2. DNA Extraction 9.2.1. DNA Extraction from Fresh Frozen Samples

From a total of 508 fresh frozen samples available as cell nuclei pellets, genomic DNA was isolated using the DNEASY® Tissue Kit (QIAGEN®, Hilden, Germany). The extraction was done according to the Cell Culture protocol using Proteinase K with few modifications.

20 μl of Proteinase K (QIAGEN®, Hilden, Germany) were pipetted into a 2 ml reaction tube (EPPENDORF®, Hamburg, Germany) containing the pellets. 200 μl PBS buffer was added and pulse-vortexed overnight at 37° C. Another 200 μl of AL buffer were added and subsequently pulse-vortexed again at 56° C. for 10 minutes. After incubation at 70° C. for 10 minutes, 200 μl ethanol (96%) was added and incubated for 15 seconds. The mixture was applied to a column and centrifuged at 6,000×g for 1 min. The column was placed into a provided 2 ml collection tube and 500 μl buffer AW 1 was added. After centrifugation at 6,000×g for 1 minute, 500 μl AW 2 buffer was added to the column placed in another provided 2 ml collection tube followed by centrifugation at 20,000×g for 3 min. The collection tube was kept open to dry the DNA pellet for several minutes and spin again at 6,000×g to remove residual ethanol present in buffer AW 2. The column was placed into an clean 1.5 ml reaction tube (EPPENDORF®, Hamburg, Germany) and 60 μl of prewarmed (~40° C.) buffer AE was added. After incubation at room temperature for 1 min, samples were centrifuged at 6,000×g for 1 min. The eluate was pipetted a second time on the column incubated again at room temperature for 1 min with the following step of centrifugation under same conditions. The quality and quantity of the extracted genomic DNA was checked by photometrical measurement (A260 and A280). Extracted DNA was stored at −20° C. until further processing.

9.2.2. Deparaffination, Lysis, and DNA Extraction from Paraffin-Embedded Formalin-Fixed (PET) Samples For deparaffination, 589 provided paraffin-embedded formalin-fixed (PET) samples were processed directly in the tube in which they were delivered by the providers. 1 ml of limonene was added to each tube which contained 3 to 10 sections, each about 10 μm thick and incubated at room temperature for 10 minutes. During incubation they were vortexed rigorously several times (2-4×5 seconds). The paraffin samples were centrifuged at 16,000×g for 5 minutes. The limonene supernatant was removed very carefully by placing a pipet onto the opposite side of the pellet. If no pellet was received, centrifugation was repeated at higher speed (20,000×g) for the same time and the remaining limonene was removed. Afterwards 1 ml of EtOH (purity>99%) was added and incubated at room temperature for 10 minutes while vortexing 2-3 times. Then the tubes were centrifuged at 16,000×g for 5 min. As much ethanol as possible without disturbing the pellet was removed by pipetting. Residual ethanol not removed by pipetting was evaporated by incubation in a thermomixer at 50° C. for 10 up to 30 minutes.

For lysis of the tissue, 150 μl lysis buffer (50 mmol/l TrisHCl, pH 8.0, 1 mmol/l EDTA, 0.5% Tween (volume %), TRIS (tris-hydroxymethyl-amino-methan), Merck, no 1.01549.0500, Sodium EDTA (Titriplex III) from Merck, no. 159294, Tween (Tween20), Fluka, no. 93773) as well as 20 μl proteinase K (10 mg/ml stock solution in H₂O, Roth, Karlsruhe) was added to each deparaffinated sample. After vortexing rigorously, samples were shortly centrifuged and incubated on a thermoshaker at 50° C. During the incubation period of about 40 hours, proteinase K was added every 8-12 hours (altogether three times). The tubes were always briefly centrifugated before opening to avoid contamination. After the lysis step, samples were checked to be clear, containing no debris anymore. Subsequently the inactivation of proteinase K was done by incubation the lysed samples at 95° C. for 10 minutes. If lysed samples were not directly used for DNA extraction, they were stored at −20° C.

The DNA-Isolation from lysates of paraffin-embedded formalin-fixed tissue (PET) samples was done with the DNEASY® Tissue kit (QIAGEN® cat no. 69504 [50 columns] or 69506 [250 columns]) with few modifications. 200 μl buffer AL was added to 210 μl room temperature equilibrated lysate and mixed thoroughly by vortexing. This mixture was placed into a thermomixer and incubated at 70° C. while shaking for 10 minutes. Then 200 μl 96% ethanol was added and mixed by pulse-vortexing for 15 sec. After a brief centrifugation, the whole mixture was applied onto a column which was placed into a 2 ml collection tube (QIAGEN® provided). This was followed by centrifugation at 6,000×g for 1 minute. Afterwards the column was placed into a 2 ml collection tube (QIAGEN® provided) and 500 μl of AW 1 buffer was added. Recentrifugation under same conditions was applied. The column was placed into an additional provided collection tube and AW 2 buffer was added followed by centrifugation at 20,000×g for 3 min. After some minutes of drying, the centrifugation step was repeated at 20,000×g for 1 minute. To eluate the DNA, the column was placed into a 1.5 ml reaction-tube (EPPENDORF®, Hamburg, Germany) and 35 μl of elution buffer AE (adjusted to room temperature) was pipetted onto the center of the column. After incubation at room temperature for 1 minute, the column was centrifuged at 6,000×g for 1 minute. Another 35 μl elution buffer was added to the column and the centrifugation repeated. Therefore, the final volume of extracted DNA was appr. 70 μl. DNA was stored −20° C.

9.3. Bisulfite Treatment 9.3.1. Bisulfite Treatment of Fresh Frozen Samples

Extracted genomic DNA was modified by bisulfite treatment. During the bisulfite reaction, unmethylated cytosines are first sulfonated, during a next step deaminated, and finally desulfonated converting them to uracil while 5'-methylcytosin remains unaffected.

In order to avoid potential process biases, all samples were randomized in batches of about 30 samples regarding their clinical follow-up. This randomization was transferred to the 384 well plate layout of the assay plates resulting in a satisfactorily randomization for these plates as well. The bisulfite treatment of genomic DNA derived from fresh frozen material was carried out as described in the following. 15 μl of lysed genomic DNAs was pipetted into a 96 well plate for each bisulfite batch according the randomization. Afterwards 60 μl bisulfite solution (4.9 M, pH 5.5; sodium bisulfite, Merck 1.06528.0500, sodium sulfite, anhydrous, Fluka 71988, ddH₂O molecular biology grade) and 25 μl dioxane solution containing the radical scavenger (dioxane-radical scavenger solution: 98.6 mg of 6-hydroxy-2,5,7,8-tetramethyl-chroman-2-carboxylic acid, Aldrich 23, 881-3 with 2.5 ml 1,4-dioxane, Riedel de Haën 33147) were added to each well. The total volume of 100 μl per well were sealed by cap-strips.

The reaction mixture was thermocycled by the following protocol:
  5:00 min denaturation of DNA at 99° C.
  1:30 min cooling down to 4° C.
  23:30 min incubation at 50° C.
  3:00 min denaturation of DNA at 99° C.
  1:30 min cooling at 4° C.
  1:25:30 hours incubation at 50° C.
  3:00 min denaturation of DNA at 99° C.
  1:30 min cooling at 4° C.
  2:55:30 hours incubation at 50° C. cooling down to 4° C.

After incubation, the reaction was transferred into a 500 μl collection tube (EPPENDORF® no. 124.502, Hamburg, Germany) and 300 μl ddH$_2$O was added to increase the solubility of the bisulfite salts.

The whole mixture of 400 μl was pipetted into a sample reservoir of an assembled MICROCON™ filter device (MICROCON™ YM-30, 42410, MILLIPORE®, USA) and sealed with the attached cap. The assembly was centrifuged at 14,000×g for 15 minutes. After discarding the flowthrough, 400 μl TE buffer was added and centrifuged again at same speed for 12 minutes. The washing step was repeated once. For the desulfonation, 100 μl NaOH 0.2 mol/l (Merck no. 1.06482.1000) was added to the filter assembly without touching the membrane and incubated at room temperature for 10 minutes. The assembly was centrifuged again at same speed for 10 minutes. The residual sodium hydroxide solution was removed by washing the membrane with 400 μl TE buffer and centrifugation at same speed for 12 minutes. For elution of the bisulfite converted DNA (bisDNA), 50 μl of prewarmed TE buffer (50° C.) (10 mmol/l Tris, Merck no. 1.01549.0500; 0.1 mmol/l EDTA, pH 8, Merck no. 1.08418.0250) were pipetted into each sample reservoir and incubated at room temperature for 10 minutes. Subsequently the filter device was inverted and placed into a new MICROCON™ 1.5 ml tube and centrifuged at 1,000×g for 5 minutes. The bisulfite treated DNA samples were transferred into a new 96 well plate according to their specified sample order. The bisulfite treated DNA samples were stored at −20° C.

9.3.2. Bisulfite Treatment of Paraffin-Embedded Formalin-Fixed Tissue (PET) Samples The bisulfite treatment of genomic DNA derived from paraffin-embedded formalin-fixed tissue was done according to example 5. For this process, the samples were randomized not only regarding to their clinical follow-up but also regarding to their providers. For paraffin-embedded formalin-fixed (PET) samples, half of the volume obtained from DNA extraction was used for subsequent bisulfite reaction.

The procedure was especially designed for bisulfite-treatment of paraffin embedded formalin-fixed tissue samples (PET-samples) to increase the resulting bisDNA amount. Therefore, two bisulfite reactions of the same DNA sample were performed and purified on one Microcon™ spin-column. The following modifications compared to the fresh frozen protocol (see above) were conducted. The first step of pipetting 15 μl of lysed genomic DNAs into a 96 well plate with 60 μl bisulfite solution (for ingredients see above) and 25 μl dioxane solution (for ingredients see above) containing the radical scavenger was done twice for each DNA sample. The incubation step was performed with the same thermocycler program as for the fresh frozen samples. After incubation, both reactions (200 μl in total) originating from the same sample DNA were transferred into one 500 μl collection tube (EPPENDORF® no. 124.502, Hamburg, Germany) while each well was washed with 100 μl ddH$_2$O and also transferred to the collection tube containing finally 400 μl reaction solution. After mixing briefly, the solution was pipetted into the sample reservoir of an assembled Microcon™ filter device and purified, desulfonated and eluted as the fresh frozen sample DNA. The bisulfite treated DNA samples were stored at −20° C.

9.4. Preparation of DNA Standards for QM Assays 9.4.1. Preparation of Quantification Standards 2,000 ng batches of human genomic DNA (Promega) were treated with bisulfite. For this 100 μl DNA (2,000 ng) are mixed with 354 μl bisulfite solution and 146 μl dioxane solution. Therefore the following temperature program was applied for bisulfite reaction: 1. Water bath at 95° C. for 3 min; 2. Thermomixer at 50° C. for 30 min, shaking at 1,000 rpm; 3. Water bath at 95° C. for 3 min.; 4. Thermomixer 50° C., 1.5 hours, shaking at 1,000 rpm; 5. Waterbath 95° C., 3 min; 6. Thermomixer 50° C. for 3 hours, shaking 1,000 rpm). The desalting, washing and desulfonation was done via MICROCON™ YM-30 columns (MILLIPORE®/AMICON®) following the working instructions. Quantification of the standard DNA was done with UV spectrometer.

9.4.2. Preparation of Calibration Standards

Molecular-Displacement (MDA) DNA

Molecular-displacement (MDA) DNA is generated according to the GenomiPhi™ DNA amplification kit (Amersham Bioscience). In brief, genomic DNA is applied to Phi-DNA-polymerase in the presence of random primers. This leads to a whole genome amplification of DNA fragments which are unmethylated.

Sss1 Treatment

To generate methylated MDA DNA, 13 tubes of 4.5 μg MDA-DNA (700 ng/μl) was treated with Sss1 in the following reaction with a total volume of 75 μl (keep reaction-solutions on ice):

4.5 μg MDA-DNA (6.3 μl)
57.3 μl H$_2$O
0.375 μl 200×SAM
3 μl (12 U) Sss1
7.5 μl NE-buffer2

Incubation was performed at 37° C. in a water bath. After appr. 3 h, 0.375 μl SAM was added and after another 5 h, 3 μl Sss1 were added (2 times). Incubate over night and subsequently inactivate at 65° C. for 10 min. Pool all 13 tubes (975 μl) take 967 μl and place DNA in a new 10 ml Falcon tube. Add 2 times 967 μl water (20 ng/μl) and aliquotate the DNA in 25×1.5 ml EPPENDORF® tubes containing 100 μl each (2 μg).

Bisulfite Treatment of MDA-DNA Sss1 Treated 24 tubes each 2 μg were bisulfite treated. This was done by mixing 100 μl DNA with 354 μl bisulfite solution and 146 μl dioxane solution. Thereafter the following temperature program was applied for bisulfite reaction: 1. Waterbath at 95° C., 3 min.; 2. Thermomixer at 50° C., 30 min, shaking at 1,000 rpm; 3. Waterbath at 95° C. 3 min.; 4. Thermomixer 50° C., 1.5 hours, shaking at 1,000 rpm; 5. Waterbath 95° C. for 3 min.; 6. Thermomixer 50° C., shaking 1,000 rpm, 3 hours. The desalting, washing and desulfonation was done via MICROCON™ YM-30 columns (MILLIPORE®/AMICON®).

Bisulfite Treatment of MDA-DNA not Sss1 Treated

For bisulfite treatment of MDA-DNA, take 82.9 μl MDA-DNA (700 ng/μl) and place in a new 10 ml Falcon tube. Add 3 times 939 μl water (20 ng/μl), aliquotate the DNA in 25 1.5 ml EPPENDORF® tubes containing 100 μl each (2 μg), perform 24 times the following: Mix 100 μl DNA with 354 μl bisulfite solution and 146 μl dioxane solution and apply thereafter the following temperature program for bisulfite reaction: 1. Waterbath at 95° C., 3 min.; 2. Thermomixer at 50° C., 30 min, shaking at 1,000 rpm; 3. Waterbath at 95° C. 3 min.; 4. Thermomixer 50° C., 1.5 hours, shaking at 1,000 rpm; 5. Waterbath 95° C. for 3 min.; 6. Thermomixer 50° C., shaking 1,000 rpm, 3 hours. The desalting, washing and desulfonation was done via MICROCON™ YM-30 columns (MILLIPORE®/AMICON®).

Quantification of Bisulfite Converted MDA-DNA Sss1 Treated—and MDA-DNA not Sss1 Treated MDA-DNA Sss1 treated and MDA-DNA not Sss1 treated was diluted 1 to 2 and 1 to 10 each sample, and DNA concentration was determined in duplicates using the C3 assay and the quantification standard prepared according to 9.4.1. Both standards were diluted 1 to 10 and 1 to 100. Afterwards, 10 µl were used for UV quantification.

Determination of Sulfite Concentration in MDA-DNA Sss1 Treated—and MDA-DNA not Sss1 Treated Determination of residual sulfite was performed using the Merck Sulfit-Küvettentest 1.1 (Merck, Darmstadt) according to the procedure described for sample measurement. The sulfite concentrations were below 100 mg/l resulting in values further below the critical value of 50 mg/l sulfite in the PCR via dilution of the stock solution.

Preparation of Calibration Standard Mixtures

Calibration standards were prepared using the stock solutions of MDA-DNA Sss1 treated—and of MDA-DNA not Sss1 treated separately for the samples sets of the ER+N0 untreated population and ER+N0 TAM treated population according to Table 1a. For that, we prepared DNA solutions of 14 different methylation level (logarithmical series) with the concentration of 1 ng/µl and distributed 40 µl of each level to several 96 well plates (plate 05) for automatic pipetting into 384 well assay plates.

TABLE 1a

Preparation of calibration standards. MDA-DNA Sss1 treated - and MDA-DNA not Sss1 treated were mixed in the indicated ratios.

| STARNDARD DNAs MDA DNA | | | 22.0 ng/µl | Sss1 treated MDA-DNA | | | 28 µg/µl |
|---|---|---|---|---|---|---|---|
| % methylation | up | down | ng needed | ng up | ng down | µl up | µl down | +µl H2O -> 10 ng/µl |
| 0 | 0 | 1.00 | 1500 | 0 | 1500 | 0 | 75 | 90 |
| 4 | 0.04 | 0.98 | 1500 | 60 | 1440 | 2.36 | 72 | 90.64 |
| 10 | 0.1 | 0.90 | 1500 | 150 | 1350 | 5.89 | 67.5 | 91.61 |
| 17 | 0.17 | 0.83 | 1500 | 255 | 1245 | 10.02 | 62.25 | 92.73 |
| 25 | 0.25 | 0.75 | 1500 | 375 | 1125 | 14.73 | 56.25 | 94.02 |
| 34 | 0.34 | 0.66 | 1500 | 510 | 990 | 20.04 | 49.5 | 95.46 |
| 44 | 0.44 | 0.56 | 1500 | 660 | 840 | 25.93 | 42 | 97.07 |
| 50 | 0.5 | 0.50 | 1500 | 750 | 750 | 29.46 | 37.5 | 98.04 |
| 56 | 0.56 | 0.44 | 1500 | 840 | 660 | 33 | 33 | 99 |
| 66 | 0.66 | 0.34 | 1500 | 990 | 510 | 38.89 | 25.5 | 100.61 |
| 75 | 0.75 | 0.25 | 1500 | 1125 | 375 | 44.2 | 18.75 | 102.05 |
| 83 | 0.83 | 0.17 | 1500 | 1245 | 255 | 48.91 | 12.75 | 103.34 |
| 90 | 0.9 | 0.10 | 1500 | 1350 | 150 | 53.04 | 7.5 | 104.46 |
| 96 | 0.96 | 0.04 | 1500 | 1440 | 60 | 56.57 | 3 | 105.43 |
| 100 | 1 | 0.00 | 1500 | 1500 | 0 | 58.93 | 0 | 106.07 |
| | | | | | | 441.96 | 562.5 | |

Verification of Methylation Status of Bisulfite Treated DNA

To check the methylation status of the MDA-DNA Sss1 treated—and MDA-DNA not Sss1 treated, a bisulfite sequencing was performed. Both types of DNA were amplified using the following primer pairs producing fragments covering the regions that were amplified by the QM assays. The length of the PCT products for sequencing is between 200 and 500 bp.

Primer 2064:300P22
Seq ID NO 1:
GGAGGGGGTAGAGTTATTAGTT

Primer 2064:514O22
Seq ID NO 2:
TATACTTCCTCAAACAACCCTC

Primer 4063:1431P22
Seq ID NO 3:
GTGATATTTGGGGATTGTTATT

Primer 4063:1868O20
Seq ID NO 4:
ACTCCCTCCCCTATCTTACA

Primer 15665:699P21
Seq ID NO 5:
TTTGTTGGGATTTGTTAGGAT

Primer 15665:1124O22
Seq ID NO 6:
AAACATTTTACCCCTCTAAACC

Primer 15947:907P24
Seq ID NO 7:
TGATTGTGTAGATTATTTTTGGTT

Primer 15947:1360O23
Seq ID NO 8:
CAAACTCTCTAAACCTCAATCTC

Primer 2265:176P22
Seq ID NO 9:
TTGGTGATGTTGATTAGAGTTT

Primer 2265:582O22
Seq ID NO 10:
TAAAACACCTTACATTTTCCCT

Primer 15908:782P22
Seq ID NO 11:
GGTAGAGGAAGTAGTTGGTTTG

Primer 15908:1228O23
Seq ID NO 12:
CTTTTATATTTCTCCCAATCTCC

Primer 0003522:2102Q21
Seq ID NO 13:
GTAGGGGAGGGAAGTAGATGT

Primer 0003522:1738R23
Seq ID NO 14:
TCCTCAACTCTACAAACCTAAAA

Bisulfite sequencing was done according to standard protocols and was performed on a ABI 3770 sequencer (96 well plate). The expected sequences and methylation ratios could be confirmed for the used fragments (data not shown).

9.5. Quantification and Adjustment of Bisulfite DNA Concentration 9.5.1. Determination of Sulfite Concentration in Bisulfite DNA Increased concentrations of residual sulfite influence the QM-assay. Therefore, we decided to determine the sulfite concentration for each of the bisulfite treated samples of both sample sets. Increased sulfite (higher 50 mg/l in the PCR reaction) affects the PCR amplification of the bisulfite DNA resulting in higher CT-values compared to sulfite concentrations below this range. CT-values represent the threshold cycle or the crossing point of a real time PCR.

Sodium sulfite was used to prepare a sulfite standard stock solution with 1 g/1 $SO_3^{2-}$ in 1×TE buffer. We produced standard solutions from 100 mg/l to 1.56 mg/l sulfite via stepwise dilution and intensive vortexing between 2 dilution steps to produce the standard curve.

TABLE 2

Sulfite-standards for sulfite test.
Sulfite-standards for sulfite test in 384 MTP

| number | addition of standard in µl | solution number | addition TE µl | conzentration $SO_3^{2-}$ [mg/l] |
|---|---|---|---|---|
| 1 | 100 | Stock | 900 | 100 |
| 2 | 500 | 1 | 500 | 50 |
| 3 | 500 | 2 | 500 | 25 |
| 4 | 500 | 3 | 500 | 12.5 |
| 5 | 500 | 4 | 500 | 6.25 |
| 6 | 500 | 5 | 500 | 3.13 |
| 7 | 500 | 6 | 500 | 1.56 | sample stock and 27 µl of ddH$_2$O were mixed. 10 µl of the pre-diluted sample and 10 µl sulfite reagent (Sulfit-Küvettentest-Merck, 1.14394.0001) was placed in a 384 well plate and vortexed. After 2 minutes of waiting time the absorbance of the solution was measured with a Photometer-Plate reader at 412 nm. The sulfite concentration was determined according to the calibration curve in mg/l sulfite.

Results

The amount of sulfite determined for the stock solution of all samples of the ER+N0 untreated population were between 0-390 mg/l. The sulfite amount was reduced up to 0-30 mg/l for the entire sample set after adjustment of the sample concentration to 1 ng/µl, except for 1 sample. Here we measured exactly the limit value of 100 mg/l.

The sulfite concentration of the sample set ER+N0 TAM treated Population was determined with 0-1195 mg/l sulfite. The sulfite concentration for 7 samples was in a critical, but still acceptable range (between 50 and 100 mg/l) and for 2 samples over 100 mg/l (120 mg/l).

In conclusion, residual sulfite in bisulfite treated DNA was no major issue.

9.5.2. Real-time PCR Based Quantification of Bisulfite DNA

The GSTP1-C3 assay design makes it suitable for quantitating DNAs from different sources, including fresh/frozen samples, remote samples such as plasma or serum, and DNA obtained from archival specimen such as paraffin-embedded formalin-fixed material. Table 3 provides an overview of fragment and oligonucleotide sequences.

TABLE 3

Sequence information of C3 fragment and oligos

```
GSTP1 gene - Genbank number for genomic sequence:
AY324387

GSTP1-C3           130 bp
bis-sequence

Seq ID No 15:
GGAGTGGAGGAAAtTGAGAtttAtTGAGGTTACGTAGTTTGtttAAGGTt
AAGttTGGGTGttTGtAATttTTGttttTGTGttAGGtTGttTttttAGGTG
TtAGGTGAGtTtTGAGtAttTGtTGTGTGG Primer 2111.C3F    Seq ID NO 16:
                   GGAGTGGAGGAAAtTGAGAt Primer 2111.C3R    Seq ID NO 17:
                   CCACACAaCAaaTaCTCAaAaC TAQMAN ™ probe C3-TAQ2            Seq ID NO 18:
                   FAM-TGGGTGTTTGTAATTTTTGTTTTGTTTA
                   GGTT-TAMRA
```

The preparation of the quantification standard DNA was described in 9.4.1. The DNA concentration was adjusted between 4-0.0312 ng/µl and placed into a 96 well format for automatic pipetting into a 384 well PCR assay plate. Each calibration standard DNA was amplified up to 3× (light green on the 96 well plate and 384 PCR plate).

TABLE 4

DNA amounts and serial dilution steps for quantification of bisulfite treated DNA samples.

| ng DNA per PCR | Step__ and dilution of stock |
|---|---|
| 40.000 ng | 1__ 1 |
| 20.000 ng | 2__ 1:2 |
| 10.000 ng | 3__ 1:4 |
| 5.000 ng | 4__ 1:8 |
| 2.500 ng | 5__ 1:16 |
| 1.250 ng | 6__ 1:32 |
| 0.625 ng | 7__ 1:64 |

TABLE 5

96 well plate with calibration standard DNA, plate 05.
96 well plate with quantification standard, plate 05

|   | 1 | 2 | 3 | 4 | 5 | 6 | 7 | 8 | 9 | 10 | 11 | 12 |
|---|---|---|---|---|---|---|---|---|---|---|---|---|
| A | 40 ng | Ntc | | | | | | | | | | |
| B | 20 ng | Ntc | | | | | | | | | | |
| C | 10 ng | Ntc | | | | | | | | | | |
| D | 5 ng | Ntc | | | | | | | | | | |
| E | 2.5 ng | | | | | | | | | | | |
| F | 1.25 ng | | | | | | | | | | | |
| G | 0.625 ng | | | | | | | | | | | |
| H | 0.312 ng | | | | | | | | | | | |

(Ntc. = No template control)

The Mastermix for the entire 384 PCR plate was pipetted according to Table 6, mixed in a 15 ml falcon tube and distributed to 8×500 µl screw cap vials for automatic pipetting with TECAN® workstation.

TABLE 6

PCR mastermix preparation for C3 assay quantification.

| solution | Concentration | volume | final concentration | provider |
|---|---|---|---|---|
| PCR buffer | 10x | 2 µl | 1x | Eurogentec |
| dNTP mix | 25 mmol/l (each) | 0.2 µl | 250 µmol/l (each) | Fermentas |
| MgCl$_2$ | 25 mmol/l | 2.4 µl | 3 mmol/l | Eurogentec |
| DNA polymerase | 5 U/µl | 0.2 µl | 1 unit | Eurogentec |
| Primer mixture | 5 µmol/l (each) | 1.25 µl | 0.313 µmol/l | MWG |
| TAQMAN ™ probe | 10 µmol/l | 0.6 µl | 0.3 µmol/l | TibMolBiol |
| water | — | 3.35 µl | — | Fluka |
| diluted DNA | — | 10 µl | — | — |
| Total react. volume | | 20 µl | | |

TABLE 7

PCR cycling conditions for C3 assay at ABI 7700 or 7900 instrument.

| 1 | Initial denaturation | 95° C. | 10 min |
|---|---|---|---|
| 2 | Denaturation | 95° C. | 15 sec |

TABLE 7-continued

PCR cycling conditions for C3 assay at ABI 7700 or 7900 instrument.

| 3 | Annealing/extension | 58° C. | 60 sec |
| 4 | Cycling | Repeat steps (2 + 3) 45x | |

The bisulfite treated DNA samples of the ER+N0 untreated population were stored in 7×96 well plates (plate 01-07) and of the ER+N0 untreated population in 8×96 well plates (plate 01-08). To quantify all samples, 3 µl of the sample was taken and 27 µl water were added. This results in a 1:10 dilution of the DNA stock concentration. Furthermore additional 3 µl of the first dilution (1:10) were diluted again with 27 µl of water to obtain a 1:100 dilution of the stock DNA. This process results in 2 dilution plates (1:10 and 1:100) for each sample DNA in separate 96 well plates. The 384 PCR plates for quantification were pipetted with the TECAN® workstation using always 4 (2×1:10 dilution and 2×1:100 dilution)×96 well plates. So each quantification PCR run quantified 2 of the DNA stock plates in 2 replicates next to each other for each DNA sample. The pipetting program of the TECAN® workstation transferred first 10 µl of the Mastermix and afterwards 10 µl of the respective DNA into the designed well. So DNAs from plate 01 and 02 (one DNA stock plate) result in orange colors and from plate 03 and 04 in blue colors on the 384 well PCR plate. Standard DNA wells are marked in light green and negative control PCR reactions in dark green on the final plate.

TABLE 8

96 well plate with bisulfite treated samples (1:10 and 1:100 dilution).

| | 1 | 2 | 3 | 4 | 5 | 6 | 7 | 8 | 9 | 10 | 11 | 12 |
|---|---|---|---|---|---|---|---|---|---|---|---|---|
| A | 01A1 | 01A2 | 01A3 | 01A4 | 01A5 | 01A6 | 01A7 | 01A8 | 01A9 | 01A10 | 01A11 | |
| B | 01B1 | 01B2 | 01B3 | 01B4 | 01B5 | 01B6 | 01B7 | 01B8 | 01B9 | 01B10 | 01B11 | |
| C | 01C1 | 01C2 | 01C3 | 01C4 | 01C5 | 01C6 | 01C7 | 01C8 | 01C9 | 01C10 | 01C11 | |
| D | 01D1 | 01D2 | 01D3 | 01D4 | 01D5 | 01D6 | 01D7 | 01D8 | 01D9 | 01D10 | 01D11 | |
| E | 01E1 | 01E2 | 01E3 | 01E4 | 01E5 | 01E6 | 01E7 | 01E8 | 01E9 | 01E10 | 01E11 | |
| F | 01F1 | 01F2 | 01F3 | 01F4 | 01F5 | 01F6 | 01F7 | 01F8 | 01F9 | 01F10 | 01F11 | |
| G | 01G1 | 01G2 | 01G3 | 01G4 | 01G5 | 01G6 | 01G7 | 01G8 | 01G9 | 01G10 | 01G11 | |
| H | 01H1 | 01H2 | 01H3 | 01H4 | 01H5 | 01H6 | 01H7 | 01H8 | 01H9 | 01H10 | 01H11 | |

TABLE 9

384 well PCR plate for quantification.

| Layout | 1 | 2 | 3 | 4 | 5 | 6 | 7 | 8 | 9 | 10 | 11 | 12 |
|---|---|---|---|---|---|---|---|---|---|---|---|---|
| A | 01A1 | 02A1 | 05A1 | 01A4 | 02A4 | 01A6 | 02A6 | 01A8 | 02A8 | 01A10 | 02A10 | 01C3 |
| B | 01A2 | 02A2 | 01A3 | 02A3 | 01A5 | 02A5 | 01A7 | 02A7 | 01A9 | 02A9 | 01A11 | 02A11 |
| C | 01B1 | 02B1 | 05B1 | 01B4 | 02B4 | 01B6 | 02B6 | 01B8 | 02B8 | 01B10 | 02B10 | 01G8 |
| D | 01B2 | 02B2 | 01B3 | 02B3 | 01B5 | 02B5 | 01B7 | 02B7 | 01B9 | 02B9 | 01B11 | 02B11 |
| E | 01C1 | 02C1 | 05C1 | 01C4 | 02C4 | 01C6 | 02C6 | 01C8 | 02C8 | 01C10 | 02C10 | 05A1 |
| F | 01C2 | 02C2 | 05A2 | 05A2 | 01C5 | 02C5 | 01C7 | 02C7 | 01C9 | 02C9 | 01C11 | 02C11 |
| G | 01D1 | 02D1 | 05D1 | 01D4 | 02D4 | 01D6 | 02D6 | 01D8 | 02D8 | 01D10 | 02D10 | 05B1 |
| H | 01D2 | 02D2 | 01D3 | 02D3 | 01D5 | 02D5 | 01D7 | 02D7 | 01D9 | 02D9 | 01D11 | 02D11 |
| I | 01E1 | 02E1 | 05E1 | 01E4 | 02E4 | 01E6 | 02E6 | 01E8 | 02E8 | 01E10 | 02E10 | 05C1 |
| J | 01E2 | 02E2 | 01E3 | 02E3 | 01E5 | 02E5 | 01E7 | 02E7 | 01E9 | 02E9 | 01E11 | 02E11 |
| K | 01F1 | 02F1 | 05F1 | 01F4 | 02F4 | 01F6 | 02F6 | 01F8 | 02F8 | 01F10 | 02F10 | 05D1 |
| L | 01F2 | 02F2 | 01F3 | 02F3 | 01F5 | 02F5 | 01F7 | 02F7 | 01F9 | 02F9 | 01F11 | 02F11 |
| M | 01G1 | 02G1 | 05G1 | 01G4 | 02G4 | 01G6 | 02G6 | 05B2 | 05B2 | 01G10 | 02G10 | 03C2 |
| N | 01G2 | 02G2 | 01G3 | 02G3 | 01G5 | 02G5 | 01G7 | 02G7 | 01G9 | 02G9 | 01G11 | 02G11 |
| O | 01H1 | 02H1 | 05H1 | 01H4 | 02H4 | 01H6 | 02H6 | 01H8 | 02H8 | 01H10 | 02H10 | 03F9 |
| P | 01H2 | 02H2 | 01H3 | 02H3 | 01H5 | 02H5 | 01H7 | 02H7 | 01H9 | 02H9 | 01H11 | 02H11 |

| | 13 | 14 | 15 | 16 | 17 | 18 | 19 | 20 | 21 | 22 | 23 | 24 |
|---|---|---|---|---|---|---|---|---|---|---|---|---|
| A | 02C3 | 03A2 | 03A2 | 03A4 | 04A4 | 03A6 | 04A6 | 03A8 | 04A8 | 05A1 | 03A10 | 04A10 |
| B | 03A1 | 04A1 | 03A3 | 04A3 | 03A5 | 04A5 | 03A7 | 04A7 | 03A9 | 04A9 | 03A11 | 04A11 |
| C | 02G8 | 03B2 | 04B2 | 03B4 | 04B4 | 03B6 | 04B6 | 03B8 | 04B8 | 05B1 | 03B10 | 04B10 |
| D | 03B1 | 04B1 | 03B3 | 04B3 | 03B5 | 04B5 | 03B7 | 04B7 | 03B9 | 04B9 | 03B11 | 04B11 |
| E | 05E1 | 05C2 | 05C2 | 03C4 | 03B5 | 03G6 | 03C8 | 03C8 | 04C8 | 05C1 | 03C10 | 04C10 |
| F | 03C1 | 04C1 | 03C3 | 04C3 | 04G4 | 04G5 | 03C7 | 04C7 | 03C9 | 04C9 | 03C11 | 04C11 |
| G | 05F1 | 03D2 | 04D2 | 03D3 | 03C5 | 03D6 | 04D6 | 03D8 | 04D8 | 05D1 | 03D10 | 04D10 |
| H | 03D1 | 04D1 | 03D3 | 03E4 | 04D4 | 04D5 | 03D7 | 04D7 | 03D9 | 04D9 | 03D11 | 04D11 |
| I | 05G1 | 03E2 | 04E2 | 04E3 | 03D5 | 03E6 | 04E6 | 03E8 | 04E8 | 05E1 | 03E10 | 04E10 |
| J | 03E1 | 04E1 | 03E3 | 03F4 | 04E4 | 04E6 | 03E7 | 04E7 | 03E9 | 04E9 | 03E11 | 04E11 |
| K | 05H1 | 03F2 | 04F2 | 04F3 | 03E5 | 03F6 | 04E6 | 03F8 | 04F8 | 05F1 | 03F10 | 04F10 |
| L | 03F1 | 04F1 | 03F3 | 04F3 | 04F4 | 04F6 | 03F7 | 04F7 | 05D2 | 05D2 | 03F11 | 04F11 |
| M | 04C2 | 03G2 | 04G2 | 03G4 | 04G4 | 03G6 | 04G6 | 03G8 | 04G8 | 05G1 | 03G10 | 04G10 |
| N | 03G1 | 04G1 | 03G3 | 04G3 | 03G5 | 04G5 | 03G7 | 04G7 | 03G9 | 04G9 | 03G11 | 04G11 |
| O | 04F9 | 03H2 | 04H2 | 03H4 | 04H4 | 03H6 | 04H6 | 03H8 | 04H8 | 05H1 | 03H10 | 04H10 |
| P | 03H1 | 04H1 | 03H3 | 04H3 | 03H5 | 04H5 | 03H7 | 04H7 | 03H9 | 04H9 | 03H11 | 04H11 |

Results of Quantification

TABLE 10

Results of C3 quantification on fresh frozen samples (ER+ N0 untreated population).
ER+ N0 untreated population

| Amount of DNA quantified with C3, ng | Concentration of DNA, ng/µl | Number of samples |
|---|---|---|
| 1807-9992 | 40-222 | 57 |
| 900-1732 | 20-40 | 112 |
| 454-898 | 10-20 | 181 |
| 225-442 | 5-10 | 90 |
| 87.3-221 | 2-5 | 36 |
| 41.5-81.5 | 1-2 | 10 |
| 11.7-41.0 | 0.25-1 | 10 |
| 0 | 0.0 | 12 |

TABLE 11

Results of C3 quantification on paraffin-embedded formalin-fixed (PET) samples (ER+ N0 TAM treated population).
ER+ N0 TAM treated Population

| Amount of DNA quantified with C3 assay, ng | Concentration of DNA, ng/µl | Number of samples |
|---|---|---|
| 1813-24500 | 40-545 | 75 |
| 905-1795 | 20-40 | 52 |
| 452-886 | 10-20 | 74 |
| 225-447 | 5.0-10.0 | 72 |
| 90.4-225 | 2.0-5.0 | 98 |
| 45.4-88.4 | 1.0-2.0 | 69 |
| 4.7-45.2 | 0.1-1 | 96 |
| 0.24-4.5 | 0.01-0.1 | 33 |
| 0.0 | 0.0 | 20 |

9.5.3. Adjustment of DNA Concentration

According to the resulting concentration determined via quantification, we adjusted each sample to a concentration of 1 ng/µl if possible. This concentration results in up to 10 ng DNA in the QM assay reaction. For the adjustment, the DNA samples of one 96 well DNA stock plate were pipetted into a deep well plate using maximal 390 ng, producing a concentration adjusted copy plate (96 wells). The adjustment step was also done with the TECAN® workstation pipetting between 4 µl and 32 µl of DNA and adding the respective amount of water (up to 900 µl) to achieve 1 ng/µl. The adjusted DNA solution was afterwards transferred from deep well plates into several identical 96 well plates for final QM assay pipetting.

Note that not all samples could be adjusted to the desired concentration of 1 ng/µl due to limited material. Table 12 and Table 13 shows the distribution of actual amounts of DNA that was used in the QM assays.

TABLE 12

Final amount of DNA in QM assay for fresh frozen samples (ER+ N0 untreated population) after adjustment.
ER+ N0 untreated Population

| Amount of DNA (adjusted) in QM assay | Number of samples |
|---|---|
| 10 ng | 357 |
| 5-10 ng | 85 |
| 2-5 ng | 34 |
| 1-2 ng | 10 |
| 0-1 ng | 10 |
| 0 ng | 12 |

TABLE 13

Final amount of DNA in QM assay for paraffin-embedded formalin-fixed (PET) samples (ER+ N0 TAM treated population) after adjustment.
ER+ N0 TAM treated Population

| Amount of DNA (adjusted) in QM assay | Number of samples |
|---|---|
| 10-24 ng | 9 |
| 10 ng | 263 |
| 5-10 ng | 72 |
| 2-5 ng | 96 |
| 1-2 ng | 41 |
| 0-1 ng | 88 |
| 0 ng | 20 |

9.6. QM Assay Runs

The bisulfite treated DNA and concentration adjusted samples of the ER+N0 untreated population were stored in 7×96 well plates (plate 01-07) and of the ER+N0 untreated population in 8×96 well plates (plate 01-08). To measure the entire sample set of both populations we run 2×384 PCR reaction plates for each QM assay and population. Each QM assay plate contains the samples of 3 or 4×96 well plates (88 wells actually used per plate) and 1×96 well plate with standard DNA (14 mixtures of the calibration DNA and water for the no template control PCR reaction, see Table 15 below). Repetitions of sample measurements were done by repeating the QM assay run 3 times.

The 384 PCR plates were also pipetted with the TECAN® workstation. The pipetting program transferred at first 10 µl of the mastermix and afterwards 10 µl of the respective DNA into the designed well. As described for the quantification step, DNAs from plate 01 and 02 result in orange colors and from plate 03 and 04 in blue colors on the 384 well PCR plate (see 9.5.2.). Standard DNA wells are signed in light green and negative control PCR reactions in dark green on the final plate. The components of the mastermix for each QM assay were adapted according the table 14. The mixture was pipetted in a falcon tube and distributed to 8×500 µl screw cap vials for automatic pipetting with TECAN® workstation.

TABLE 14

PCR components for 384 well PCR plate (e.g. for QM assay3522-II).

| number of reactions: 384 component | 384 stock conc. | Factor: 1.1 µl/reaction | µl in MM | final conc. |
|---|---|---|---|---|
| Ampli reaction buffer | 10x | 2 | 844.8 | 1x |
| Ampli MgCl2 | 25 mmol/l | 2 | 844.8 | 2.5 mmol/l |
| dNTPs | 25 mmol/l each | 0.2 | 84.48 | 250 µmol/l |
| primer mix | 6.25 µmol/l | 2 | 844.8 | 625 nmol/l |
| cg-probe | 4 µmol/l | 1 | 422.4 | 200 nmol/l |
| Tg-probe | 4 µmol/l | 1 | 422.4 | 200 nmol/l |
| AmpliTaqGold | 5 U/µl | 0.2 | 84.48 | 1 U |
| water | | 1.6 | 675.84 | Ad 10 |
| | | 10 | 4224 | |

TABLE 15

Calibration standard DNA mixtures and no template control (plate 05).

96 well plate

|   | 1 | 2 | 3 | 4 | 5 | 6 | 7 | 8 | 9 | 10 | 11 | 12 |
|---|---|---|---|---|---|---|---|---|---|----|----|----|
| A | 0%  | 66%  | Ntc |   |   |   |   |   |   |   |   |   |
| B | 4%  | 75%  | Ntc |   |   |   |   |   |   |   |   |   |
| C | 10% | 83%  | Ntc |   |   |   |   |   |   |   |   |   |
| D | 17% | 90%  | Ntc |   |   |   |   |   |   |   |   |   |
| E | 25% | 96%  |     |   |   |   |   |   |   |   |   |   |
| F | 34% | 100% |     |   |   |   |   |   |   |   |   |   |
| G | 44% |      |     |   |   |   |   |   |   |   |   |   |
| H | 56% |      |     |   |   |   |   |   |   |   |   |   |

(Ntc = No template control)

All QM assays were run on a ABI TAQMAN™ 7900HT real-time device (SDS 2.2. software) with a reaction volume of 20 µl and 9600 emulation (emulation of ABI TAQMAN™ 7700). An automatic sample setup was used to transfer the correct sample names and detector/reporter dyes to the TAQMAN™ software. The cycling conditions were manually adjusted (Table 16) and ROX was used as passive reference dye.

TABLE 16

Optimized MgCl$_2$ concentrations and annealing temperatures of QM assays.

| Assay    | Gene    | MgCl$_2$ conc. | Annealing Temp. |
|----------|---------|----------------|-----------------|
| 3522 I   | PITX2   | 3 mM           | 62° C.          |
| 3522 II  | PITX2   | 2.5 mM         | 60° C.          |
| 2395     | PLAU    | 2.5 mM         | 60° C.          |
| 2064     | ERBB2   | 2.5 mM         | 62° C.          |
| 15908 II | TBC1D3  | 4.5 mM         | 60° C.          |
| 15665    | ONECUT2 | 3 mM           | 60° C.          |
| 15947    | ABCA8/9 | 3 mM           | 62° C.          |
| 2265     | TFF1    | 2.5 mM         | 60° C.          |

All 384 well PCR plates we re-analyzed by the SDS2.2 software using the manual analysis settings (baseline setting with start and stop values and manual threshold) to produce results files for each run individually.

Example 10

DNA Quantification Methods a) UV Determination of Physical DNA Concentration

UV quantification was performed to determine the total amount of DNA present including DNA which cannot be amplified using a real time PCR based approach. UV quantification was done by using a standard spectrophotometer for example the UV mini 1240 UV-VIS spectrophotometer (Shimadzu).

b) Real Time PCR Determination of Bisulfite Converted DNA (HB14 Assay) by Means of a LIGHTCYCLER™ Instrument (Roche)

Real time PCR quantification specifically detects bisulfite converted DNA. Only DNA which is not affected by degradation due to formalin fixation, paraffin embedding and storage is quantified using a real time PCR approach. The quantification was performed in a total volume of 20 µl containing 10 µl template DNA or a dilution thereof, 1 U or 3 U FastStart Taq DNA polymerase (Roche), respectively, 4 mmol/l MgCl$_2$, 500 nmol/l (each) forward and reverse primers (forward primer Seq ID NO 19: TGGTGATGGAGGAGGTTTAGTAAGT, reverse primer Seq ID No 20: AACCAATAAAACCTACTCCTCCCTTAA), 1×PCR buffer (Roche), 0.25 mmol/l or 0.5 mmol/l of each dNTP (Fermentas), respectively, 0.25 mg/ml BSA (Sigma Aldrich) and 250 nmol/l of each detection probe (Seq ID NO 21: TTGTGAATTTGTGTTTGTTATTGTGTGTTG-Fluo and Seq ID NO 22: Red640-TGGTGGTTATTTTTTTTATTAGGT-TGTGGT-Phosphate). Cycling was done using a LIGHTCYCLER™ detection System (Roche) with the following conditions: 10 min at 95° C. and 40 cycles at 95° C. for 10 s, 58° C. for 20 s, 72° C. for 10 s or 72° C. for 70 s, detection at 58° C., and ramping rates 20° C./s. The amplification results in 133 bp fragments.

c) Real Time PCR Determination of Bisulfite Converted DNA (C3 Assay) by Means of a 7900HT Fast Real-Time PCR System (Applied Biosystems)

The C3 assay specifically detects bisulfite converted DNA. Real time PCR quantification (C3 assay) was performed in a total volume of 20 µl containing 10 µl template DNA or a dilution thereof, 1 U HotGoldStar polymerase (Eurogentec), 3 mmol/l MgCl$_2$, 625 nmol/l (each) forward and reverse primers (forward primer Seq ID NO 23: GGAGTGGAGGAAATTGAGAT, reverse primer Seq ID NO 24: CCACACAACAAATACTCAAAAC), 1× reaction buffer containing ROX passive reference (Eurogentec), 0.25 mmol/l of each dNTP (Fermentas) and 200 nmol/l detection probe (Seq ID NO 25: FAM-TGGGTGTTTGTAATTTTTGTTTTGTGT-TAGGTT-EclipseDQ or BNQ1). Cycling was done using a Applied Biosystems 7900HT Fast Real-Time PCR System with the following conditions: 10 min at 95° C. and 40 cycles at 95° C. for 15 s, 58° C. for 60 s, detection at 72° C., and ramping rates 3° C./s.

d) Real Time PCR Based Simultaneous Determination of Bisulfite Converted and Unconverted DNA (CFF1 Assay) by Means of a 7900HT Fast Real-Time PCR System (Applied Biosystems)

The CFF1 assay is located in a region without any cytosines and therefore this region is not affected by the bisulfite conversion. Accordingly, this assay enables the determination of both, genomic and bisulfite converted DNA simultaneously. Real time PCR quantification (CFF1 assay) was performed in a total volume of 20 µl containing 10 µl template DNA, 1 U HotGoldStar polymerase (Eurogentec), 2.5 mmol/l MgCl$_2$, 625 nmol/l (each) of forward and reverse primers (forward primer Seq ID NO 26: TAAGAGTAATAATGGATGGATGATG, reverse primer Seq ID NO 27: CCTCCCATCTCCCTTCC), 1× reaction buffer containing ROX passive reference (Eurogentec), 0.25 mmol/l of each dNTP (Fermentas) and 200 nmol/l detection probe (Seq ID NO 28: FAM-ATGGATGAAGAAAGAAAGGATGAGT-EclipseDQ or BHQ1). Cycling was done using a Applied Biosystems 7900HT Fast Real-Time PCR System with the following conditions: 10 min at 95° C. and 40 cycles at 95° C. for 15 s, 58° C. for 60 s, detection at 72° C., and ramping rates 3° C./s.

Example 11

Figure 2:
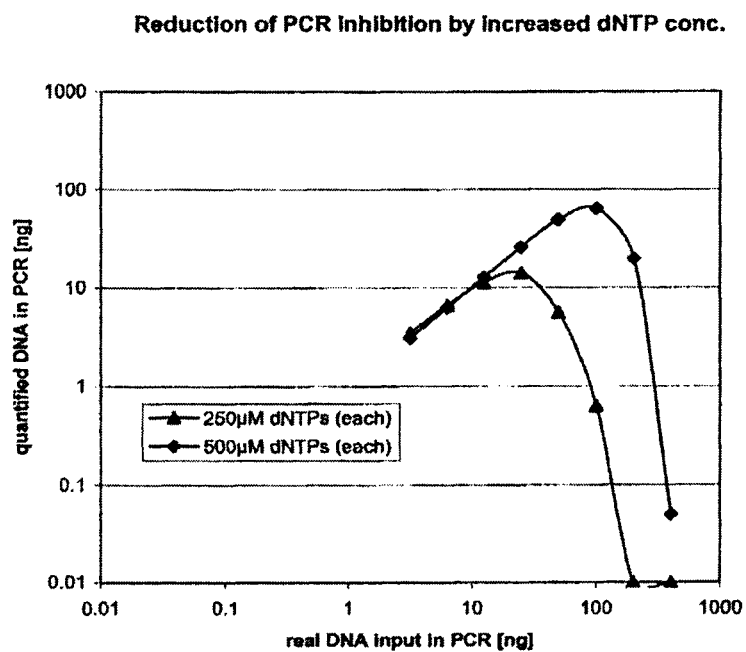
FIG. 2 shows, according to particular aspects, results of real time PCR quantification of pooled bisulfite DNA derived from different paraffin-embedded formalin-fixed specimens—Influence of dNTP concentration on PCR performance (Example 11).

Bisulfite Treated DNA Derived from Paraffin-Embedded Formalin-Fixed Tissues (PET) in Real Time PCR Several different paraffin-embedded formalin-fixed tissue (PET) specimens (4 breast, 12 gallbladder, 12 tonsil samples) were processed according to example 2. Bisulfite treated and purified DNA of these specimens was pooled and subsequently subjected to the quantitative real time PCR of example 10b (HB14 assay). FIG. 2 shows that the effective DNA input in the real time PCR quantification assay (HB14 assay) is in strong concordance to the quantified DNA amount over a wide range of DNA input amounts. The use of dNTPs each 250 µmol/l in the quantification assay leads to a reliable amplification and therefore quantification of up to 25 ng input DNA. Higher DNA inputs results in a relative decrease of amplified DNA in comparison to the effective input indicating an inhibition of the PCR. Increasing the dNTP concentration to 500 µmol/l for each nucleotide enables a proper amplification and therefore quantification of up to 100 ng of input DNA.

Figure 3:
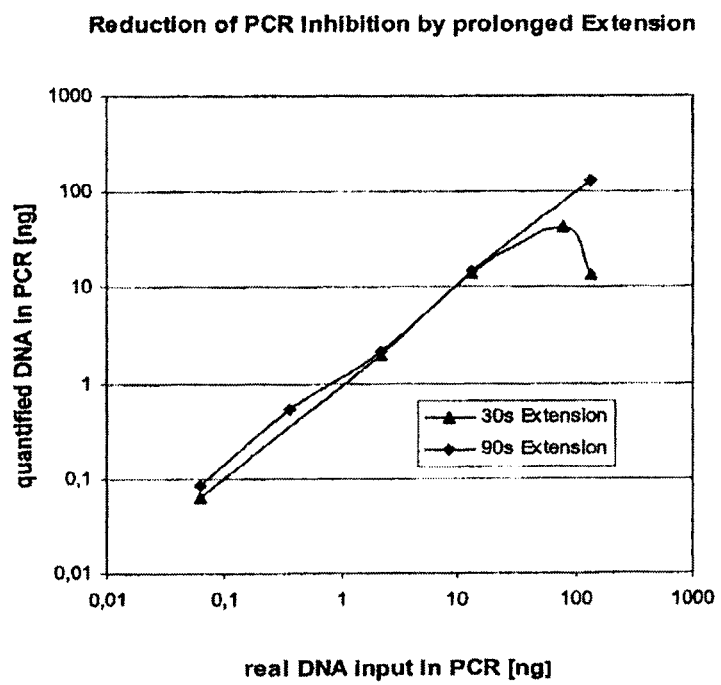
FIG. 3 shows, according to particular aspects, results of real time PCR quantification of pooled bisulfite DNA derived from different paraffin-embedded formalin-fixed specimens—Influence of extension time on PCR performance (Example 11).

A increase in the extension time within each PCR cycle also leads to a higher amplifiablity of bisulfite treated DNA derived from archived samples in case high DNA amounts are used. FIG. 3 shows the amplification and quantification of up to 130 ng input DNA using a prolonged extension time of 90 s compared to a extension time of 30 s. For this experiment, it is taken into account that the polymerase activity already starts during the annealing step at 58° C. which is therefore also regarded as extension time.

Figure 4:
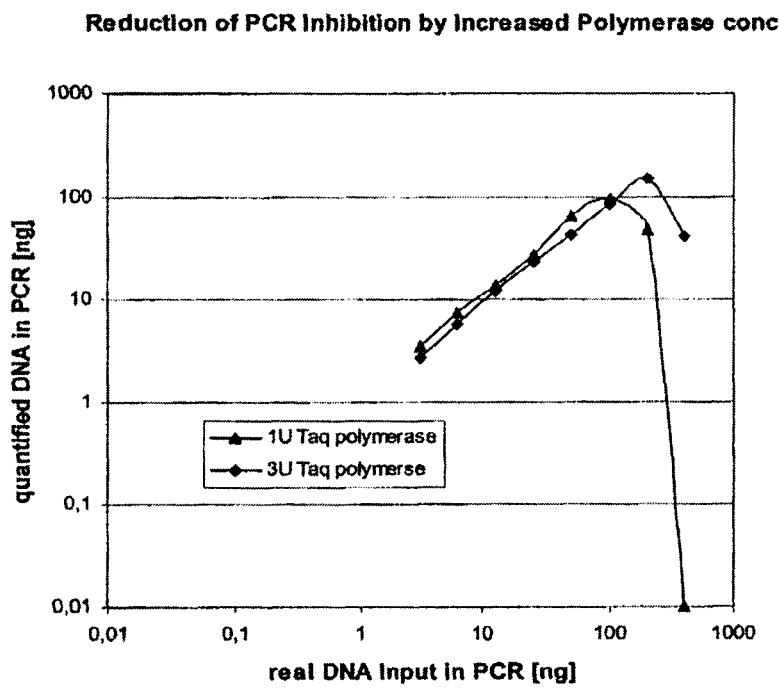
FIG. 4 shows, according to particular aspects, results of real time PCR quantification of pooled bisulfite DNA derived from different paraffin-embedded formalin-fixed specimens—Influence of polymerase amount on PCR performance (Example 11).

In case of the use of higher levels of DNA input amounts, the real time PCR performance at is also affected by the amount of polymerase. FIG. 4 shows the positive influence of the three fold increase of the polymerase activity. This increase enables the proper amplification and quantification of up to 200 ng of bisulfite DNA in a single PCR reaction.

Example 12

Processing of Tissue Sections Derived from Paraffin-Embedded Formalin-Fixed Prostate Biopsies (Processing of 2×24 Samples)

Figure 5:
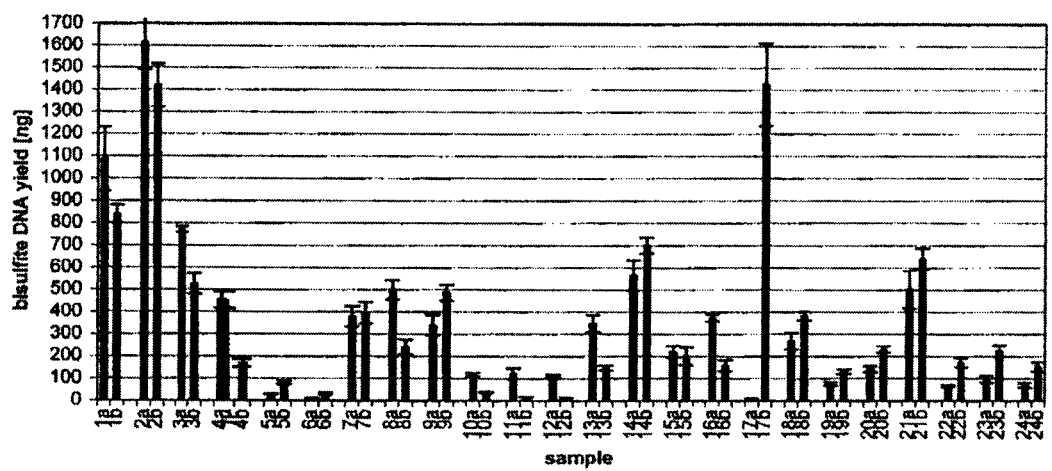
FIG. 5 shows, according to particular aspects, yield of bisulfite treated DNA after purification derived from paraffin-embedded formalin-fixed prostate biopsies (Example 12).
Figure 6:
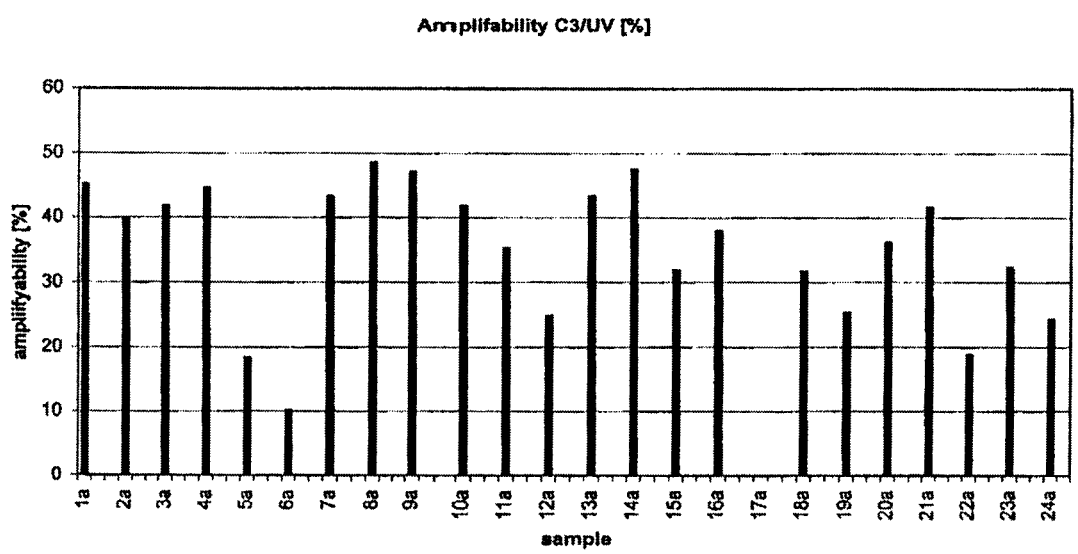
FIG. 6 shows, according to particular aspects, content of amplifiable DNA after bisulfite treatment and subsequent purification (The content is defined by the ratio of amplifiable DNA determined according to example 10c and UV value determined according to example 10a which reflects the total amount of DNA present in the sample; Example 12).

Sections from 24 different paraffin-embedded formalin-fixed prostate biopsy specimens (1-3 biopsy cores per paraffin block) were analyzed. Two samples (a and b) of each specimen each consisting of 5 sections (10 µm) were processed resulting in 48 samples in total. Samples were processed according to example 7 followed by a bisulfite treatment and DNA purification by means of Microcon™ device as described in example 8. The DNA yield after bisulfite treatment and subsequent purification was determined according to example 10c. FIG. 5 shows that the yield of bisulfite treated and purified DNA is more than 100 ng for at least one of the two samples per specimen except specimen 5 and 6. Samples of 6 specimen resulted in more than 500 ng bisulfite DNA. DNA yields from both samples of each specimens show a strong concordance. This illustrates the high reproducibility and reliability of the method according to the invention. Most samples comprise 20%-50% amplifiable DNA (FIG. 6) which is characterized by the ratio of DNA amounts resulted from the quantification by means of example 10c and of the UV value (see example 10a).

Example 13

Amplification of PCR Amplicons of Different Lengths from Paraffin-Embedded Formalin-Fixed Tissues (PET)

Several different paraffin-embedded formalin-fixed tissue (PET) specimens (4 breast, 12 gallbladder, 12 tonsil samples) were processed according to example 2. The purified DNA after bisulfite treatment was pooled and subsequently subjected to PCR in which amplicons of different lengths (185 bp-711 bp) should be amplified. PCR was performed in a total volume of 25 µl containing 1 U and 3 U Hotstar Taq polymerase (QIAGEN®), respectively, 12.5 µmol of forward and reverse primers (primer sequences are shown in table 17a), 1×PCR buffer (QIAGEN®), 0.2 mmol/l of each dNTP (Fermentas). Cycling was done using a MASTERCYCLER® (EPPENDORF®) with the following conditions: 15 min at 95° C. and 40 cycles at 95° C. for 30 s, 55° C. for 45 s and 72° C. for 1:30 min. Each PCR contained 30 ng template DNA. This amount is based on a prior real time PCR quantification as exemplified by example 10b (HB14 assay) and therefore reflecting the amplifiable partition of the physically present total DNA amount.

TABLE 17a

Amplicon sizes and the respective primer sequences. Bisulfite treated high molecular weight (HMW) DNA (human genomic DNA, Promega, USA) was used as positive control for each PCR amplicon.

| amplicon size [bp] | forward primer (5'->3') | reverse primer (5'->3') |
| --- | --- | --- |
| 185 | Seq ID No 29: TTTTTGTAGTTTAGAAGGAGGTTAG | Seq ID No 30: ACACAATAAATTCAACCACCAA |
| 210 | Seq ID No 31: GGGAGATTTAATTTGGGG | Seq ID No 32: CACCCTCTAATAACCAACCA |
| 235 | Seq ID No 33: TTAGGTATAAGTTGGTGGTGG | Seq ID No 34: CCCATAAACAACCCCTAAAA |
| 260 | Seq ID No 35: AGGTATAGGATGGGGAATTAGT | Seq ID No 36: AACCCAAACCCTTATACAAAC |
| 285 | Seq ID No 37: GTTTTTGGAGTTAATTGGGAG | Seq ID No 38: CACCCCCATCATTACTATTC |

TABLE 17a-continued

Amplicon sizes and the respective primer sequences.
Bisulfite treated high molecular weight (HMW) DNA
(human genomic DNA, Promega, USA) was used as positive
control for each PCR amplicon.

| amplicon size [bp] | forward primer (5'->3') | reverse primer (5'->3') |
|---|---|---|
| 310 | Seq ID No 39: AGGGTAGAGGGTGTTGGT | Seq ID No 40: CCAAAACTATAAACCTTCCCA |
| 335 | Seq ID No 41: TTTAGTATGGGTTGAGAGGAGT | Seq ID No 42: CCTCTTTCCTAAAACTACACATTC |
| 360 | Seq ID No 43: GGATTATTGTTGGGTATTTGTT | Seq ID No 44: ACACTTCCCTAAAATCTTCAAA |
| 385 | Seq ID No 45: GTTGGATTTGTTTAGAGAGAGG | Seq ID No 46: ACATTTAACTCTTTATCCCAAAA |
| 410 | Seq ID No 47: TTATTTGATGGGGATAGAGATT | Seq ID No 48: ACAAACAACACACCCTCATAC |
| 435 | Seq ID No 49: TGTAATGAAAGAAGGTGTTGAG | Seq ID No 50: TTAACTAAACCATCCATAACCC |
| 460 | Seq ID No 51: GGATTATAGGAATTAGAATGGGT | Seq ID No 52: TCTTTCCAACTCAACATCTTACT |
| 485 | Seq ID No 53: TGGTGGTATGGATTGGATAA | Seq ID No 54: TCCCCCAAATAACACAATATAC |
| 511 | Seq ID No 55: AGAGGAAAGAGTAAGGAATTTTT | Seq ID No 56: CTTATCCCCCACAAAACC |
| 535 | Seq ID No 57: GGTGGAGGGAGAGTTAAGG | Seq ID No 58: CCAACAAAACGCCCTCTCC |
| 561 | Seq ID No 59: GATTGAGATTATTTTGGGTTTT | Seq ID No 60: ACTTAAACCTTCCCTCTCCAC |
| 586 | Seq ID No 61: TTAAGTATTGGATTTGGGGTTA | Seq ID No 62: ACCTACCCTCTAACTCTACAAAAA |
| 606 | Seq ID No 63: AGTAAATAGTGGGTGAGTTATGAA | Seq ID No 64: AAAAACCTCTAAAAACTACTCTCC |
| 636 | Seq ID No 65: AAGGTTTTAGGGAAGAGTGTTT | Seq ID No 66: CCTTTTCCTATCACAAAAATAA |
| 660 | Seq ID No 67: AGGGGGAATTAAATAGAAAGAG | Seq ID No 68: CAATAAAACCATCCCAAATACT |
| 678 | Seq ID No 69: TATGGGAGGAGGTTAGTAAGTG | Seq ID No 70: CCCCAAATCCTACATATAAAAA |
| 711 | Seq ID No 71: GTATTATGTGGTTTAAGGAGGG | Seq ID No 72: ACTCCAAACAAATTCAACAACT |

Figure 7:
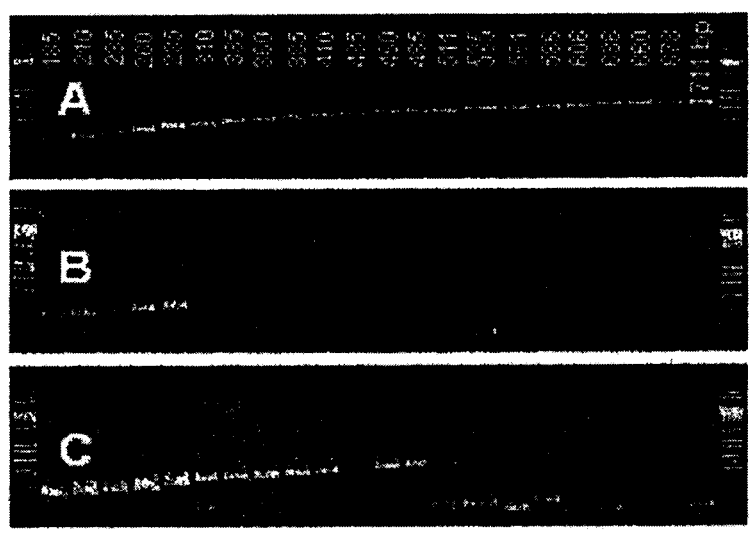
FIG. 7 shows, according to particular aspects, PCR amplification of bisulfite specific amplicons ranging from 185 bp to 711 bp. A: HMW template DNA (positive control). B: bisulfite treated and subsequently purified template DNA derived from paraffin-embedded formalin-fixed tissue. 30 ng template DNA and 1 U Taq polymerase in a total volume of 25 µl were used. C: bisulfite treated and subsequently purified template DNA derived from paraffin-embedded formalin-fixed tissue. 30 ng template DNA and 3 U Taq polymerase in a total volume of 25 µl were used (Example 13).
Figure 8:
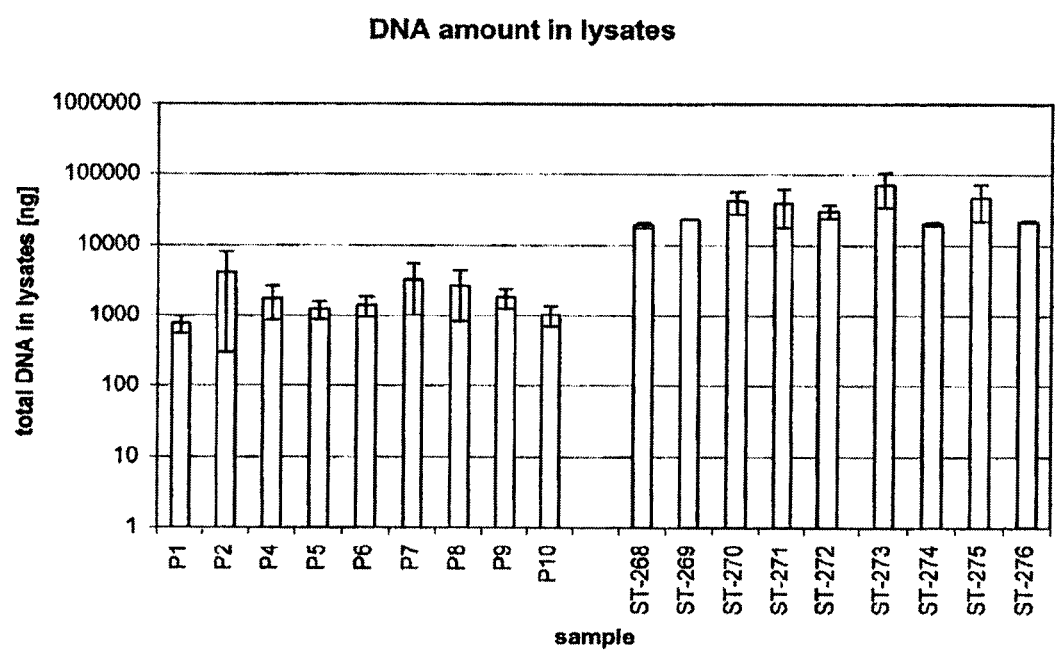
FIG. 8 shows, according to particular aspects, total DNA in lysates quantified according to example 10d (CFF1 assay; data scaled logarithmically). All data are means of four independently processed samples per specimen including standard deviation (Example 14).
Figure 9:
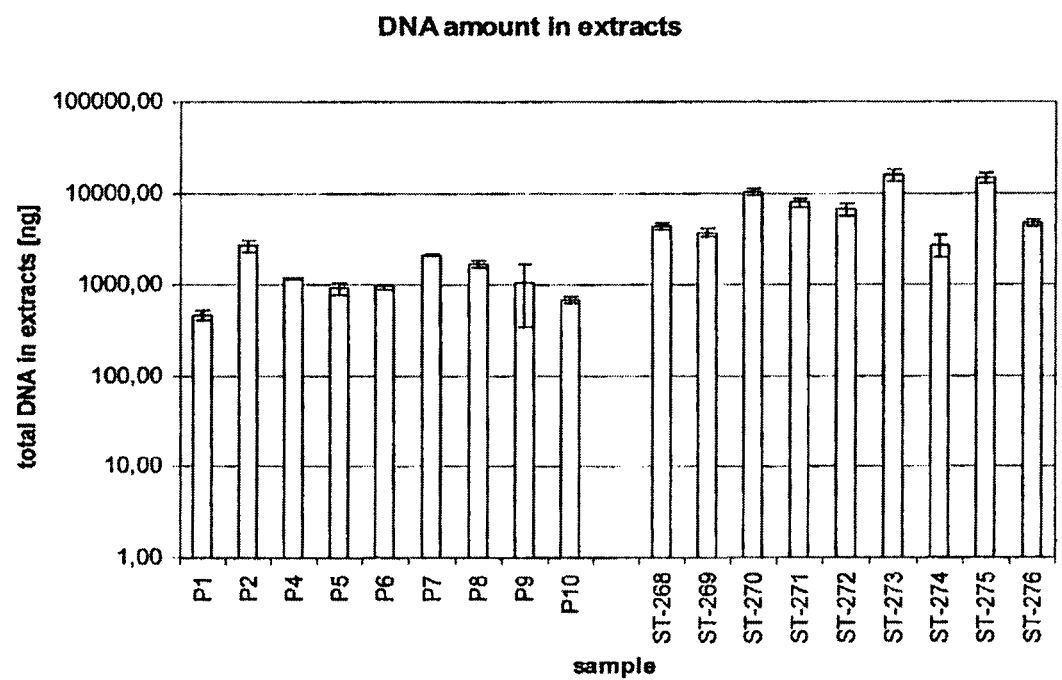
FIG. 9 shows, according to particular aspects, total DNA in extracts quantified according to example 10d (CFF1 assay; data scaled logarithmically). All data are means of four independently processed samples per specimen including standard deviation (example 14).
Figure 10:
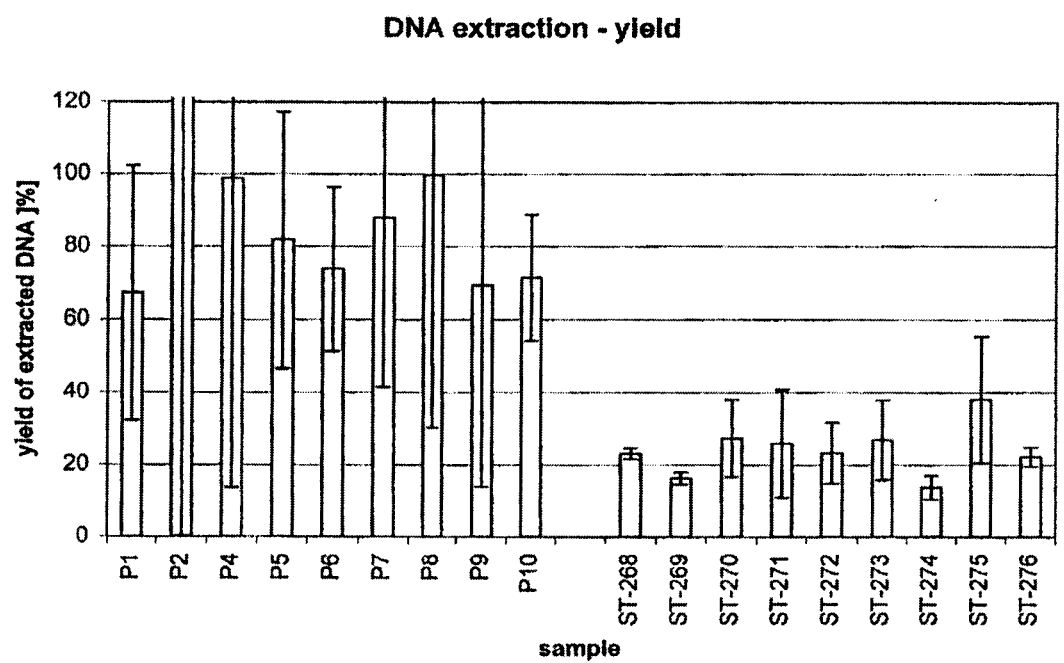
FIG. 10 shows, according to particular aspects, DNA yield after extraction (ratio of DNA in extract and DNA in lysate). All data are means of four independently processed samples per specimen including standard deviation (Example 14).
Figure 11:
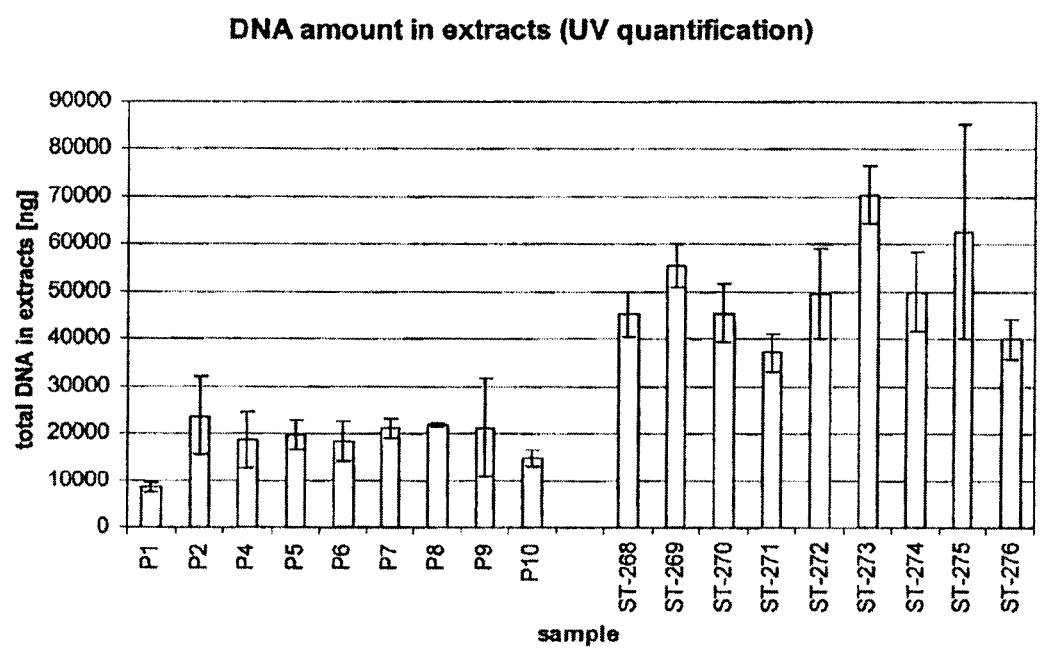
FIG. 11 shows, according to particular aspects, total amount of DNA physically present as determined by UV spectrophotometry (This DNA contains amplifiable as well as non-amplifiable DNA). All data are means of four independently processed samples per specimen including standard deviation (Example 14).
Figure 12:
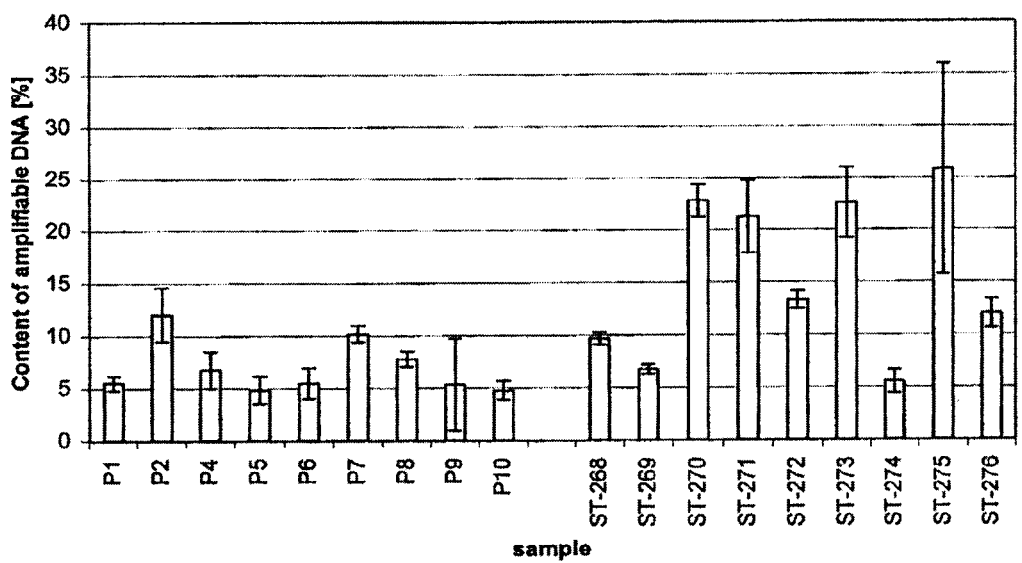
FIG. 12 shows, according to particular aspects, content of amplifiable DNA in extracts. The content is determined by the ratio of quantified DNA according to example 10d (CFF1 assay) and of quantified DNA according to example 10a (UV value from which the total amount of physically present DNA is calculated)]. All data are means of four independently processed samples per specimen including standard deviation (Example 14).
Figure 13:
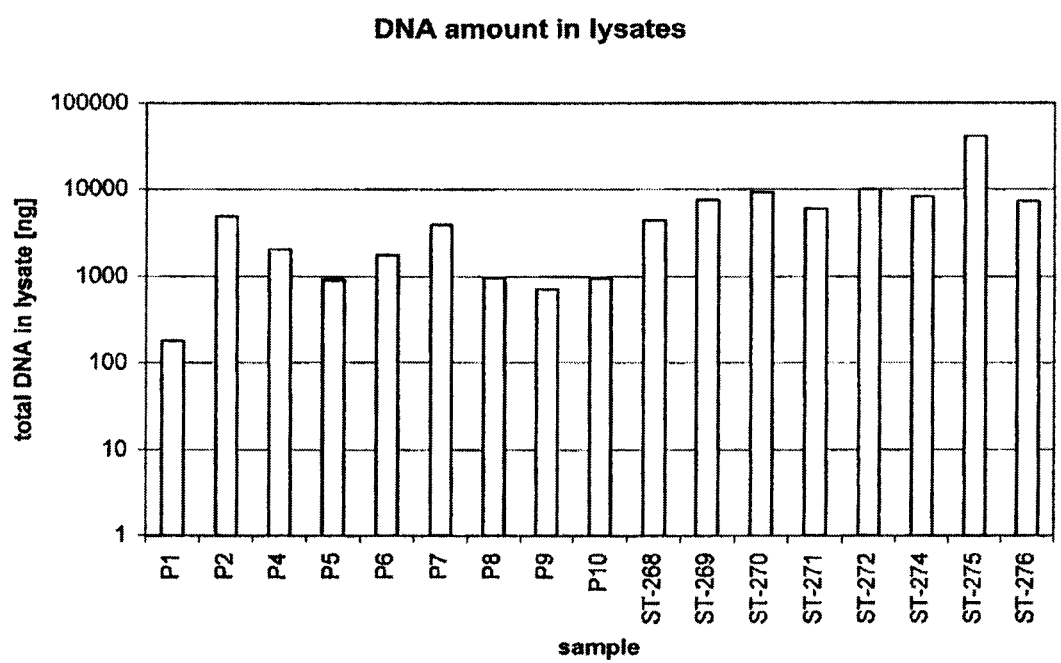
FIG. 13 shows, according to particular aspects, total DNA in lysates quantified according to example 10d (CFF1 assay; data scaled logarithmically) (Example 15).
Figure 14:
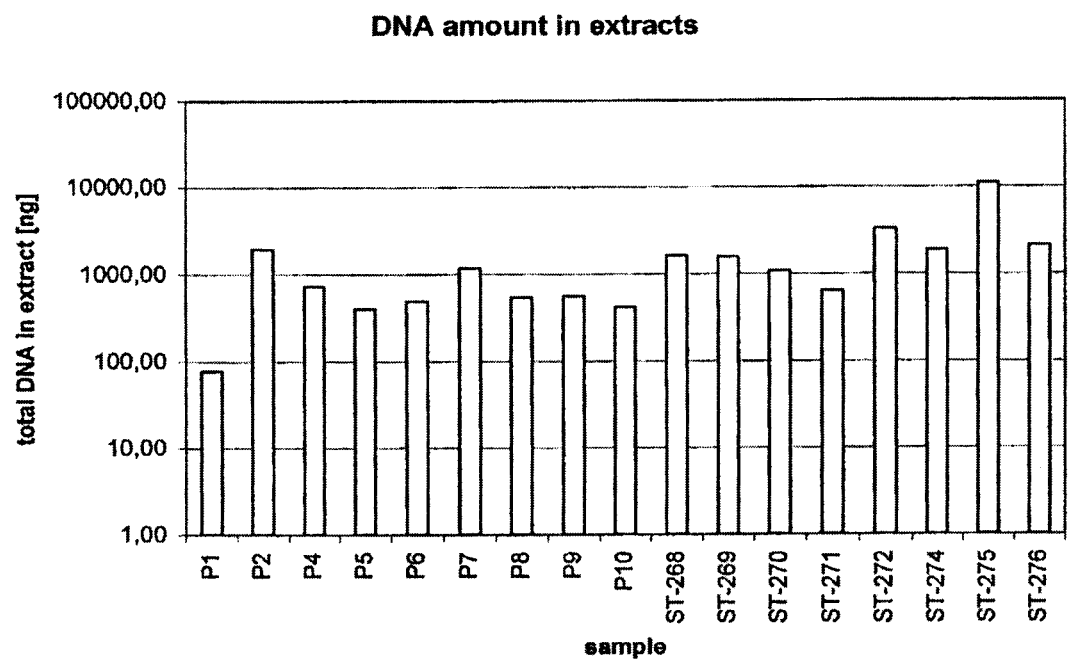
FIG. 14 shows, according to particular aspects, total DNA in extract quantified according to example 10d (CFF1 assay; data scaled logarithmically) (Example 15).
Figure 15:
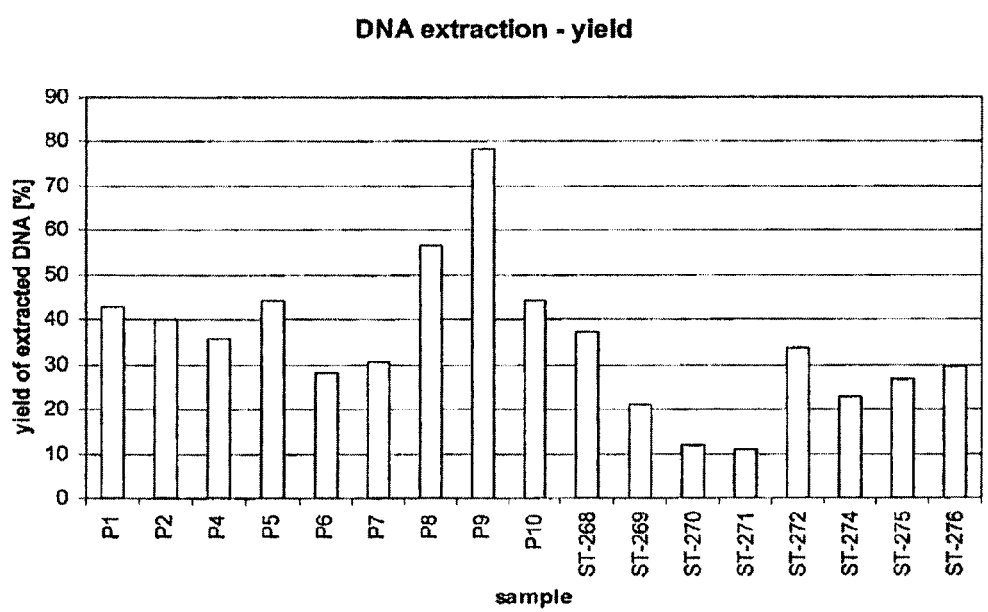
FIG. 15 shows, according to particular aspects, yield of DNA after extraction (ratio of DNA in extract and DNA in lysate) (Example 15).
Figure 16:
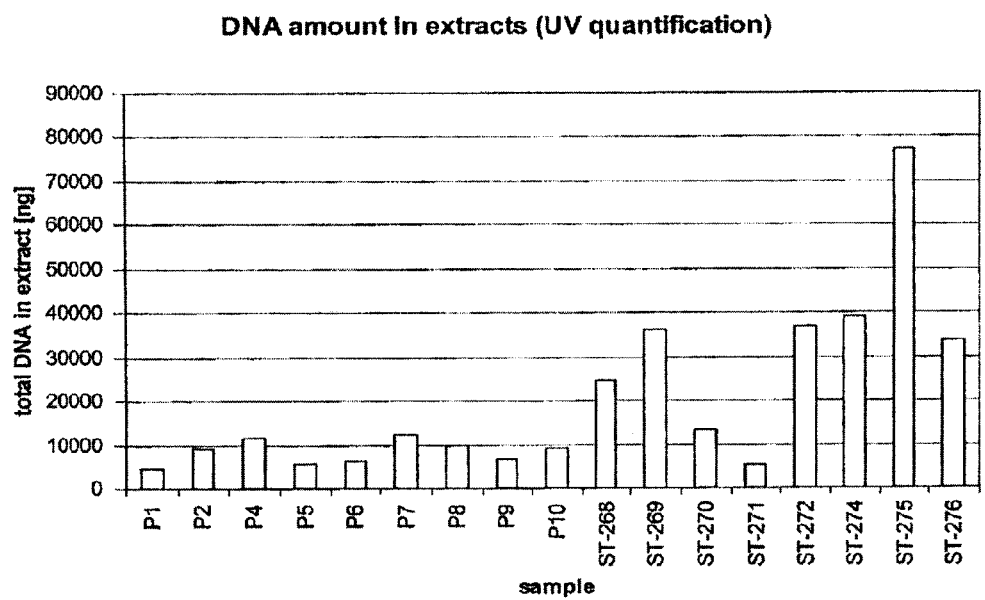
FIG. 16 shows, according to particular aspects, total amount of DNA physically present as determined by UV spectrophotometry (This DNA contains amplifiable as well as non-amplifiable DNA) (Example 15).
Figure 17:
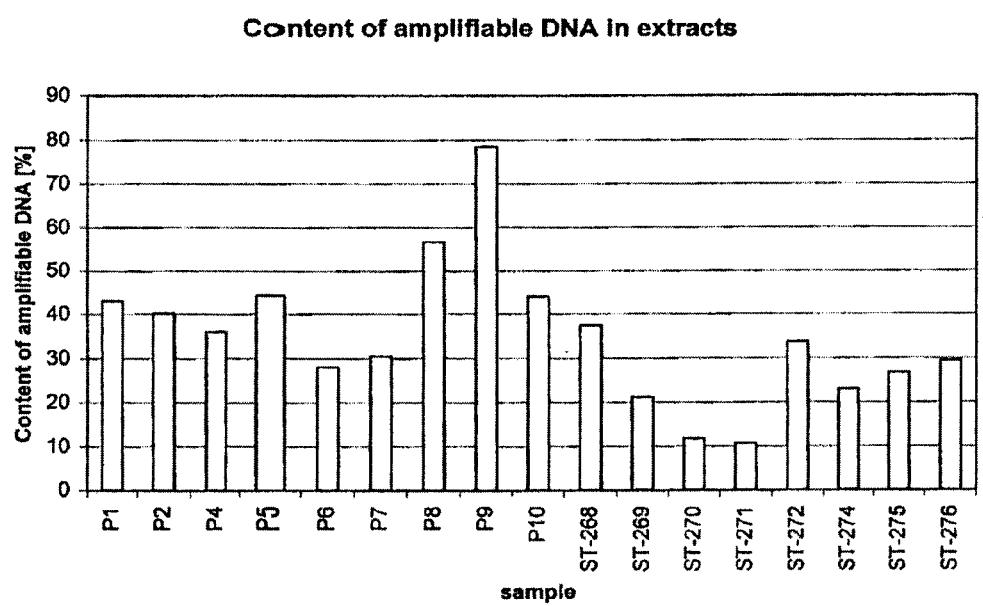
FIG. 17 shows, according to particular aspects, content of amplifiable DNA in extracts. The content is determined by the ratio of quantified DNA according to example 10d (CFF1 assay) and of quantified DNA according to example 10a (UV value from which the total amount of physically present DNA is calculated) (Example 15).

FIG. 7 shows the results of the PCR amplifications. The use of 1 U of Taq polymerase per reaction resulted in the successful amplification of amplicons up to 335 bp. To the contrary, it was possible to successfully amplify amplicons of up to 511 bp by means of 3 U Taq polymerase per reaction.

Example 14

Paraffin Removal, Lysis and DNA Extraction Plate Scale

Samples from 18 different paraffin-embedded formalin-fixed prostate specimens (P1, P2, P4, P5, P6, P7, P8, P9, P10, ST-268, ST-269, ST-270, ST-271, ST-272, ST-273, ST-274, ST-275, ST-276) were processed according to example 1a) (paraffin removal step), example 1b) (lysis step) and example 1c) (DNA extraction step). Four samples per specimen were processed independently. Each sample consisted of 3 sections (10 μm). The concentration of amplifiable DNA after lysis and DNA extraction was determined according to example 10d (CFF1 assay), respectively. The ratio of the quantified amplifiable DNA concentration after the DNA extraction step and of the quantified amplifiable DNA concentration after the lysis step reflects the yield of the extraction procedure. The total amount of DNA physically present in the extract was determined by UV spectrophotometry (example 10a). The content of amplifiable DNA in the extracts is reflected by the ratio of quantified amplifiable DNA according to example 10d and of the total amount of DNA determined by means of UV spectrophotometry (example 10a). Results are shown in Table 17b and FIGS. 8-12.

TABLE 17b

Processing of 18 paraffin-embedded formalin-fixed tissue specimens. Results of real time PCR based (example 10d) and UV spectrophotometry based (example 10a) quantification. All datas are means of four independently processed samples per specimen including standard deviation.

| sample | Total DNA in lysate - CFF1 assay [ng] | Standard deviation | Total DNA in extract - CFF1 assay [ng] | Standard deviation | Yield [%] | Standard deviation | Total DNA in extract - UV quantification [ng] | Standard deviation | Amplifiablility [%] | Standard deviation |
|---|---|---|---|---|---|---|---|---|---|---|
| P1 | 769.37 | 212.86 | 463.42 | 62.10 | 67.30 | 34.96 | 8490 | 1056.98 | 5.49 | 0.68 |
| P2 | 4108.87 | 3810.73 | 2697.79 | 406.28 | 185.17 | 184.96 | 23580 | 8277.25 | 12.02 | 2.59 |
| P4 | 1735.07 | 878.86 | 1181.97 | 23.15 | 98.68 | 84.95 | 18660 | 6092.29 | 6.76 | 1.75 |
| P5 | 1235.85 | 361.47 | 916.91 | 134.47 | 81.92 | 35.32 | 19560 | 3191.49 | 4.83 | 1.30 |
| P6 | 1389.80 | 438.28 | 951.95 | 71.40 | 73.78 | 22.61 | 18240 | 4313.88 | 5.46 | 1.45 |
| P7 | 3245.58 | 2235.31 | 2126.81 | 53.40 | 87.89 | 46.38 | 21090 | 1992.69 | 10.14 | 0.79 |
| P8 | 2620.08 | 1791.35 | 1687.70 | 144.38 | 99.66 | 69.38 | 21765 | 367.83 | 7.76 | 0.75 |
| P9 | 1808.96 | 549.44 | 1032.30 | 686.75 | 69.39 | 55.39 | 21240 | 10360.27 | 5.34 | 4.39 |
| P10 | 1031.69 | 326.70 | 696.47 | 62.02 | 71.48 | 17.29 | 14865 | 1818.16 | 4.76 | 0.90 |
| ST-268 | 18906.18 | 1697.40 | 4354.72 | 299.62 | 23.10 | 1.54 | 45195 | 4658.51 | 9.67 | 0.62 |
| ST-269 | 22888.11 | 201.42 | 3736.64 | 415.22 | 16.32 | 1.69 | 55545 | 4707.71 | 6.73 | 0.46 |
| ST-270 | 41912.14 | 14525.27 | 10316.21 | 828.41 | 27.36 | 10.65 | 45495 | 6065.72 | 22.82 | 1.56 |
| ST-271 | 39288.96 | 21812.73 | 7842.60 | 975.43 | 25.91 | 14.93 | 37185 | 4089.22 | 21.28 | 3.53 |
| ST-272 | 30026.72 | 6636.77 | 6578.06 | 1035.90 | 23.29 | 8.43 | 49725 | 9499.14 | 13.31 | 0.86 |
| ST-273 | 69900.08 | 36062.28 | 15876.32 | 2394.68 | 26.92 | 11.00 | 70470 | 6251.05 | 22.60 | 3.40 |
| ST-274 | 19929.85 | 1098.59 | 2758.56 | 754.86 | 13.78 | 3.27 | 50085 | 8262.94 | 5.52 | 1.11 |
| ST-275 | 46583.92 | 25018.63 | 14482.29 | 1766.26 | 38.00 | 17.48 | 62640 | 22706.76 | 25.80 | 10.11 |
| ST-276 | 21562.06 | 701.41 | 4785.23 | 430.75 | 22.25 | 2.65 | 40200 | 4213.41 | 11.98 | 1.40 |

Example 15

Paraffin Removal, Lysis and DNA Extraction Tube Scale

Sections from 17 different paraffin-embedded formalin-fixed prostate specimens (P1, P2, P4, P5, P6, P7, P8, P9, P10, ST-268, ST-269, ST-270, ST-271, ST-272, ST-274, ST-275, ST-276) were processed according to example 1a) (paraffin removal step), example 1b) (lysis step) and example 2c) (DNA extraction with QIAGEN® DNEASY® tissue kit). Each sample consisted of 3 sections (10 μm). The concentration of amplifiable DNA after lysis and DNA extraction was determined according to example 10d (CFF1 assay), respectively. The ratio of the quantified amplifiable DNA concentration after the DNA extraction step and of the quantified amplifiable DNA concentration after the lysis step reflects the yield of the extraction procedure. The total amount of DNA physically present in the extract was determined by UV spectrophotometry (example 10a). The content of amplifiable DNA in the extracts is reflected by the ratio of quantified DNA according to example 10d and of the total amount of DNA determined by means of UV spectrophotometry (example 10a). Results are shown in Table 18 and FIGS. 13-17.

TABLE 18

Processing of 17 paraffin-embedded formalin-fixed tissue specimens. Results of real time PCR based (example 10d) and UV spectrophotometry based (example 10a) quantification.

| sample | Total DNA in lysate - CFF1 assay [ng] | Total DNA in extract - CFF1 assay [ng] | Yield [%] | Total DNA in extract - UV quantification [ng] | Content of amplifiable DNA [%] |
|---|---|---|---|---|---|
| P1 | 179.73 | 77.29 | 43.00 | 4704 | 1.64 |
| P2 | 4884.12 | 1961.33 | 40.16 | 9240 | 21.23 |
| P4 | 2036.82 | 732.73 | 35.97 | 11460 | 6.39 |
| P5 | 903.14 | 400.61 | 44.36 | 5520 | 7.26 |
| P6 | 1750.69 | 491.23 | 28.06 | 6480 | 7.58 |
| P7 | 3863.33 | 1176.92 | 30.46 | 12240 | 9.62 |
| P8 | 957.18 | 542.60 | 56.69 | 9900 | 5.48 |
| P9 | 715.74 | 561.57 | 78.46 | 6540 | 8.59 |
| P10 | 946.06 | 417.50 | 44.13 | 9240 | 4.52 |
| ST-268 | 4383.18 | 1639.30 | 37.40 | 24720 | 6.63 |
| ST-269 | 7497.87 | 1593.21 | 21.25 | 36180 | 4.40 |
| ST-270 | 9151.79 | 1081.93 | 11.82 | 13260 | 8.16 |
| ST-271 | 5954.34 | 641.61 | 10.78 | 5148 | 12.46 |
| ST-272 | 9897.51 | 3335.76 | 33.70 | 36960 | 9.03 |
| ST-274 | 8230.91 | 1894.26 | 23.01 | 39180 | 4.83 |
| ST-275 | 41461.29 | 11122.82 | 26.83 | 77400 | 14.37 |
| ST-276 | 7272.27 | 2139.90 | 29.43 | 33600 | 6.37 |

Example 16

Figure 18:
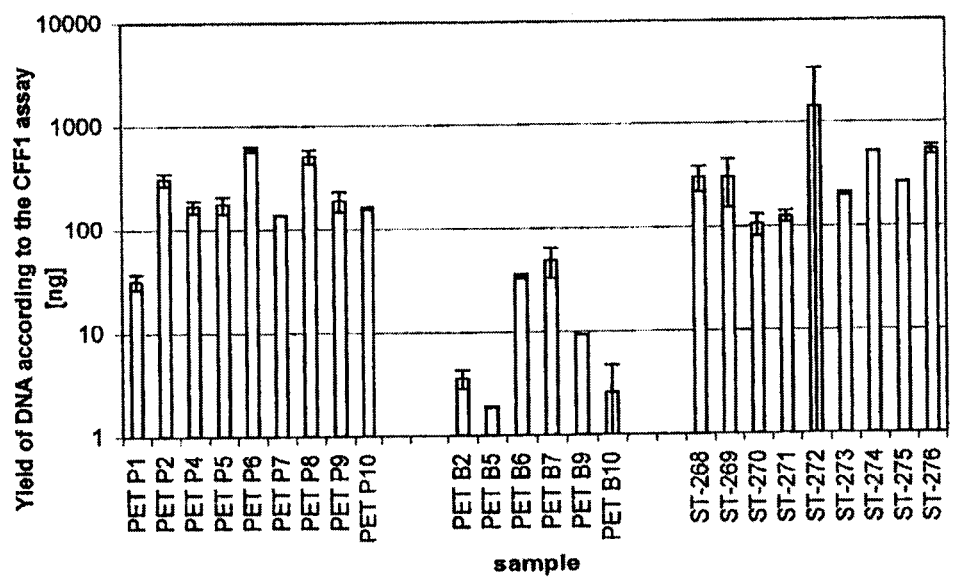
FIG. 18 shows, according to particular aspects, total yield of DNA after bisulfite treatment and subsequent purification. The quantification was carried out according to example 10d (CFF1 assay; data scaled logarithmically). All data are means of two independently processed samples per specimen.
Figure 19:
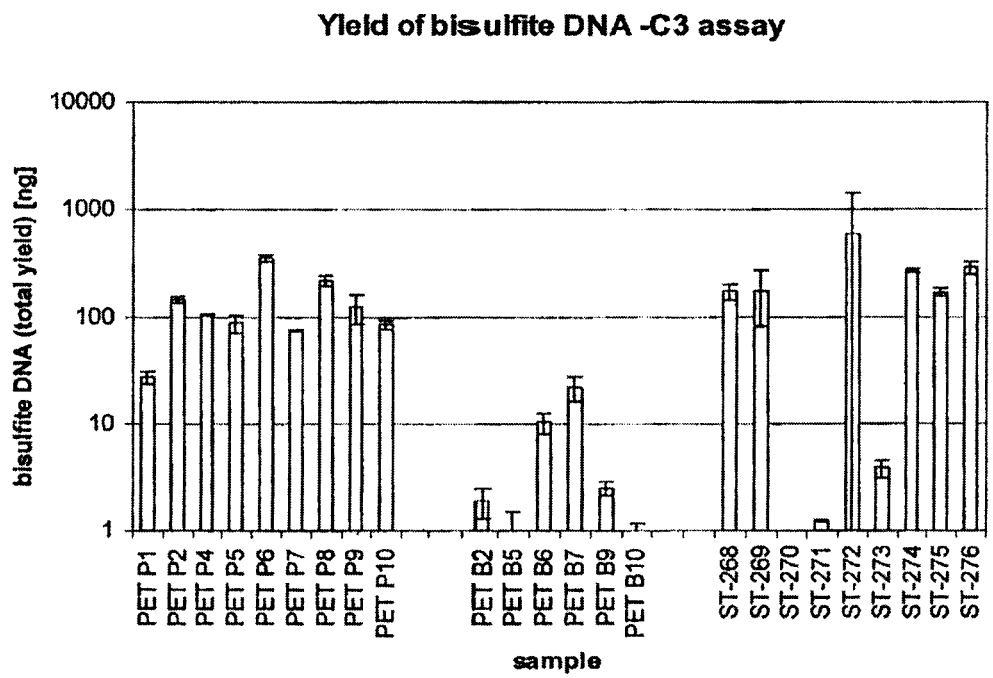
FIG. 19 shows, according to particular aspects, total yield of DNA after bisulfite treatment and subsequent purification. The quantification was carried out according to example 10c (C3 assay; data scaled logarithmically). All data are means of two independently processed samples per specimen (Example 16).

Processing According to Example 2 of 24 Paraffin-Embedded Formalin-Fixed Samples Derived from Prostate or Breast Tissue, Tube Scale 24 paraffin-embedded formalin-fixed tissue specimens (prostate: PET P1-P10 and ST-268-ST-276 and breast: PET B2-B10) were processed according to example 2. Two samples per specimen were processed resulting in 48 samples in total. Each sample consisted of 3 sections (each 10 μm) provided in 1.5 ml tubes. The DNA after bisulfite treatment and subsequent purification was characterized according to example 10d (CFF1 assay; determination of the amount of DNA converted by bisulfite treatment and of the amount of DNA not converted by the bisulfite treatment and therefore represents genomic DNA) and according to example 10c (C3 assay; determination of only DNA converted by bisulfite treatment). Results of these quantifications are shown in Table 19, in FIG. 18 and in FIG. 19, respectively.

TABLE 19

Processing of 24 paraffin-embedded formalin-fixed tissue specimens. Results of C3 and CFF1 assay quantification (example 10c and 10d, respectively) and the ratio thereof. All data are means of two independently processed samples per specimen (example 16).

| Sample | Yield of DNA - CFF1 assay | Standard deviation | Yield of DNA - C3 assay | Standard deviation |
|---|---|---|---|---|
| PET P1 | 31.51 | 5.35 | 26.85 | 3.73 |
| PET P2 | 307.22 | 42.33 | 143.93 | 9.34 |
| PET P4 | 167.69 | 23.03 | 103.21 | 2.18 |
| PET P5 | 176.06 | 33.61 | 86.27 | 17.43 |
| PET P6 | 598.59 | 37.35 | 358.71 | 28.01 |
| PET P7 | 137.10 | 1.56 | 74.49 | 1.40 |
| PET P8 | 511.88 | 79.05 | 219.63 | 25.52 |
| PET P9 | 189.48 | 42.02 | 121.15 | 36.88 |
| PET P10 | 158.89 | 4.36 | 83.30 | 8.25 |
| PET B2 | 3.57 | 0.76 | 1.86 | 0.58 |
| PET B5 | 1.88 | 0.03 | 0.83 | 0.67 |
| PET B6 | 34.20 | 1.56 | 10.17 | 2.18 |
| PET B7 | 48.11 | 15.50 | 21.81 | 5.51 |
| PET B9 | 9.34 | 0.05 | 2.51 | 0.40 |
| PET B10 | 2.57 | 2.18 | 0.56 | 0.61 |
| ST-268 | 301.94 | 83.41 | 171.65 | 26.14 |
| ST-269 | 304.14 | 151.26 | 173.86 | 93.37 |
| ST-270 | 106.51 | 25.52 | 0.29 | 0.21 |
| ST-271 | 125.88 | 16.18 | 1.23 | 0.03 |
| ST-272 | 1422.66 | 1959.30 | 597.51 | 841.84 |
| ST-273 | 205.11 | 6.22 | 3.83 | 0.75 |
| ST-274 | 521.57 | 3.11 | 271.13 | 13.07 |
| ST-275 | 264.96 | 1.24 | 169.23 | 16.50 |
| ST-276 | 547.98 | 59.13 | 289.39 | 38.90 |

Example 17

Figure 20:
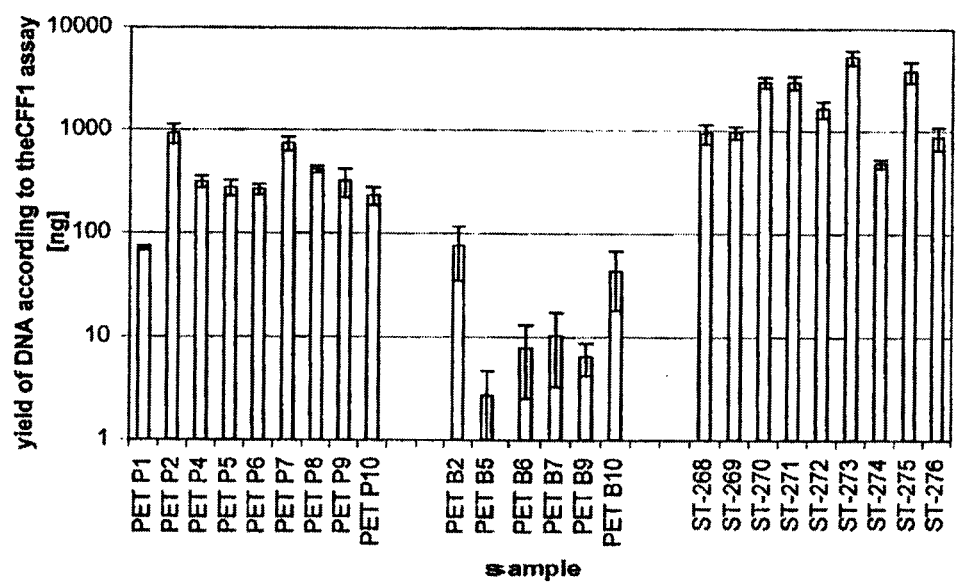
FIG. 20 shows, according to particular aspects, total yield of DNA after bisulfite treatment and subsequent purification. The quantification was carried out according to example 10d (CFF1 assay; data scaled logarithmically). All data are means of four independently processed samples per specimen (Example 17).
Figure 21:
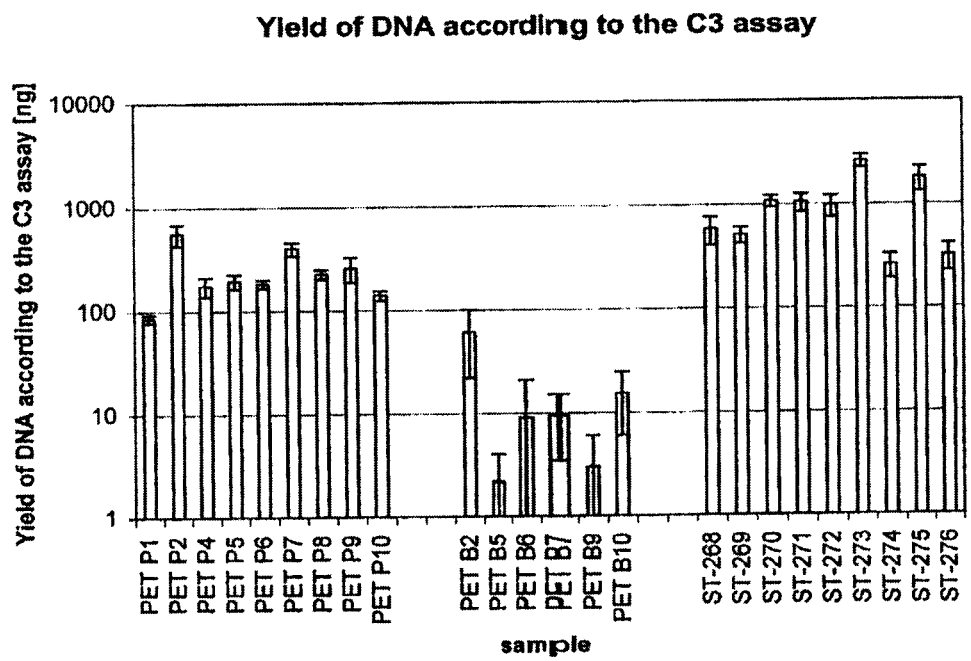
FIG. 21 shows, according to particular aspects, total yield of DNA after bisulfite treatment and subsequent purification. The quantification was carried out according to example 10c (C3 assay; data scaled logarithmically). All data are means of four independently processed samples per specimen (Example 17).

Processing of 24 Paraffin-Embedded Formalin-Fixed Samples Derived from Prostate or Breast Tissue, Plate Scale 24 paraffin-embedded formalin-fixed tissue specimens (prostate: PET P1-P10 and ST-268-ST-276] and breast: PET B2-B10) were processed according to example 1. Four samples per specimen were processed resulting in 96 samples in total. Each sample consisted of 3 sections (10 µm each) provided in 1.5 ml tubes. The resulting bisulfite treated and purified DNA was characterized according to example 10d (CFF1 assay; determination of the amount of DNA converted by bisulfite treatment and of the amount of DNA not converted by the bisulfite treatment and therefore represents genomic DNA) and according to example 10c (C3 assay; determination of only DNA converted by bisulfite treatment). Results of these quantifications are shown in Table 20, FIG. 20 and FIG. 21, respectively.

TABLE 20

Processing of 24 paraffin-embedded formalin-fixed tissue specimens. Results of C3 and CFF1 assay quantification (example 10c and 10d, respectively) and the ratio thereof. All data are means of four independently processed samples per specimen.

| Sample | Yield of DNA - CFF1 assay | Standard deviation | Yield of DNA - C3 assay | Standard deviation |
|---|---|---|---|---|
| PET P1 | 71.03 | 3.65 | 85.42 | 7.50 |
| PET P2 | 920.67 | 203.57 | 556.83 | 129.87 |
| PET P4 | 311.33 | 41.97 | 173.67 | 36.73 |
| PET P5 | 273.67 | 46.65 | 194.33 | 30.60 |
| PET P6 | 263.33 | 31.26 | 181.50 | 17.29 |
| PET P7 | 736.67 | 116.22 | 398.50 | 60.04 |
| PET P8 | 411.00 | 29.14 | 225.83 | 23.96 |
| PET P9 | 319.83 | 98.97 | 256.75 | 70.86 |
| PET P10 | 230.00 | 44.73 | 139.50 | 15.17 |
| PET B2 | 75.53 | 40.85 | 61.69 | 39.48 |
| PET B5 | 2.72 | 1.99 | 2.19 | 1.87 |
| PET B6 | 7.79 | 5.25 | 9.07 | 12.10 |
| PET B7 | 10.27 | 6.96 | 9.40 | 5.90 |
| PET B9 | 6.47 | 2.25 | 3.02 | 3.07 |
| PET B10 | 42.92 | 24.85 | 15.53 | 9.48 |
| ST-268 | 948.00 | 206.25 | 585.83 | 175.80 |
| ST-269 | 969.00 | 135.27 | 515.83 | 92.15 |
| ST-270 | 2973.33 | 363.52 | 1075.83 | 134.40 |
| ST-271 | 2983.33 | 441.33 | 1054.17 | 207.50 |
| ST-272 | 1641.67 | 307.50 | 980.83 | 227.73 |
| ST-273 | 5263.33 | 848.62 | 2598.33 | 357.87 |
| ST-274 | 479.67 | 47.60 | 259.58 | 70.33 |
| ST-275 | 3856.67 | 896.37 | 1794.17 | 470.42 |
| ST-276 | 871.67 | 220.93 | 320.08 | 94.72 |

Example 18

Processing of Samples Derived from 150 Paraffin-Embedded Formalin-Fixed Breast Cancer Specimens Samples of 150 paraffin-embedded formalin-fixed breast cancer specimens (E001-E150) were processed according to example 9. Each sample consisted of 3 sections (10 µm each) which were provided in 1.5 ml tubes. Yield of genomic DNA after extraction was determined using UV spectrophotometry (example 10a) and the CFF1 assay (example 10d). The yield of bisulfite converted DNA after bisulfite treatment and subsequent purification was determined using the C3 assay (example 10c).

TABLE 21

Yields of bisulfite converted and non-bisulfite converted DNA derived from paraffin-embedded formalin-fixed breast cancer specimens. DNA was quantified according to example 10d (CFF1 assay), according to example 10c (C3 assay) and according to example 10a (UV spectrophotometry).

| Sample | Genomic DNA [ng] total in 70 ul extract (based on UV determination; example 10a) | Genomic DNA [ng] total in 70 ul extract (based CFF1 assay; example 10d) | total yield [ng] of bisulfite converted DNA in 50 µl eluate after purification (based on the C3 assay; example 10c) |
|---|---|---|---|
| E001 | 13545.0 | 1812.0 | 1760.6 |
| E002 | 6125.0 | 688.6 | 215.8 |
| E003 | 5760.0 | 348.9 | 140.0 |
| E004 | 20160.0 | 338.6 | 174.5 |
| E005 | 6852.6 | 1017.9 | 514.2 |
| E006 | 26460.0 | 11173.0 | 1541.6 |
| E007 | 16905.0 | 8213.1 | 2410.4 |

TABLE 21-continued

Yields of bisulfite converted and non-bisulfite converted DNA derived from paraffin-embedded formalin-fixed breast cancer specimens. DNA was quantified according to example 10d (CFF1 assay), according to example 10c (C3 assay) and according to example 10a (UV spectrophotometry).

| Sample | Genomic DNA [ng] total in 70 ul extract (based on UV determination; example 10a) | Genomic DNA [ng] total in 70 ul extract (based CFF1 assay; example 10d) | total yield [ng] of bisulfite converted DNA in 50 μl eluate after purification (based on the C3 assay; example 10c) |
|---|---|---|---|
| E008 | 16012.5 | 9725.2 | 4452.0 |
| E009 | 15866.7 | 8657.4 | 1749.4 |
| E010 | 27195.0 | 14169.6 | 200.6 |
| E011 | 7680.0 | 4115.0 | 1009.2 |
| E012 | 16380.0 | 2102.2 | 1032.4 |
| E013 | 1866.7 | 1962.8 | 1374.3 |
| E014 | 15225.0 | 2430.8 | 1028.0 |
| E015 | 13835.3 | 1779.8 | 857.2 |
| E016 | 17684.2 | 1866.5 | 894.2 |
| E017 | 10350.0 | 1240.1 | 240.1 |
| E018 | 8085.0 | 1326.0 | 873.7 |
| E019 | 16357.9 | 3256.2 | 1341.4 |
| E020 | 21123.5 | 3401.2 | 1785.1 |
| E021 | 10278.9 | 1395.2 | 1201.2 |
| E022 | 20432.4 | 4540.2 | 2970.8 |
| E023 | 22976.5 | 2506.7 | 1651.6 |
| E024 | 5250.0 | 1691.7 | 1027.4 |
| E025 | 24465.0 | 4408.7 | 2358.7 |
| E026 | 17170.6 | 8749.5 | 3195.7 |
| E027 | 17616.7 | 2819.4 | 1327.1 |
| E028 | 4817.6 | 11498.9 | 4516.8 |
| E029 | 30333.3 | 4922.3 | 2185.2 |
| E030 | 16305.9 | 16442.2 | 6160.9 |
| E031 | 7455.0 | 3703.1 | 1278.7 |
| E032 | 10005.9 | 4757.4 | 2073.8 |
| E033 | 9173.7 | 4922.1 | 1628.7 |
| E034 | 8715.0 | 4010.9 | 1686.4 |
| E035 | 10994.1 | 6841.9 | 1496.6 |
| E036 | 10500.0 | 4358.7 | 2828.2 |
| E037 | 20650.0 | 5711.1 | 4439.0 |
| E038 | 30333.3 | 3311.1 | 2801.3 |
| E039 | 9240.0 | 2956.5 | 2325.2 |
| E040 | 6930.0 | 2261.9 | 981.5 |
| E041 | 8505.0 | 446.5 | 387.1 |
| E042 | 4550.0 | 789.6 | 669.6 |
| E043 | 3315.8 | 779.7 | 425.8 |
| E044 | 4095.0 | 845.1 | 489.5 |
| E045 | 4089.5 | 795.8 | 531.4 |
| E046 | 6052.9 | 107.2 | 164.8 |
| E047 | 11200.0 | 200.1 | 113.4 |
| E048 | 5682.4 | 149.7 | 248.8 |
| E049 | 3990.0 | 76.3 | 35.9 |
| E050 | 4531.6 | 235.4 | 85.7 |
| E051 | 13042.1 | 6107.0 | 2887.2 |
| E052 | 8295.0 | 3162.3 | 1063.5 |
| E053 | 11235.0 | 4412.9 | 3815.7 |
| E054 | 8866.7 | 3196.3 | 2329.3 |
| E055 | 7245.0 | 2458.7 | 1452.5 |
| E056 | 14595.0 | 3257.7 | 5484.6 |
| E057 | 11970.0 | 3005.9 | 2533.5 |
| E058 | 17047.1 | 3892.1 | 2368.3 |
| E059 | 13094.1 | 6094.4 | 4047.3 |
| E060 | 35870.3 | 2849.6 | 3108.8 |
| E061 | 22750.0 | 715.8 | 440.5 |
| E062 | 13920.0 | 840.0 | 340.1 |
| E063 | 14452.9 | 3292.1 | 3313.1 |
| E064 | 4095.0 | 761.4 | 510.1 |
| E065 | 3705.9 | 2855.2 | 3153.8 |
| E066 | 2625.0 | 244.7 | 11.2 |
| E067 | 3383.3 | 417.2 | 362.6 |
| E068 | 3088.2 | 718.6 | 321.9 |
| E069 | 2216.7 | 118.0 | 17.3 |
| E070 | 11520.0 | 214.8 | 71.5 |
| E071 | 10623.5 | 1463.9 | 1361.2 |
| E072 | 26950.0 | 2064.7 | 2121.6 |
| E073 | 12723.5 | 2277.5 | 2169.1 |
| E074 | 2333.3 | 3841.5 | 3249.4 |
| E075 | 11488.2 | 1545.8 | 1235.2 |
| E076 | 31360.0 | 14426.1 | 5108.5 |
| E077 | 18060.0 | 8039.9 | 3387.0 |
| E078 | 23415.0 | 14134.2 | 6859.3 |
| E079 | 14000.0 | 10264.3 | 5371.6 |
| E080 | 21735.0 | 9167.2 | 2812.9 |
| E081 | 6883.3 | 31543.5 | 25884.0 |
| E082 | 23730.0 | 12237.9 | 7183.1 |
| E083 | 17541.2 | 7782.0 | 4135.6 |
| E084 | 30836.8 | 19137.9 | 12754.5 |
| E085 | 21466.7 | 13501.5 | 5589.2 |
| E086 | 16026.3 | 3724.7 | 2177.5 |
| E087 | 9173.7 | 1701.5 | 1091.9 |
| E088 | 27176.5 | 3309.1 | 1072.5 |
| E089 | 19950.0 | 3831.9 | 1739.0 |
| E090 | 23566.7 | 3985.7 | 3139.2 |
| E091 | 2594.1 | 5222.6 | 5906.1 |
| E092 | 19600.0 | 2055.6 | 1131.1 |
| E093 | 10500.0 | 2585.4 | 1223.6 |
| E094 | 15093.8 | 4220.0 | 300.6 |
| E095 | 9555.0 | 1630.1 | 840.0 |
| E096 | 14700.0 | 2675.9 | 1076.2 |
| E097 | 21525.0 | 4163.3 | 1840.9 |
| E098 | 13416.7 | 4691.0 | 883.6 |
| E099 | 13230.0 | 2024.5 | 1765.6 |
| E100 | 12250.0 | 1903.4 | 852.3 |
| E101 | 4725.0 | 4695.8 | 1007.1 |
| E102 | 14910.0 | 6633.8 | 2066.2 |
| E103 | 19841.4 | 10410.8 | 3738.5 |
| E104 | 22283.3 | 10963.4 | 4059.1 |
| E105 | 31994.1 | 15319.9 | 3397.5 |
| E106 | 6930.0 | 968.2 | 511.4 |
| E107 | 5526.3 | 616.5 | 261.6 |
| E108 | 5968.4 | 875.8 | 175.0 |
| E109 | 5906.3 | 753.1 | 234.5 |
| E110 | 4830.0 | 782.8 | 594.2 |
| E111 | 2625.0 | 4344.9 | 2081.4 |
| E112 | 14880.0 | 4266.1 | 2366.6 |
| E113 | 6090.0 | 2727.2 | 1636.4 |
| E114 | 10710.0 | 4280.6 | 2824.6 |
| E115 | 7665.0 | 3166.8 | 3354.9 |
| E116 | 6176.5 | 342.0 | 64.5 |
| E117 | 2216.7 | 385.3 | 146.0 |
| E118 | 50770.6 | 486.5 | 104.3 |
| E119 | 4935.0 | 439.2 | 406.8 |
| E120 | 10266.7 | 929.9 | 516.2 |
| E121 | 8925.0 | 2893.5 | 259.9 |
| E122 | 13533.3 | 7499.9 | 3242.3 |
| E123 | 49411.8 | 16014.1 | 8003.4 |
| E124 | 19010.5 | 6660.4 | 4336.0 |
| E125 | 10383.3 | 2631.8 | 1100.9 |
| E126 | 23231.3 | 8386.5 | 3450.2 |
| E127 | 8820.0 | 2078.4 | 2172.0 |
| E128 | 2730.0 | 676.6 | 166.4 |
| E129 | 32160.0 | 1465.8 | 606.5 |
| E130 | 4083.3 | Undetermined | 1068.5 |
| E131 | 3045.0 | 396.5 | 181.0 |
| E132 | 3780.0 | 507.3 | 515.9 |
| E133 | 7669.6 | 526.0 | 570.5 |
| E134 | 6650.0 | 896.0 | 561.3 |
| E135 | 6052.9 | 903.1 | 314.5 |
| E136 | 22260.0 | 6770.9 | 2886.7 |
| E137 | 19600.0 | 4402.2 | 1359.9 |
| E138 | 8400.0 | 10852.0 | 4979.4 |
| E139 | 19635.0 | 6613.7 | 4495.2 |

TABLE 21-continued

Yields of bisulfite converted and non-bisulfite converted DNA derived from paraffin-embedded formalin-fixed breast cancer specimens. DNA was quantified according to example 10d (CFF1 assay), according to example 10c (C3 assay) and according to example 10a (UV spectrophotometry).

| Sample | Genomic DNA [ng] total in 70 ul extract (based on UV determination; example 10a) | Genomic DNA [ng] total in 70 ul extract (based CFF1 assay; example 10d) | total yield [ng] of bisulfite converted DNA in 50 μl eluate after purification (based on the C3 assay; example 10c) |
|---|---|---|---|
| E140 | 27650.0 | 9160.8 | 6587.8 |
| E141 | 26194.7 | 8656.0 | 4678.9 |
| E142 | 4550.0 | 10660.7 | 3116.2 |
| E143 | 26600.0 | 9404.2 | 2983.5 |
| E144 | 33705.0 | 12358.5 | 4073.3 |
| E145 | 10252.9 | 5114.6 | 2774.1 |
| E146 | 31850.0 | 19365.9 | 5729.1 |
| E147 | 24780.0 | 11532.6 | 6048.3 |
| E148 | 21000.0 | 11540.2 | 4106.7 |
| E149 | 2400.0 | 13681.8 | 6231.2 |
| E150 | 29750.0 | 18923.4 | 3814.9 |

Example 19

Processing of Laser Capture Microdissected Cells

Laser capture microdissected cells from a paraffin-embedded formalin-fixed breast cancer specimen was bisulfite treated.

a) Microdissection

The 10 μm section which was mounted on a microscopic slide was subjected to a methylene blue staining procedure and subsequently laser capture microdissected. Microdissection was carried out using a Microbeam instrument (P.A.L.M.® Microlaser Technologies AG, Bernried, Germany). Two areas of the section (each comprising approximately 0.25 mm$^2$) were microdissected and collected in two 200 μl tubes with adhesive caps (Adhesive Caps 200, P.A.L.M.® Microlaser Technologies AG, Bernried, Germany). Because of the microdissection no removal of paraffin is necessary.

b) Lysis Step

Sample material sticked to the adhesive caps after microdissection and was subjected to a lysis step. Therefore 20 μl lysis buffer (50 mmol/l Tris-HCl, pH 8.0, 1 mmol/l EDTA, 0.5 v/v % Tween, 10 ng/μl poly-dA, 3 mg/ml proteinase K) were carefully added to the caps. Four control reactions were performed: two negative controls with tubes containing no sample but lysis buffer and two positive controls with tubes containing lysis buffer and 500 pg human genomic DNA (Promega, USA) Tubes were closed carefully avoiding a loosening of the drop from the cap. The tubes were incubated 12 h at 60° C. in a MASTERCYCLER® PCR machine (EPPENDORF®, Germany). Since the sample material was located at the caps the lid of the MASTERCYCLER® was also set to 60° C. After incubation samples were centrifuged in a table centrifuge for 30 s to transfer the lysed sample to the bottom of the tube.

c) Bisulfite Treatment

After this, samples were subjected to bisulfite treatment as follows. To dissolve any DNA which might remain at the cap, 19 μl bisulfite solution (470.8 g/l sodium disulfite [Merck] and 112.8 g/l sodium sulfite [Fluka]) were added to the cap, tubes were carefully closed and incubated for 5 min at room temperature. Samples were now centrifuged for 30 s using a table centrifuge. The last step (adding bisulfite solution to the cap, incubating and centrifuging) was repeated once. 6 μl DME solution were added to each sample, the DME solution comprising a radical scavenger (125.3 g/l 6-hydroxy-2,5,7,8-tetramethyl-chroman-2-carboxylic acid) in DME (diethylene-glycoldimethylether Merck]). The samples were incubated under the following conditions: 5 min 99° C., 22 min 60° C., 3 min 99° C., 97 min 60° C., 3 min 99° C. and 177 min 60° C. Incubation was carried out using a MASTERCYCLER® (EPPENDORF®).

d) DNA Purification

DNA purification after bisulfite treatment was carried out by means of ZYMO-SPIN™ IC columns (Zymo Research, USA). 166 μl AVL buffer (QIAGEN®, Germany) were added to the ZYMO-SPIN™ IC columns. Bisulfite reaction mix (64 μl total per sample) was added to the columns. The used pipett tips were placed in the respective bisulfite reaction tubes for further usage in order to avoid DNA loss due to drops sticking at the tips. 90 μl of AVL buffer were added to the empty bisulfite reaction tubes and afterwards transferred to the ZYMO-SPIN™ IC columns using the respective pipett tips which were previously placed in the respective tubes. Bisulfite reaction mix and buffer AVL were mixed in the columns by pipetting up and down several times and incubated 10 min at room temperature. 250 μl ethanol were added to the columns and mixed with the pipett. Again, the same pipett was used for mixing in order to avoid DNA loss due to drops sticking at the tips as already explained above. Columns were centrifuged 1 min at 16,000×g. Columns were transferred to a new 2 ml collection tube and 500 μl desulfonation buffer (0.2 mol/l NaOH, 90% v/v ethanol) was added to each column. Columns were centrifuged 1 min at 16,000×g. Columns were transferred to a new 2 ml collection tube and 500 μl buffer AW1 (QIAGEN®, Germay) was added to each column. Columns were centrifuged 1 min at 16,000×g. Columns were transferred to a new 2 ml collection tube and 500 μl buffer AW2 (QIAGEN®, Germay) was added to each column. Columns were centrifuged 3 min at 16,000×g. Columns were placed in a 1.5 ml collection tube for DNA elution. DNA was eluted by adding 12.5 μl water (prewarmed to 50° C.) to the columns, incubating 1 min and centrifuging 1 min at 6,000×g. The elution step was repeated resulting in approximately 20 μl eluate total (5 μl loss due to columns geometry and evaporation).

e) Subsequent Analysis

Thereafter, DNA was ready for subsequent PCR applications, for example real time PCR quantification, PCR and sequencing, etc. The six processed reactions (two samples, two negative controls and two positive controls) were subjected to HB14 real time PCR quantification using the LIGHTCYCLER™ system (Roche, Germany) according to example 10b. Each quantification was performed in duplicates (10 μl input in PCR reaction each). Table 22 shows the results of this quantification. The yield of DNA is in the range of 66% to 80% (based on positive controls with known DNA inputs). Samples resulted in 175 pg and 73 pg DNA, respectively (Table 22).

TABLE 22

Yield of bisulfite converted DNA derived from laser capture microdissected cells and controls.

| Sample | DNA in 1. PCR (10 μl input) [pg] | DNA in 2. PCR (10 μl input) [pg] | DNA total in both PCR [pg] | yield [%] |
|---|---|---|---|---|
| positive control 1 (500 pg DNA) | 192 | 206 | 398 | 79.6 |
| positive control 2 (500 pg DNA) | 234 | 96.5 | 330.5 | 66.1 |
| negative control 1 (no DNA) | 0 | 0 | 0 | x |
| negative control 0 (no DNA) | 0 | 0 | 0 | x |
| sample 1 | 96.1 | 78.6 | 174.7 | x |
| sample 2 | 7.5 | 65.1 | 72.6 | x |

The invention claimed is:

1. A method for providing DNA fragments derived from an archived sample, comprising:
contacting an archived sample comprising DNA with a protease to provide for an amount of protease-treated DNA;
extracting the protease-treated DNA;
reacting the extracted DNA with a bisulfite reagent, wherein the reaction is carried out in an organic solvent; and
purifying the bisulfite-treated DNA.

2. The method of claim 1, wherein the yield of the purified DNA is between about 30% and about 50% of that of the archived sample.

3. The method of claim 1, wherein 5% to about 60% of the purified DNA is amplifiable in a PCR reaction generating fragments of at least 110 bp in length.

4. The method of claim 1, wherein an average of about 10% of the purified DNA is amplifiable in a PCR reaction generating fragments of at least 110 bp in length.

5. The method of claim 1, wherein the archived sample is at least one selected from the group consisting of; a paraffin-embedded tissue biopsy; a fixed tissue biopsy; a paraffin-embedded, fixed tissue biopsy; a paraffin-embedded tissue section or portion thereof; a fixed tissue section or portion thereof; a paraffin-embedded, fixed tissue section or portion thereof.

6. The method of claim 5, further comprising at least one step selected from the group consisting of: removing paraffin; and amplifying the DNA.

7. The method of claim 6, wherein removing paraffin comprises dissolving the paraffin by an organic solvent, or comprises dissolving the paraffin by an organic solvent and washing by another organic solvent.

8. The method of claim 7, wherein the organic solvent for dissolving paraffin is a solvent selected from the group consisting of limonene, xylene and combinations of these solvents, and wherein the washing solvent is a solvent selected from the group consisting of ethanol, methanol, isopropanol and combinations of these solvents with each other or with water.

9. The method of claim 7, wherein the paraffin removal step comprises:
adding 0.1-3 ml of limonene to the archived sample;
incubating for at least 5 min at a temperature in the range of about 10° C. to about 70° C.;
centrifuging the incubated sample; and
removing of the limonene therefrom.

10. The method of claim 7, wherein the paraffin removal step comprises:
adding about 1 ml of limonene to the archived sample;
incubating for about 10 min to about 1 h at room temperature with mixing of the sample;
centrifuging the incubated sample at a force of at least 5,000×g for about 5 min; and
removing the limonene therefrom.

11. The method of claim 8, wherein the washing solvent is ethanol, and wherein washing comprises:
adding about 0.1 to about 3 ml of ethanol;
centrifuging the ethanol containing sample;
removing the ethanol; and
drying.

12. The method of claim 11, further comprising, after addition of the ethanol, incubation for up to 10 min at a temperature in the range of about 15° C. to about 30° C.

13. The method of claim 7, comprising:
adding of about 1 ml ethanol;
incubating for about 10 min at room temperature with mixing the sample;
Centrifuging at a force of at least 5,000×g for about 5 min;
removing the ethanol; and
incubating for a period of about 10 to about 30 min at about 50° C.

14. The method of claim 6, wherein the protease is selected from the group consisting of a serine protease, a thiol protease, a carboxy protease, a metalloprotease, proteinase K and combinations of these proteases.

15. The method of claim 14, wherein contacting the archived sample with the protease comprises:
  adding about 0.05 to about 1 ml of lysis buffer comprising about 50 mmol/l tris-hydroxymethyl-amino-methan pH 8.0, 1 mmol/l EDTA, 0.5% Tween 20 v/v to from 1 to about 10 deparaffinated formalin-fixed tissue sections, or to an equal amount of a deparaffinated formalin-fixed tissue biopsy;
  adding about 10 to about 100μ of a proteinase K solution comprising about 10 to about 30 g/l proteinase K, and subsequently agitating the sample; and
  incubating for at least 2.5 h at a temperature of about 40 to about 70° C.

16. The method of claim 15, further comprising, after incubating, inactivating the proteinase K by heating, by use of an inhibitor, or both.

17. The method of claim 14, wherein contacting the archived sample with the protease comprises:
  adding about 190 μl of lysis buffer to 1 to about 6 deparaffinated formalin-fixed tissue sections, or to an equal amount of a deparaffinated formalin-fixed tissue biopsy;
  adding about 20 μl of proteinase K solution comprising about 30 g/l proteinase K, with subsequent vortexing;
  incubating for a period of about 3 to about 48 h at a temperature of about 50° C. to about 60° C. with mixing the sample; and
  incubation for about 10 min at a temperature of at least 95° C.

18. The method of claim 17, further comprising, after incubating at about 50° C. to about 60° C. with mixing for 24 h, adding of at least 20 μl proteinase K solution after the first 24 h incubation at 50° C.-60° C., and prior to incubation at the temperature of at least 95° C.

19. The method according to claim 14, wherein contacting the archived sample with the protease comprises:
  adding about 50 to about 1,000 μl of lysis buffer to 1 to about 10 deparaffinated formalin-fixed tissue sections, or to an equal amount of a deparaffinated formalin-fixed tissue biopsy, the lysis buffer pH 8.0 comprising about 50 mmol/l tris-hydroxymethyl-amino-methan, 1 mmol/l EDTA, 0.5% Tween 20 v/v;
  incubating for about 5 to about 20 min at a temperature of about 40 to about 75° C.;
  adding about 5 to about 40 μl of proteinase K solution, the proteinase K solution comprising about 30 mg/ml proteinase K; and
  incubating for at least 2.5 h at a temperature of about 40 to about 70° C.

20. The method of claim 19, wherein the lysis buffer further comprises about 5 ng/μl poly-dA DNA.

21. The method of claim 19, wherein the proteinase K is activated by heating, by use of an inhibitor, or both.

22. The method according to claim 19, wherein contacting the archived sample with the protease comprises:
  adding about 100μ lysis buffer to 1 to about 6 deparaffinated formalin-fixed tissue sections, or to an equal amount of a deparaffinated formalin-fixed tissue biopsy;
  incubating for about 10 min at about 65° C. in a thermo mixer at 1,000 rpm;
  incubating at about 50° C. in a thermo mixer at about 1,400 rpm adding about 10 μl of proteinase K solution;
  incubating for about 3 to about 48 h at about 60° C. in a thermo mixer at about 1,000 rpm; and
  incubating for about 10 min at a temperature greater than 95° C.

23. The method of claim 6, wherein extracting the DNA comprises binding of DNA to silica surfaces, or silica membranes.

24. The method according to claim 23, wherein binding of DNA to silica surfaces, or silica membranes comprises utilizing a DNA extraction step from at least one kit, wherein the at least one kit is selected from products containing silica surfaces or silica membranes appropriate for binding DNA sold under the trademarks DNEASY® 96 Tissue Kit, QIAAMP® 96 DNA Blood Kit, QIAAMP® DSP 96 Virus MDX Kit, DNEASY® Tissue Kit, QIAAMP® DNA Mini Kit, or QIAAMP® DNA Micro Kit, QIAAMP® Viral RNA Mini, and QIAAMP® DSP Virus Kit.

25. The method of claim 6, wherein treating the extracted DNA with a bisulfite reagent comprises:
  mixing of about 10 to about 60 μl of the solution containing the genomic DNA with about 50 to about 120 μl of bisulfite solution, the bisulfite solution having a pH in the range of about 5.45 to about 5.50 comprising about 4.83 to about 4.93 mol/l hydrogensulfite;
  adding about 8 to about 45 μl of an organic radical scavenger solution, the organic radical scavenger solution comprising an organic solvent and about 158 to about 500 mmol/l of 6-hydroxy-2,5,7,8-tetramethyl-chroman-2-carboxylic acid; and
  applying a temperature protocol for about 3 to about 8 h, wherein the reaction is conducted in a temperature range of about 0 to about 80° C. with about 2 to about 5 additional temperature increases, in each case for about 1 to about 10 min, to a temperature of about 85 to about 100° C. including an initial temperature increase to a temperature of about 85 to about 100° C.

26. The method of claim 25, wherein treating the extracted DNA with a bisulfite reagent comprises:
  mixing of about 44 to about 50 μl of a solution containing the genomic DNA with about 83 to about 95 μl of the bisulfite solution;
  adding about 13 to about 15 μl of DME solution, the DME solution comprising about 500 mmol/l of 6-hydroxy-2, 5,7,8-tetramethyl-chroman-2-carboxylic acid dissolved in diethyleneglycoldimethylether; and
  applying a temperature protocol for about 4 to about 7 h, wherein the reaction is conducted in a temperature range of about 57 to about 65° C. with about 2 to about 5 additional temperature increases, in each case for about 3 to about 5 min, to a temperature of about 94 to about 100° C. including an initial temperature increase to a temperature of about 94 to about 100° C.

27. Method according to claim 25, wherein treating the extracted DNA with a bisulfite reagent comprises:
  mixing about 15 to about 20 μl of solution containing the genomic DNA with about 60 to about 85 μl of the bisulfite solution;
  adding about 25 to about 35 μl of dioxane solution, the dioxane solution comprising about 158 mmol/l of 6-hydroxy-2,5,7,8-tetramethyl-chroman-2-carboxylic acid dissolved in 1,4-dioxane; and
  applying a temperature protocol for about 4 to about 7 h, wherein the reaction is conducted in a temperature range of about 57 to about 65° C. with about 2 to about 5 additional temperature increases, in each case for about 3 to about 5 min, to a temperature of about 94 to about 100° C. including an initial temperature increase to a temperature of about 94 to about 100° C.

28. The method of claim 6, wherein purifying the bisulfite-treated DNA comprises use of a centrifugal filter device, and further comprises:

adjusting the sample after the bisulfite reaction with water to a volume of about 350 to about 500 μl;

binding of the DNA onto a centrifugal filter device;

treating with about 25 to about 1,000 μl of about 0.2 mol/l sodium hydroxide, wherein there is optional incubating for about 3 to about 25 min at a temperature of about 15 to about 26° C.;

washing with about 200 to about 1,000 μl TE buffer, the TE buffer pH 8.0 comprising about 10 mmol/l tris-hydroxymethyl-amino-methan and about 0.1 mmol/l EDTA;

removing the DNA by means of about 30 to about 100 μl TE buffer preheated to a temperature of about 40 to about 65° C. incubated for about 5 to about 25 min at a temperature of about 10 to about 60° C.

29. The method of claim 28, wherein purifying the bisulfite treated DNA comprises:

adjusting the sample after the bisulfite reaction with water to a volume of about 400 μl;

applying the mixture onto a centrifugal filter device and subsequent centrifugation at about 14,000×g for about 15 min, wherein there are 1 to 2 optional repetitions of the following washing step: applying of about 400 μl TE buffer, the TE buffer pH 8 containing about 10 mmol/l tris-hydroxymethyl-amino-methan and about 0.1 mmol/l EDTA, subsequent centrifuging at about 14,000×g for about 12 min;

applying about 100 to about 400 μl of about 0.2 mol/l sodium hydroxide, wherein there is optional incubating for about 10 min at room temperature, and subsequent centrifuging at about 14,000×g for about 10 to about 12 min;

applying, in 1 to about 4 repetitions, the following: applying of about 400 μl water or TE buffer and subsequent centrifuging at about 14,000×g for about 12 min; and eluting in one or two steps by application of about 37.5 to about 75 μl TE buffer preheated to about 50° C., incubation for about 10 min at a temperature of about 15 to about 50° C., and subsequent inversion of the centrifugal filter device and centrifugation at about 1,000×g for about 5 min.

30. The method of claim 6, wherein amplifying of the DNA comprises use of at least one method selected from the group consisting of the PCR method; the bisulfite sequencing method; the Combined Bisulfite Restriction Analysis (COBRA) method; the Methylation-sensitive Single Nucleotide Primer Extension (Ms-SNuPE) method; the Methylation Specific PCR MSP method; the nested MSP method; the HEAVYMETHYL® method; the MethyLight method; and the quantitative methylation (QM) assay.

31. The method of claim 1, wherein, with respect to purifying the bisulfite-treated DNA, the yield of the purified DNA is at least 20% of that of the archived sample, and wherein at least 5% of the purified DNA is amplifiable in a PCR reaction generating fragments of at least 110 bp in length.

32. The method of claim 1, wherein the organic solvent is of structural formula (I):

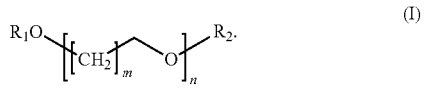

n = 1-35000
m = 1-3
R1 = H, Me, Et, Pr, Bu
R2 = H, Me, Et, Pr, Bu

* * * * *

SEQUENCE LISTING

```
<160> NUMBER OF SEQ ID NOS: 72

<210> SEQ ID NO 1
<211> LENGTH: 22
<212> TYPE: DNA
<213> ORGANISM: Homo Sapiens

<400> SEQUENCE: 1 ggaggggta gagttattag tt                                          22

<210> SEQ ID NO 2
<211> LENGTH: 22
<212> TYPE: DNA
<213> ORGANISM: Homo Sapiens

<400> SEQUENCE: 2
tatacttcct caaacaaccc tc                                         22

<210> SEQ ID NO 3
<211> LENGTH: 22
<212> TYPE: DNA
<213> ORGANISM: Homo Sapiens

<400> SEQUENCE: 3
gtgatatttg gggattgtta tt                                         22

<210> SEQ ID NO 4
<211> LENGTH: 20
<212> TYPE: DNA
<213> ORGANISM: Homo Sapiens

<400> SEQUENCE: 4
actccctccc ctatcttaca                                            20

<210> SEQ ID NO 5
<211> LENGTH: 21
<212> TYPE: DNA
<213> ORGANISM: Homo Sapiens

<400> SEQUENCE: 5
tttgttggga tttgttagga t                                          21

<210> SEQ ID NO 6
<211> LENGTH: 22
<212> TYPE: DNA
```

<213> ORGANISM: Homo Sapiens

<400> SEQUENCE: 6
aaacatttta ccctctaaa cc                                             22

<210> SEQ ID NO 7
<211> LENGTH: 24
<212> TYPE: DNA
<213> ORGANISM: Homo Sapiens

<400> SEQUENCE: 7
tgattgtgta gattattttt ggtt                                          24

<210> SEQ ID NO 8
<211> LENGTH: 23
<212> TYPE: DNA
<213> ORGANISM: Homo Sapiens

<400> SEQUENCE: 8
caaactctct aaacctcaat ctc                                           23

<210> SEQ ID NO 9
<211> LENGTH: 22
<212> TYPE: DNA
<213> ORGANISM: Homo Sapiens

<400> SEQUENCE: 9
ttggtgatgt tgattagagt tt                                            22

<210> SEQ ID NO 10
<211> LENGTH: 22
<212> TYPE: DNA
<213> ORGANISM: Homo Sapiens

<400> SEQUENCE: 10
taaaacacct tacattttcc ct                                            22

<210> SEQ ID NO 11
<211> LENGTH: 22
<212> TYPE: DNA
<213> ORGANISM: Homo Sapiens

<400> SEQUENCE: 11
ggtagaggaa gtagttggtt tg                                            22

<210> SEQ ID NO 12
<211> LENGTH: 23
<212> TYPE: DNA
<213> ORGANISM: Homo Sapiens

<400> SEQUENCE: 12
cttttatatt tctcccaatc tcc                                           23

<210> SEQ ID NO 13
<211> LENGTH: 21
<212> TYPE: DNA
<213> ORGANISM: Homo Sapiens

<400> SEQUENCE: 13 gtagggagg gaagtagatg t                                              21

<210> SEQ ID NO 14
<211> LENGTH: 23
<212> TYPE: DNA

```
<213> ORGANISM: Homo Sapiens

<400> SEQUENCE: 14
tcctcaactc tacaaaccta aaa                                              23

<210> SEQ ID NO 15
<211> LENGTH: 130
<212> TYPE: DNA
<213> ORGANISM: Artificial Sequence
<220> FEATURE:
<223> OTHER INFORMATION: GSTP1-C3_bis-sequence_example_9.5.1.

<400> SEQUENCE: 15
ggagtggagg aaattgagat ttattgaggt tacgtagttt gtttaaggtt aagtttgggt      60
gtttgtaatt tttgttttgt gttaggttgt tttttaggtg ttaggtgagt tttgagtatt     120
tgttgtgtgg                                                            130

<210> SEQ ID NO 16
<211> LENGTH: 20
<212> TYPE: DNA
<213> ORGANISM: Homo Sapiens

<400> SEQUENCE: 16
ggagtggagg aaattgagat                                                  20

<210> SEQ ID NO 17
<211> LENGTH: 22
<212> TYPE: DNA
<213> ORGANISM: Homo Sapiens

<400> SEQUENCE: 17
ccacacaaca aatactcaaa ac                                               22

<210> SEQ ID NO 18
<211> LENGTH: 33
<212> TYPE: DNA
<213> ORGANISM: Homo Sapiens

<400> SEQUENCE: 18
tgggtgtttg taattttgt tttgtgttag gtt                                    33

<210> SEQ ID NO 19
<211> LENGTH: 25
<212> TYPE: DNA
<213> ORGANISM: Homo Sapiens

<400> SEQUENCE: 19
tggtgatgga ggaggtttag taagt                                            25

<210> SEQ ID NO 20
<211> LENGTH: 27
<212> TYPE: DNA
<213> ORGANISM: Homo Sapiens

<400> SEQUENCE: 20
aaccaataaa acctactcct cccttaa                                          27

<210> SEQ ID NO 21
<211> LENGTH: 30
<212> TYPE: DNA
<213> ORGANISM: Homo Sapiens

<400> SEQUENCE: 21
```

```
ttgtgaattt gtgtttgtta ttgtgtgttg                                 30

<210> SEQ ID NO 22
<211> LENGTH: 30
<212> TYPE: DNA
<213> ORGANISM: Homo Sapiens

<400> SEQUENCE: 22
tggtggttat ttttttttatt aggttgtggt                                30

<210> SEQ ID NO 23
<211> LENGTH: 20
<212> TYPE: DNA
<213> ORGANISM: Homo Sapiens

<400> SEQUENCE: 23
ggagtggagg aaattgagat                                            20

<210> SEQ ID NO 24
<211> LENGTH: 22
<212> TYPE: DNA
<213> ORGANISM: Homo Sapiens

<400> SEQUENCE: 24
ccacacaaca aatactcaaa ac                                         22

<210> SEQ ID NO 25
<211> LENGTH: 33
<212> TYPE: DNA
<213> ORGANISM: Homo Sapiens

<400> SEQUENCE: 25
tgggtgtttg taattttttgt tttgtgttag gtt                            33

<210> SEQ ID NO 26
<211> LENGTH: 25
<212> TYPE: DNA
<213> ORGANISM: Homo Sapiens

<400> SEQUENCE: 26
taagagtaat aatggatgga tgatg                                      25

<210> SEQ ID NO 27
<211> LENGTH: 17
<212> TYPE: DNA
<213> ORGANISM: Homo Sapiens

<400> SEQUENCE: 27
cctcccatct cccttcc                                               17

<210> SEQ ID NO 28
<211> LENGTH: 25
<212> TYPE: DNA
<213> ORGANISM: Homo Sapiens

<400> SEQUENCE: 28
atggatgaag aaagaaagga tgagt                                      25

<210> SEQ ID NO 29
<211> LENGTH: 25
<212> TYPE: DNA
<213> ORGANISM: Homo Sapiens

<400> SEQUENCE: 29
```

```
tttttgtagt ttagaaggag gttag                                    25

<210> SEQ ID NO 30
<211> LENGTH: 22
<212> TYPE: DNA
<213> ORGANISM: Homo Sapiens

<400> SEQUENCE: 30
acacaataaa ttcaaccacc aa                                       22

<210> SEQ ID NO 31
<211> LENGTH: 18
<212> TYPE: DNA
<213> ORGANISM: Homo Sapiens

<400> SEQUENCE: 31
gggagattta atttgggg                                            18

<210> SEQ ID NO 32
<211> LENGTH: 20
<212> TYPE: DNA
<213> ORGANISM: Homo Sapiens

<400> SEQUENCE: 32
caccctctaa taaccaacca                                          20

<210> SEQ ID NO 33
<211> LENGTH: 21
<212> TYPE: DNA
<213> ORGANISM: Homo Sapiens

<400> SEQUENCE: 33
ttaggtataa gttggtggtg g                                        21

<210> SEQ ID NO 34
<211> LENGTH: 20
<212> TYPE: DNA
<213> ORGANISM: Homo Sapiens

<400> SEQUENCE: 34
cccataaaca acccctaaaa                                          20

<210> SEQ ID NO 35
<211> LENGTH: 22
<212> TYPE: DNA
<213> ORGANISM: Homo Sapiens

<400> SEQUENCE: 35
aggtatagga tggggaatta gt                                       22

<210> SEQ ID NO 36
<211> LENGTH: 21
<212> TYPE: DNA
<213> ORGANISM: Homo Sapiens

<400> SEQUENCE: 36
aacccaaacc cttatacaaa c                                        21

<210> SEQ ID NO 37
<211> LENGTH: 21
<212> TYPE: DNA
<213> ORGANISM: Homo Sapiens

<400> SEQUENCE: 37
```

```
gtttttggag ttaattggga g                                        21

<210> SEQ ID NO 38
<211> LENGTH: 20
<212> TYPE: DNA
<213> ORGANISM: Homo Sapiens

<400> SEQUENCE: 38 caccccatc attactattc                                           20

<210> SEQ ID NO 39
<211> LENGTH: 18
<212> TYPE: DNA
<213> ORGANISM: Homo Sapiens

<400> SEQUENCE: 39
agggtagagg gtgttggt                                            18

<210> SEQ ID NO 40
<211> LENGTH: 21
<212> TYPE: DNA
<213> ORGANISM: Homo Sapiens

<400> SEQUENCE: 40
ccaaaactat aaaccttccc a                                        21

<210> SEQ ID NO 41
<211> LENGTH: 22
<212> TYPE: DNA
<213> ORGANISM: Homo Sapiens

<400> SEQUENCE: 41
tttagtatgg gttgagagga gt                                       22

<210> SEQ ID NO 42
<211> LENGTH: 24
<212> TYPE: DNA
<213> ORGANISM: Homo Sapiens

<400> SEQUENCE: 42
cctctttcct aaaactacac attc                                     24

<210> SEQ ID NO 43
<211> LENGTH: 22
<212> TYPE: DNA
<213> ORGANISM: Homo Sapiens

<400> SEQUENCE: 43
ggattattgt tgggtatttg tt                                       22

<210> SEQ ID NO 44
<211> LENGTH: 22
<212> TYPE: DNA
<213> ORGANISM: Homo Sapiens

<400> SEQUENCE: 44
acacttccct aaaatcttca aa                                       22

<210> SEQ ID NO 45
<211> LENGTH: 22
<212> TYPE: DNA
<213> ORGANISM: Homo Sapiens

<400> SEQUENCE: 45
```

-continued gttggatttg tttagagaga gg                                    22

<210> SEQ ID NO 46
<211> LENGTH: 23
<212> TYPE: DNA
<213> ORGANISM: Homo Sapiens

<400> SEQUENCE: 46
acatttaact ctttatccca aaa                                   23

<210> SEQ ID NO 47
<211> LENGTH: 22
<212> TYPE: DNA
<213> ORGANISM: Homo Sapiens

<400> SEQUENCE: 47
ttatttgatg gggatagaga tt                                    22

<210> SEQ ID NO 48
<211> LENGTH: 21
<212> TYPE: DNA
<213> ORGANISM: Homo Sapiens

<400> SEQUENCE: 48
acaaacaaca caccctcata c                                     21

<210> SEQ ID NO 49
<211> LENGTH: 22
<212> TYPE: DNA
<213> ORGANISM: Homo Sapiens

<400> SEQUENCE: 49
tgtaatgaaa gaaggtgttg ag                                    22

<210> SEQ ID NO 50
<211> LENGTH: 22
<212> TYPE: DNA
<213> ORGANISM: Homo Sapiens

<400> SEQUENCE: 50
ttaactaaac catccataac cc                                    22

<210> SEQ ID NO 51
<211> LENGTH: 23
<212> TYPE: DNA
<213> ORGANISM: Homo Sapiens

<400> SEQUENCE: 51
ggattatagg aattagaatg ggt                                   23

<210> SEQ ID NO 52
<211> LENGTH: 23
<212> TYPE: DNA
<213> ORGANISM: Homo Sapiens

<400> SEQUENCE: 52
tctttccaac tcaacatctt act                                   23

<210> SEQ ID NO 53
<211> LENGTH: 20
<212> TYPE: DNA
<213> ORGANISM: Homo Sapiens

<400> SEQUENCE: 53
tggtggtatg gattggataa                                              20

<210> SEQ ID NO 54
<211> LENGTH: 22
<212> TYPE: DNA
<213> ORGANISM: Homo Sapiens

<400> SEQUENCE: 54
tcccccaaat aacacaatat ac                                           22

<210> SEQ ID NO 55
<211> LENGTH: 23
<212> TYPE: DNA
<213> ORGANISM: Homo Sapiens

<400> SEQUENCE: 55
agaggaaaga gtaaggaatt ttt                                          23

<210> SEQ ID NO 56
<211> LENGTH: 18
<212> TYPE: DNA
<213> ORGANISM: Homo Sapiens

<400> SEQUENCE: 56
cttatccccc acaaaacc                                                18

<210> SEQ ID NO 57
<211> LENGTH: 19
<212> TYPE: DNA
<213> ORGANISM: Homo Sapiens

<400> SEQUENCE: 57
ggtggaggga gagttaagg                                               19

<210> SEQ ID NO 58
<211> LENGTH: 19
<212> TYPE: DNA
<213> ORGANISM: Homo Sapiens

<400> SEQUENCE: 58
ccaacaaaac gccctctcc                                               19

<210> SEQ ID NO 59
<211> LENGTH: 22
<212> TYPE: DNA
<213> ORGANISM: Homo Sapiens

<400> SEQUENCE: 59
gattgagatt attttgggtt tt                                           22

<210> SEQ ID NO 60
<211> LENGTH: 21
<212> TYPE: DNA
<213> ORGANISM: Homo Sapiens

<400> SEQUENCE: 60
acttaaacct tccctctcca c                                            21

<210> SEQ ID NO 61
<211> LENGTH: 22
<212> TYPE: DNA
<213> ORGANISM: Homo Sapiens

<400> SEQUENCE: 61

```
ttaagtattg gatttggggt ta                                              22

<210> SEQ ID NO 62
<211> LENGTH: 24
<212> TYPE: DNA
<213> ORGANISM: Homo Sapiens

<400> SEQUENCE: 62
acctaccctc taactctaca aaaa                                            24

<210> SEQ ID NO 63
<211> LENGTH: 24
<212> TYPE: DNA
<213> ORGANISM: Homo Sapiens

<400> SEQUENCE: 63
agtaaatagt gggtgagtta tgaa                                            24

<210> SEQ ID NO 64
<211> LENGTH: 24
<212> TYPE: DNA
<213> ORGANISM: Homo Sapiens

<400> SEQUENCE: 64
aaaaacctct aaaaactact ctcc                                            24

<210> SEQ ID NO 65
<211> LENGTH: 22
<212> TYPE: DNA
<213> ORGANISM: Homo Sapiens

<400> SEQUENCE: 65
aaggttttag ggaagagtgt tt                                              22

<210> SEQ ID NO 66
<211> LENGTH: 23
<212> TYPE: DNA
<213> ORGANISM: Homo Sapiens

<400> SEQUENCE: 66
accttttcct atcacaaaaa taa                                             23

<210> SEQ ID NO 67
<211> LENGTH: 22
<212> TYPE: DNA
<213> ORGANISM: Homo Sapiens

<400> SEQUENCE: 67 aggggaatt aaatagaaag ag                                               22

<210> SEQ ID NO 68
<211> LENGTH: 22
<212> TYPE: DNA
<213> ORGANISM: Homo Sapiens

<400> SEQUENCE: 68
caataaaacc atcccaaata ct                                              22

<210> SEQ ID NO 69
<211> LENGTH: 22
<212> TYPE: DNA
<213> ORGANISM: Homo Sapiens

<400> SEQUENCE: 69
```

-continued

```
tatgggagga ggttagtaag tg                                      22

<210> SEQ ID NO 70
<211> LENGTH: 22
<212> TYPE: DNA
<213> ORGANISM: Homo Sapiens

<400> SEQUENCE: 70
ccccaaatcc tacatataaa aa                                      22

<210> SEQ ID NO 71
<211> LENGTH: 22
<212> TYPE: DNA
<213> ORGANISM: Homo Sapiens

<400> SEQUENCE: 71
gtattatgtg gtttaaggag gg                                      22

<210> SEQ ID NO 72
<211> LENGTH: 22
<212> TYPE: DNA
<213> ORGANISM: Homo Sapiens

<400> SEQUENCE: 72
actccaaaca aattcaacaa ct                                      22
```